US011376255B2

(12) United States Patent
Crosignani et al.

(10) Patent No.: US 11,376,255 B2
(45) Date of Patent: Jul. 5, 2022

(54) THIOCARBAMATE DERIVATIVES AS A2A INHIBITORS, PHARMACEUTICAL COMPOSITION THEREOF AND COMBINATIONS WITH ANTICANCER AGENTS

(71) Applicant: iTeos Belgium SA, Gosselies (BE)

(72) Inventors: Stefano Crosignani, Nivelles (BE); Erica Joke Katelijne Heleen Houthuys, Petit-Enghien (BE); Reece Gerrad Marillier, Chaumont-Gistoux (BE); Chiara Martinoli, Milan (IT); Oliver De Henau, Watermaele-Boitsfort (BE); Gregory Driessens, Ottignies (BE)

(73) Assignee: iTeos Belgium SA, Gosselies (BE)

( * ) Notice: Subject to any disclaimer, the term of this patent is extended or adjusted under 35 U.S.C. 154(b) by 0 days.

(21) Appl. No.: 17/015,850

(22) Filed: Sep. 9, 2020

(65) Prior Publication Data
US 2021/0069196 A1   Mar. 11, 2021

Related U.S. Application Data

(63) Continuation of application No. PCT/EP2019/074208, filed on Sep. 11, 2019.

(60) Provisional application No. 62/737,723, filed on Sep. 27, 2018, provisional application No. 62/729,808, filed on Sep. 11, 2018.

(30) Foreign Application Priority Data

Sep. 11, 2018  (BE) .................................. 2018/0103
Sep. 27, 2018  (BE) .................................. 2018/0114

(51) Int. Cl.
| *A61K 31/519*   | (2006.01) |
| *A61P 35/00*    | (2006.01) |
| *A61K 31/5377*  | (2006.01) |
| *A61K 33/243*   | (2019.01) |
| *A61K 9/48*     | (2006.01) |
| *A61K 31/704*   | (2006.01) |
| *A61K 39/395*   | (2006.01) |

(52) U.S. Cl.
CPC .......... *A61K 31/519* (2013.01); *A61K 9/4858* (2013.01); *A61K 9/4866* (2013.01); *A61K 31/5377* (2013.01); *A61K 31/704* (2013.01); *A61K 33/243* (2019.01); *A61K 39/3955* (2013.01); *A61P 35/00* (2018.01)

(58) Field of Classification Search
CPC .............. A61K 31/519; A61K 31/5377; A61K 39/3955; A61P 35/00
USPC ..................................................... 424/172.1
See application file for complete search history.

(56) References Cited

U.S. PATENT DOCUMENTS

| 2005/0239795 A1 | 10/2005 | Neustadt et al. |
| 2017/0088613 A1 | 3/2017 | Grogan et al. |
| 2019/0276473 A1 | 9/2019 | Crosignani et al. |
| 2020/0102319 A1 | 4/2020 | Crosignani |

FOREIGN PATENT DOCUMENTS

| IN | 274489 B | 1/2011 |
| WO | WO-2000/015231 A1 | 3/2000 |
| WO | WO-2003/095457 A1 | 11/2003 |
| WO | WO-2004/092171 A2 | 10/2004 |
| WO | WO-2007/140181 A2 | 12/2007 |
| WO | WO-2009/011897 A1 | 1/2009 |
| WO | WO-2009/156737 A1 | 12/2009 |

(Continued)

OTHER PUBLICATIONS

U.S. Appl. No. 16/354,022, 2-Oxo-Thiazole Derivatives as A2A Inhibitors and Compounds for Use in the Treatment of Cancers, filed Mar. 14, 2019, Allowed.

(Continued)

*Primary Examiner* — Yan Xiao
(74) *Attorney, Agent, or Firm* — Goodwin Procter LLP

(57) ABSTRACT

The present invention relates to thiocarbamate derivatives of Formula (I) which are useful as A2A adenosine receptor (A2AR) inhibitors

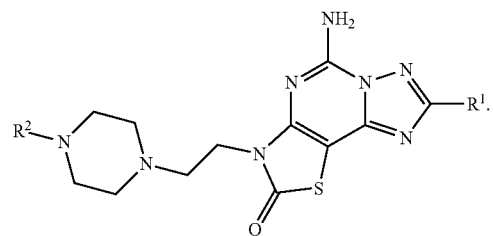

(I)

Especially, the present invention relates to a pharmaceutical composition comprising an A2A inhibitor of Formula (I) and a lipid carrier such as lauroyl macrogol-32 glycerides, D-α-tocopherol-polyethylene glycol-1000 succinate or a mixture thereof. The pharmaceutical composition of the invention is particularly useful for oral dosing in the treatment of cancers. The present invention also relates to a combination comprising an A2A receptor inhibitor of Formula (I) and an anticancer agent. The anticancer agent is for example an immunotherapeutic agent, such as a checkpoint inhibitor. The invention further relates to a pharmaceutical composition and a kit of parts comprising such combination. Additionally, the combination of the invention is particularly useful for the treatment and/or prevention of cancers.

6 Claims, 12 Drawing Sheets
Specification includes a Sequence Listing.

(56) References Cited

FOREIGN PATENT DOCUMENTS

| WO | WO-2011/095626 A2 | 8/2011 |
|---|---|---|
| WO | WO-2011/112687 A2 | 9/2011 |
| WO | WO-2011/121418 A1 | 10/2011 |
| WO | WO-2012/038980 A2 | 3/2012 |
| WO | WO-2012/055015 A1 | 5/2012 |
| WO | WO-2012/135084 A1 | 10/2012 |
| WO | WO-2015/173764 A1 | 11/2015 |
| WO | WO-2018/136700 A1 | 7/2018 |
| WO | WO-2018/160704 A1 | 9/2018 |
| WO | WO-2018/178338 A1 | 10/2018 |
| WO | WO-2019/023504 A1 | 1/2019 |
| WO | WO-2019/123482 A1 | 6/2019 |
| WO | WO-2020/053263 A1 | 3/2020 |
| WO | WO-2020/065036 A1 | 4/2020 |
| WO | 2020144178 | 7/2020 |

OTHER PUBLICATIONS

U.S. Appl. No. 16/993,897, 2-Oxo-Thiazole Derivatives as A2A Inhibitors and Compounds for Use in the Treatment of Cancers, filed Aug. 14, 2020, Pending.

U.S. Appl. No. 16/584,596, Non Brain Penetrant A2A Inhibitors and Methods for Use in the Treatment of Cancers, filed Sep. 26, 2019, Published.

Allard, B., et al., "Immunosuppressive activities of adenosine in cancer.", Curr. Opin. Pharmacol., Aug. 2016, vol. 29: pp. 7-16.

Anderson CM et al.: "Distribution of Equilibrative, Nitrobenzylthioinosine-Sensitive Nucleoside Transporters (ENT1) in Brain," Neurochem (1999) 73:867-873.

Andre B. Da Fonseca Antunes, et al., "Gelucire 44/14 based immediate release formulations for poorly water-soluble drugs", Drug Development and Industrial Pharmacy,vol. 39, No. 5, May 1, 2013, p. 791-798.

Antonioli L et al.: "Immunity, inflammation and cancer: a leading role for adenosine," Nature Reviews Cancer (2013) 13:842-857.

Barbara Cacciari, et al., "A2A Adenosine Receptor Antagonists as Therapeutic Candidates: Are They Still an Interesting Challenge?", Mini Reviews in Medicinal Chemistry,vol. 18, No. 14, Jul. 9, 2018, p. 1168-1174.

Blay J et al.: "The extracellular fluid of solid carcinomas contains immunosuppressive concenbations of adenosine," Cancer Res (1997) 57:2602-2605.

Bonnal RJP et al.: "De novo transcriptome profiling of highly purified human lymphocytes primary cells," Nature (2015) 2:150051.

Cekic C and Linden J: "Purinergic regulation of the immune system", Nature Reviews | Immunology (2016) 16:177-192.

Conglian Yang, et al., "Recent Advances in the Application of Vitamin E TPGS for Drug Delivery", Theranostics,vol. 8, No. 2, Jan. 1, 2018, p. 464-485.

Gengyang Yuan, et al., "Fluorinated Adenosine A2A Receptor Antagonists Inspired by Preladenant as Potential Cancer Immunotherapeutics", International Journal of Medicinal Chemistry,vol. 2017, Jan. 1, 2017, p. 1-8.

Griffith DA and Jarvis SM: "Nucleoside and nucleohase transport systems of mammalian cells," Biochim Biophys Acta (1996) 1286:153-181.

Hatfield Stephen M, et al., "A2A adenosine receptor antagonists to weaken the hypoxia-HIF-1-[alpha] driven immunosuppression and improve immunotherapies of cancer", Current Opinion in Pharmacology, Elsevier Science Publishers, NL,vol. 29, Aug. 17, 2016, p. 90-96.

Hauser, R.A., et al., "Preladenant as an Adjunctive Therapy With Levodopa in Parkinson Disease: Two Randomized Clinical Trials and Lessons Learned", JAMA Neurol., Dec. 2015, vol. 72, Issue 12: pp. 1491-1500.

Hodgson, R. A., et al., "Characterization of the Potent and Highly Selective A2A Receptor Antagonists Preladenant and SCH 412348 [7-[2-[4-2,4-Difluorophenyl]-1-plperazinyl]ethyl]-2-(2-furanyl)-7H-pyrazolo[4,3-e][1,2,4]trlazolo[1,5-c]pyrimidin-5-amine] in Rodent Models of Movement Disorders and Depression", The Journal of Pharmacology and Experimental Therapeutics, Jul. 2009, vol. 330, Issue 1: pp. 294-303.

Houthuys Erica, et al., "Abstract LB-291: EOS100850, an insurmountable and non-brain penetrant A2A receptor antagonist, inhibits adenosine-mediated T cell suppression, demonstrates anti-tumor activity and exhibits best-in class characteristics", Cancer Research, Apr. 14-18, 2018, Retrieved from the Internet: URL:https://cancerres.aacrjournals.org/content/78/13_Supplement/LB-291.

Written Opinion of the International Searching Authority and International Search Report for PCT/EP2019/074208 dated Jan. 17, 2020 (13 pages).

Written Opinion of the International Searching Authority and International Search Report for PCT/EP2019/076244 dated Aug. 1, 2020 (11 pages).

Nakagawa H, et al., "Basis for dosing time-dependent change in the anti-tumor effect of imatinib in mice", Biochemical Pharmacology, Nov. 15, 2006, vol. 72, No. 10, p. 1237-1245.

Ohta and Sitkovsky: "Role of G-protein-coupled adenosine receptors in downregulation of inflammation and protection from tissue damage," Nature (2001) 414:916-920.

Ohta, A., "A Metabolic Immune Checkpoint: Adenosine in Tumor Microenvironment", Frontiers in Immunology, Mar. 29, 2016, vol. 7, Article 109: pp. 1-11.

Pinna A., "Adenosine A2A Receptor Antagonists in Parkinson's Disease: Progress in Clinical Trials from the Newly Approved Istradefylline to Drugs in Early Development and Those Already Discontinued", CNS Drugs, May 2014, vol. 28, Issue 5: pp. 455-474.

Shryock JC and Belardinelli L: "Adenosine and adenosine receptors in the cardiovascular system: biochemistry, physiology, and pharamcology," Am J Cardiol (1997) 79(12):2-10.

Stagg J and Smyth MJ: "Extracellular adenosine triphosphate and adenosine in cancer," Oncogene (2010) 2:5346-5358.

Stephen B. Willingham, et al., "A2AR Antagonism with CPI-444 Induces Antitumor Responses and Augments Efficacy to Anti-PD-(L)1 and Anti-CTLA-4 in Preclincal Models", Cancer Immunology Research, vol. 6, No. 10, Oct. 21, 2018, p. 1136-1149.

STN Chemical Structure Search Results dated May 12, 2020 (31 pages).

STN Chemical Structure Search Results dated May 12, 2020 (41 pages).

Vijayan D et al.: "Targeting immunosuppressive adenosine in cancer," Nature Reviews cancer (2017) 17:709-724.

West, Anthony R., Solid State Chemistry and Its Applications, Wiley, New York, 1988, 358. (Year: 1988).

Written Opinion of the International Searching Authority an PCT/EP2018/058301 dated May 18, 2018 (10 pages).

THIOCARBAMATE DERIVATIVES AS A2A INHIBITORS, PHARMACEUTICAL COMPOSITION THEREOF AND COMBINATIONS WITH ANTICANCER AGENTS

FIELD OF INVENTION

The present invention relates to thiocarbamate derivatives which are useful as A2A adenosine receptor (A2AR) inhibitors.

Especially, the present invention relates to a pharmaceutical composition comprising a thiocarbamate derivative as adenosine A2A receptor inhibitor. The pharmaceutical composition of the invention is particularly useful for oral dosing in the treatment of cancers.

The present invention also relates to a combination comprising an A2A adenosine receptor (A2AR) inhibitor and an anticancer agent. The A2AR inhibitor is a thiocarbamate derivative of Formula (I) as defined below. The anticancer agent is for example an immunotherapeutic agent, such as for example a checkpoint inhibitor. The invention further relates to a pharmaceutical composition and a kit of parts comprising such combination. The combination of the invention is particularly useful for the treatment and/or prevention of cancers.

SEQUENCE LISTING

The instant application contains a Sequence Listing which has been filed electronically in ASCII format and is hereby incorporated by reference in its entirety. Said ASCII copy, created on Sep. 11, 2019, is named 1098_PCT_Sequence_Listing.txt and is 1,401 bytes in size.

BACKGROUND OF INVENTION

Many of the immunosuppressive mechanisms in tumors are common to physiological immunoregulation in normal tissues. Such immunoregulation is very important in keeping the immune system under control in order to block a self-reactive immune response and to prevent an ongoing immune response from causing critical tissue damage. The lack of physiological immunoregulation often results in overwhelming immune activation that accompanies autoimmunity. For example, CTLA-4 is a physiological mechanism that negatively regulates T cell activity by blocking a costimulatory signal through CD28-B7 interaction. The lack of CTLA4 causes non-specific T cell activation, and CTLA-4-deficient mice die in several weeks with massive lymphocytic tissue infiltration. PD-1 also provides a T cell inhibitory signal upon interaction with its ligands, PD-L1 and PD-L2. Deficiency of PD-1 in mice is known to cause various types of autoimmune disorders depending on the genetic strains.

Besides cell surface transducers of immunosuppressive signal, e.g., CTLA-4 and PD-1, immunosuppression in the tumor microenvironment involves anti-inflammatory cytokines (IL-10, TGF-β), enzymes (indoleamine-2,3-dioxygenase), and professional immunoregulatory cells (regulatory T cells, myeloid-derived suppressor cells MDSCs). These immunosuppressive mechanisms play an important role in controlling immune response in normal tissues. Since tumors take advantage of such physiological immunoregulatory mechanisms to protect their tissue from immune attack, these mechanisms intended to prevent inflammatory complication, now turn out to be major obstacles hampering spontaneous cancer regression and immunological cancer treatment. The identification of immunosuppressive mechanisms in tumors pointed out molecular targets to restore the antitumor immune response. Thus, these negative immunoregulatory mechanisms, so-called immune checkpoints, became a focus in drug discovery. Antibodies against PD1, PDL1 or CTLA4 have been approved as anticancer therapies on a large number of indications, such as Metastatic Melanoma, Non-Small Cell Lung Cancer, Renal Cell Carcinoma, Hodgkin's Lymphoma, Head and Neck Cancer, Urothelial Carcinoma, Hepatocellular Carcinoma, as well as treatment of for patients with solid tumors that have one of two specific genetic features known as mismatch repair deficiency and high microsatellite instability (irrespective of cancer type).

Extracellular adenosine has been known as an inhibitor of immune functions. While intracellular adenosine is involved in energy metabolism, nucleic acid metabolism, and the methionine cycle, extracellular adenosine plays an important role in intercellular signaling. Its signal is transmitted by G protein-coupled adenosine receptors on the cell surface, and it affects diverse physiological functions including neurological, cardiovascular, and immunological systems.

Tumors contain high levels of extracellular adenosine, suggesting that tumor cells may benefit from its immunosuppressive effect and catabolic energy production (Allard et al., Curr. Opin. Pharmacol., 2016, 29, 7-16; Otta A., Frontiers in Immunology, 2016, 7: 109). This high level of extracellular adenosine is probably due to overexpression of the enzyme CD73, which is responsible for production of extracellular adenosine. CD73 is overexpressed by a large number of tumors, with all the following tumors expressing medium or high levels of CD73 in >50% of tumor surface by immunohistochemistry (www.proteinatlas.org): Breast, Carcinoid, Cervical, Colorectal, Endometrial, Glioma, Head and Neck, Liver, Lung, Melanoma, Ovarian, Pancreatic, Prostate, Renal, Gastric, Thyroid, Urothelial.

Of the four known types of adenosine receptors, A2A adenosine receptor (A2AR) is the predominantly expressed subtype in most immune cells. Stimulation of A2AR generally provides an immunosuppressive signal that inhibits activities of T cells (proliferation, cytokine production, cytotoxicity), NK cells (cytotoxicity), NKT cells (cytokine production, CD40L upregulation), macrophages/dendritic cells (antigen presentation, cytokine production), and neutrophils (oxidative burst). The presence of high levels of extracellular adenosine in tumors was found to play a significant role in the evasion of antitumor immune response. Especially, it was shown that A2AR-deficient mice could spontaneously regress the inoculated tumor, whereas no wild-type mice showed similar tumor regression. A2AR antagonists were also beneficial in tumor-bearing wild-type animals. Importantly, depletion of T cells and NK cells impaired the retardation of tumor growth by A2AR antagonists, suggesting improvement of antitumor cellular immune response. Effector functions of T cells and NK cells are susceptible to A2AR stimulation. In addition, when activated in the presence of A2AR agonist, the effector function of T cells is persistently impaired even after removal of A2AR agonist. This result suggests that the adenosine-rich environment in tumors may induce T cells that are anergic to the tumor cells.

Therefore, given that A2A receptor is expressed in most immune cells and particularly effector immune cells such as T cells and NK cells and given that A2A receptor is engaged in tissues where adenosine is produced, it is thought that A2A inhibitors can be helpful in all the cancer indications.

Consequently, there is a need for A2A inhibitors able to restore immune functions in tumors environment.

Adenosine is known to be an endogenous modulator of a number of other physiological functions. For example, at the central nervous system (CNS) level, adenosine in known to induce sedative, anxiolytic and antiepileptic effects level.

Thus, A2A inhibitors were previously developed for the treatment of depression and neurodegenerative diseases such as Parkinson's disease or Alzheimer's disease (Pinna A., CNS Drugs, 2014, 28, 455). One of the most advanced A2A inhibitors developed for the treatment of CNS diseases is Preladenant (Hodgson R A et al., J. Pharmacol. Exp. Ther., 2009, 330(1), 294-303; Hauser R A et al., JAMA Neurol., 2015, 72(12), 1491-500).

However, such previously developed A2A inhibitors were designed to cross the blood brain barrier, in order to target A2A receptor in the CNS.

Given the higher level of adenosine in tumors when compared to the brain, much higher amounts of compounds will be needed to achieve the desired effect on immune functions restoration for treating cancers. Thus, in order to avoid deleterious side effects, one should provide A2A inhibitors which have a limited, if any, CNS penetrance, contrary to all previously developed A2A inhibitors.

The Applicant provided a series of non-brain penetrant A2A inhibitors in international patent application PCT/EP2018/058301, being thiocarbamate derivatives, which are useful to restore immune functions in tumor environment.

Nevertheless, these compounds present a very low solubility in aqueous buffers, a low intestinal solubility and thus a low oral bioavailability. Consequently, there is a need for a pharmaceutical formulation of these compounds that would be suitable for oral administration.

As evidenced in the experimental part below, the Applicant hereby provides a pharmaceutical composition that enables suitable oral bioavailability of the thiocarbamates A2A inhibitors.

Further, the anticancer effect of anticancer agents, such as for example immunotherapeutic agents, chemotherapeutic agents or antiangiogenic agents or combinations thereof, may remain insufficient. This is may be due, at least in part, to tumors immune escape mechanisms as those described above.

The specific combination of A2AR inhibitors (especially the thiocarbamate derivatives disclosed in WO2018/178338) with other anticancer agents has not been reported. Herein, the Applicant provides a combination comprising an adenosine A2A receptor inhibitor as disclosed in WO2018/178338 and another anticancer agent, for example an immunosuppressive agent such as a checkpoint inhibitor.

SUMMARY

This invention thus relates to a pharmaceutical composition comprising:
(a) a compound of Formula (I) as defined hereafter or a pharmaceutically acceptable salt or solvate thereof;

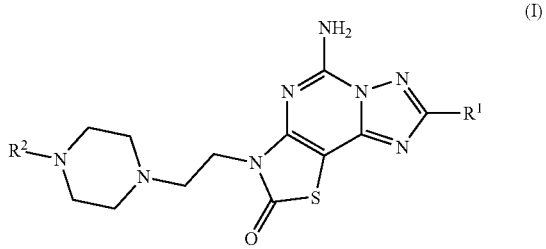

(b) a liquid carrier selected from lauroyl polyoxyl-32 glycerides, D-α-tocopherol-polyethylene glycol-1000 succinate and mixtures thereof; and
(c) optionally one or more other pharmaceutically acceptable carrier, diluent, excipient and/or adjuvant.

In one embodiment, the compound of Formula (I) is of the subformulae defined below, especially Formulae (Ia), (Ia-1), (Ia-la), (Ia-1b), (Ia-1c) or (Ia-1d). In one embodiment, the compound of Formula (I) is one of those listed in Table 1 below. In a specific embodiment, the compound of Formula (I) is selected from:
(R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one;
(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one;
and pharmaceutically acceptable salts or solvates thereof.

In one embodiment, the compound of Formula (I) is under the form of a salt, wherein the salt is the hydrochloride or esylate salt.

In one embodiment, the pharmaceutical composition of the invention further comprises PEG 400 and/or PEG 3350. In one embodiment, the pharmaceutical composition of the invention, further comprises caprylic acid.

In one embodiment, the pharmaceutical composition of the invention further comprises an antioxidant, which is may be for example butylated hydroxytoluene (BHT).

In one embodiment, the pharmaceutical composition of the invention further comprises a wetting agent; preferably the wetting agent is selected from sodium lauryl sulphate, vitamin E TPGS, sodium docusate, polysorbate 80 and poloxamer 407; more preferably the wetting agent is sodium lauryl sulphate.

In one embodiment, the pharmaceutical composition of the invention, further comprises a precipitation inhibitor; preferably the precipitation inhibitor is selected from hydroxypropylmethylcellulose, methylcellulose, polyvinylpyrrolidone, polyvinylpyrrolidone polyvinylacetate copolymer, polyvinyl caprolactam-polyvinyl acetate-polyethylene glycol graft copolymer and poloxamer 407; more preferably hydroxypropylmethylcellulose.

In one embodiment, in the pharmaceutical composition of the invention, the compound of Formula (I) is present in an amount ranging from 1% to 20% w/w, preferably from 5% to 15% w/w, more preferably about 10% w/w.

In one embodiment, in the pharmaceutical composition of the invention, the lipid carrier is present in an amount ranging from 55% to 99% w/w, preferably from 60% to 95% w/w, more preferably from 70% to 90% w/w.

In one embodiment, the pharmaceutical composition of the invention can be formulated as capsules, tablets or granules. In one embodiment, when the pharmaceutical composition of the invention is formulated as capsules, the capsule shells are constructed from gelatin and wherein additional components are optionally included in the capsule shells, such as for example polyethylene glycol and sodium lauryl sulphate.

The present invention further relates to a method of treating cancer, comprising administering to a patient in need thereof a therapeutically acceptable effective amount of a pharmaceutical composition according to the invention. In one embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers.

This invention thus relates to a combination comprising:
(a) at least one a compound of Formula (I):

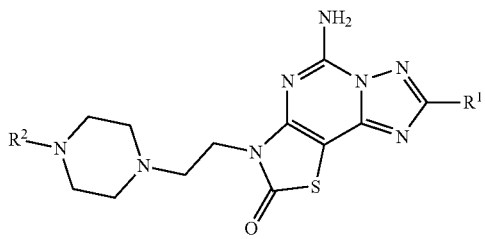

or a pharmaceutically acceptable salt or solvate thereof, wherein $R^1$ and $R^2$ are as defined below; and
(b) at least one anticancer agent.

In one embodiment, the compound of Formula (I) is of Formula (Ia), (Ia-1) or (Ia-1b) as defined below. In one embodiment, the compound of Formula (I) is one of those listed in Table 1 below.

In one embodiment, the anticancer agent is selected from immunotherapeutic agents, chemotherapeutic agents, anti-angiogenic agents, multidrug resistance-associated proteins inhibitors, radiotherapeutic agents, and any combination thereof.

In one embodiment, the immunotherapeutic agent is selected from checkpoint inhibitors, checkpoint agonists, IDO inhibitors, PI3K inhibitors, adenosine receptor inhibitors, adenosine-producing enzymes inhibitors, CD40 agonists, IL2 variants, immune cells, therapeutic vaccines, or any combination thereof.

In one embodiment, the checkpoint inhibitor is an inhibitor of a checkpoint protein selected from PD-1, PD-L1, CTLA-4 and TIGIT.

In one embodiment, the inhibitor of PD-1 is an anti-PD-1 antibody; the inhibitor of PD-L1 is an anti-PD-L1 antibody; the inhibitor of CTLA-4 is an anti-CTLA-4 antibody, and the inhibitor of TIGIT is an anti-TIGIT antibody.

In one embodiment, the chemotherapeutic agent is selected from anticancer alkylating agents, anticancer antimetabolites, anticancer antibiotics, plant-derived anticancer agents, anticancer platinum coordination compounds, Parp inhibitors, anti-hormone-sensitive cancer agents and any combination thereof. In one embodiment, the anticancer antibiotic is doxorubicin. In one embodiment, the anticancer platinum coordination compound is oxaliplatin. In one embodiment, the combination of chemotherapeutic agents is selected from (i) a combination consisting of folinic acid, fluorouracil and oxaliplatin; (ii) a combination consisting of carboplatin and paclitaxel; and (iii) a combination consisting of gemcitabine and nab-paclitaxel.

In one embodiment, the combination of the invention comprises at least one compound of Formula (I) as herein defined and at least two anticancer agents as herein defined.

The invention also relates to a pharmaceutical composition comprising:
(a) at least one compound of Formula (I) as herein defined; and
(b) at least one anticancer agent as herein defined.

The invention further relates to a kit of parts comprising:
(a) a first part comprising at least one compound of Formula (I) as herein defined; and
(b) a second part comprising at least one anticancer agent as herein defined.

In one embodiment, the combination, the pharmaceutical composition or the kit of parts according to the invention are for medical use.

In one embodiment, the combination, the pharmaceutical composition or the kit of parts according to the invention are for use in the treatment and/or prevention of cancer.

In one embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers.

In one embodiment, the constituents of the combination, or of the kit of parts according to the invention are to be administered to a patient in need thereof sequentially and/or concurrently.

In one embodiment, the constituents of the combination, or of the kit of parts according to the invention are to be administered to a patient in need thereof via different administration routes.

Definitions

In the present invention, the following terms have the following meanings:

The term "aldehyde" refers to a group —CHO.

The term "alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkenylcarbonyl" refers to a group —(C=O)-alkenyl wherein alkenyl is as herein defined.

The term "alkenylcarbonylamino" refers to a group —NH—(C=O)-alkenyl wherein alkenyl is as herein defined.

The term "alkoxy" refers to a group —O-alkyl wherein alkyl is as herein defined.

The term "alkyl" refers to a hydrocarbyl radical of formula $C_nH_{2n+1}$ wherein n is a number greater than or equal to 1. Generally, alkyl groups of this invention comprise from 1 to 8 carbon atoms, more preferably, alkyl groups of this invention comprise from 1 to 6 carbon atoms. Alkyl groups may be linear or branched. Suitable alkyl groups include methyl, ethyl, propyl, butyl, pentyl, hexyl, heptyl and octyl.

The term "alkylaminoalkyl" refers to a group -alkyl-NH-alkyl wherein alkyl is as herein defined.

The term "alkylaminoalkylaminocarbonyl" refers to a group —(C=O)—NH-alkyl-NH-alkyl wherein alkyl is as herein defined.

The term "(alkylaminoalkyl)(alkyl)aminocarbonyl" refers to a group —(C=O)—NR¹R² wherein R¹ is an alkyl group and R² is a -alkyl-NH-alkyl group, wherein alkyl is as herein defined.

The term "alkylaminoalkylcarbonyl" refers to a group —(C=O)-alkyl-NH-alkyl wherein alkyl is as herein defined.

The term "alkylcarbonyl" refers to a group —(C=O)-alkyl wherein alkyl is as herein defined.

The term "alkylheteroaryl" refers to any heteroaryl substituted by an alkyl group wherein alkyl is as herein defined.

The term "alkyloxycarbonyl" refers to a group —(C=O)—O-alkyl wherein alkyl is as herein defined.

The term "alkylsulfonyl" refers to a group —SO₂-alkyl wherein alkyl is as herein defined.

The term "alkylsulfonealkyl" refers to a group -alkyl-SO$_2$-alkyl wherein alkyl is as herein defined.

The term "alkylsulfonimidoyl" refers to a group —S(=O)(=NH)-alkyl wherein alkyl is as herein defined.

The term "alkylsulfoxide" refers to a group —(S=O)-alkyl wherein alkyl is as herein defined.

The term "alkylsulfoxidealkyl" refers to a group -alkyl-SO-alkyl wherein alkyl is as herein defined.

The term "alkyne" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkyl groups. Non-limiting examples of alkynyl groups are ethynyl, 2-propynyl, 2-butynyl, 3-butynyl, 2-pentynyl and its isomers, 2-hexynyl and its isomers-and the like.

The term "alkynealkyl" refers to a group -alkyl-alkyne wherein alkyl and alkyne are as herein defined.

The term "amino" refers to a group —NH$_2$.

The term "aminoalkyl" refers to a group -alkyl-NH$_2$ wherein alkyl is as herein defined.

The term "aminoalkylaminocarbonyl" refers to a group —(C=O)—NH-alkyl-NH$_2$ wherein alkyl is as herein defined.

The term "aminoalkylcarbonylamino" refers to a group —NH—(C=O)-alkyl-NH$_2$ wherein alkyl is as herein defined.

The term "aminocarbonyl" refers to a group —(C=O)—NH$_2$.

The term "(aminocarbonylalkyl)(alkyl)amino" refers to a group —NR$^1$R$^2$ wherein R$^1$ is an alkyl group and R$^2$ is a -alkyl-(C=O)—NH$_2$ group, wherein alkyl is as herein defined.

The term "aminocarbonylalkylamino" refers to a group —NH-alkyl-(C=O)—NH$_2$ wherein alkyl is as herein defined.

The term "aminosulfonyl" refers to a group —SO$_2$—NH$_2$.

The term "antioxidant" refers to an agent that diminishes or avoids the oxidation of other substances.

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 5 to 10; more preferably the aryl is a 5- or 6-membered aryl. Non-limiting examples of aryl comprise phenyl, naphthalenyl.

The term "carbonyl" refers to a group —(C=O)—.

The term "carbonylamino" refers to a group —NH—(C=O)—.

The term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms; still more preferably more preferably the cycloalkyl is a 5- or 6-membered cycloalkyl. Examples of cycloalkyl groups include but are not limited to cyclopropyl, cyclobutyl, cyclopentyl, cyclohexyl.

The term "cycloalkyloxy" refers to a group —O-cycloalkyl wherein cycloalkyl is as herein defined.

The term "dialkylamino" refers to a group —NR$^1$R$^2$ wherein R$^1$ and R$^2$ are both independently alkyl group as herein defined.

The term "dialkylaminoalkyl" refers to a group -alkyl-NR$^1$R$^2$ wherein R$^1$ and R$^2$ are both independently alkyl group, as herein defined.

The term "dialkylaminoalkylaminocarbonyl" refers to a group —(C=O)—NH-alkyl-NR$^1$R$^2$ wherein R$^1$ and R$^2$ are both alkyl group, as herein defined.

The term "dialkylaminoalkylcarbonyl" refers to a group —(C=O)-alkyl-NR$^1$R$^2$ wherein R$^1$ and R$^2$ are both alkyl group, as herein defined.

The term "dihydroxyalkyl" refers to a group alkyl is as herein defined substituted by two hydroxyl (—OH) groups.

The term "halo" or "halogen" refers to fluoro, chloro, bromo, or iodo.

The term "heteroaryl" refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: oxazolyl, thiazolyl, imidazolyl, furanyl and pyrrolyl. Preferably the heteroaryl is a 5- or 6-membered heteroaryl, more preferably the 5- or 6-membered heteroaryl is a furyl.

The term "heterocyclyl" refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Preferably the heterocyclyl is a 5- or 6-membered heterocyclyl. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, 1-oxido-1-thiomorpholin-4-yl, 1-dioxido-1-thiomorpholin-4-yl, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "heterocyclylalkylaminocarbonyl" refers to a group —(C=O)—NH-alkyl-heterocyclyl, wherein alkyl and heterocyclyl are as herein defined.

The term "(heterocyclyl)(alkyl)aminoalkyl" refers to a group -alkyl-NR$^1$R$^2$ wherein R$^1$ is an alkyl group and R$^2$ is a heterocyclyl group, wherein alkyl and heterocyclyl are as herein defined.

The term "heterocyclylcarbonyl" refers to a group —(C=O)-heterocyclyl wherein heterocyclyl is as herein defined.

The term "heterocyclylalkyl" refers to a group -alkyl-heterocyclyl wherein alkyl and heterocyclyl are as herein defined.

The term "heterocyclyloxy" to a group —O-heterocyclyl wherein heterocyclyl is as herein defined.

The term "heterocyclylsulfonyl" refers to a group —SO$_2$-heterocyclyl wherein heterocyclyl is as herein defined.

The term "hydroxyalkyl" refers to a group -alkyl-OH wherein alkyl is as herein defined.

The term "hydroxyalkylaminoalkyl" refers to a group -alkyl-NH-alkyl-OH wherein alkyl is as herein defined.

The term "hydroxycarbonyl" refers to a group —C(=O)—OH wherein carbonyl is as herein defined. In other words, "hydroxycarbonyl" corresponds to a carboxylic acid group.

The term "oxo" refers to a =O substituent.

The term "sulfonylamino" refers to a group —NH—SO$_2$.

The term "about", preceding a figure encompasses plus or minus 10%, or less (such as plus or less 1%), of the value of said figure. It is to be understood that the value to which the term "about" refers is itself also specifically, and preferably, disclosed.

The term "administration", or a variant thereof (e.g. "administering"), means providing the active agent or active ingredient (e.g. an A2AR inhibitor or an anticancer agent), alone or as part of a pharmaceutically acceptable composition, to the patient in whom/which the condition, symptom, or disease is to be treated or prevented.

The term "autologous" refers to any material derived from the same individual to whom it is later to be re-introduced.

The term "allogenic" refers to any material derived from a different individual of the same specie as the individual to whom the material is introduced. Two or more individuals are said to be allogenic to one another when the genes at one or more loci are not identical.

In some aspects, allogenic material from individuals of the same species may be sufficiently unlike genetically to interact antigenically.

The terms "IC$_{50}$" or "half maximal inhibitory concentration" represent the concentration of an inhibitor that is required for 50% inhibition in vitro.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "A2AR inhibitor" refers to a compound that has a biological effect to inhibit or significantly reduce or down-regulate the biological activity of A2A receptor.

The term "human" refers to a subject of both genders and at any stage of development (i.e. neonate, infant, juvenile, adolescent, adult).

The term "patient" refers to a warm-blooded animal or a mammal, more preferably a human, who/which is awaiting the receipt of, or is receiving medical care or is/will be the object of a medical procedure.

The expression "pharmaceutically acceptable" refers to the ingredients of a pharmaceutical composition are compatible with each other and not deleterious to the subject to which it is administered.

The expression "pharmaceutically acceptable carrier, diluent, excipient and/or adjuvant" refers to a substance that does not produce an adverse, allergic or other untoward reaction when administered to an animal, preferably a human. It includes any and all inactive substances such as for example solvents, cosolvents, antioxidants, surfactants, stabilizing agents, emulsifying agents, buffering agents, pH modifying agents, preserving agents (or preservating agents), antibacterial and antifungal agents, isotonifiers, granulating agents or binders, lubricants, disintegrants, glidants, diluents or fillers, adsorbents, dispersing agents, suspending agents, coating agents, bulking agents, release agents, absorption delaying agents, sweetening agents, flavoring agents and the like. For human administration, preparations should meet sterility, pyrogenicity, general safety and purity standards as required by regulatory offices, such as, e.g., FDA Office or EMA.

The term "predrug", as used herein, means any compound that will be modified to form a drug species, wherein the modification may take place either inside or outside of the body, and either before or after the predrug reaches the area of the body where administration of the drug is indicated.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "prodrug" as used herein means the pharmacologically acceptable derivatives of compounds of Formula (I), such as for example esters or amides, whose in vivo biotransformation product generates the biologically active drug. Prodrugs are generally characterized by increased bio-availability and are readily metabolized into biologically active compounds in vivo.

The terms "therapeutically effective amount" or "therapeutically effective dose" refer to the amount or dose of active ingredient that is aimed at, without causing significant negative or adverse side effects to the subject, (1) delaying or preventing the onset of a cancer in the subject; (2) reducing the severity or incidence of a cancer; (3) slowing down or stopping the progression, aggravation, or deterioration of one or more symptoms of a cancer affecting the subject; (4) bringing about ameliorations of the symptoms of a cancer affecting the subject; or (5) curing a cancer affecting the subject. A therapeutically effective amount may be administered prior to the onset of a cancer for a prophylactic or preventive action. Alternatively, or additionally, a therapeutically effective amount may be administered after initiation of a cancer for a therapeutic action.

The terms "treating" or "treatment" refer to therapeutic treatment; wherein the object is to prevent or slow down the targeted pathologic condition or disease. A subject or mammal is successfully "treated" for a disease or affection or condition if, after receiving the treatment according to the present invention, the subject or mammal shows observable and/or measurable reduction in or absence of one or more of the following: reduction of the number of cancer cells; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "subject" refers to a mammal, preferably a human. In one embodiment, the subject is diagnosed with a cancer. In one embodiment, the subject is a patient, preferably a human patient, who/which is awaiting the receipt of, or is receiving, medical care or was/is/will be the subject of a medical procedure or is monitored for the development or progression of a disease, such as a cancer. In one embodiment, the subject is a human patient who is treated and/or monitored for the development or progression of a cancer. In one embodiment, the subject is a male. In another embodiment, the subject is a female. In one embodiment, the subject is an adult. In another embodiment, the subject is a child. The terms "tumor-specific antigen" or "tumor-associated antigen" refer to an antigen specifically and/or abundantly expressed by cancer cells or tumor cells. T cells expressing T cell receptors recognizing and binding said antigens may be referred to as T cells recognizing a tumor-specific or tumor-associated antigen, T cells specific for a tumor-specific or tumor-associated antigen, T cells specific of a tumor-specific or tumor-associated antigen, or T cells directed to a tumor-specific or tumor-associated antigen. The term "vaccine" refers to a preparation comprising a substance or a group of substances (i.e., a vaccine) meant to induce and/or enhance in a subject a targeted immune response towards an infectious agent (such as viruses, bacteria, fungi or parasites) or towards cancer cells. Prophylactic vaccination is used to prevent a subject from ever having a particular disease or to only have a mild case of the disease. Therapeutic vaccination is intended to treat a particular disease in a subject. For example, therapeutic anticancer vaccines may comprise a tumor-associated antigen or tumor-associated antigens, aiming at inducing and/or enhancing a cell-mediated immune response, in particular a T cell immune response, directed towards the cancer cells expressing said tumor-associated antigen(s).

DETAILED DESCRIPTION

A2AR Inhibitor

The present invention relates to pharmaceutical compositions and combinations of anticancer agents comprising at least one A2A adenosine receptor (A2AR) inhibitor. The A2AR inhibitor is a thiocarbamate derivative, especially a thiocarbamate derivative as those disclosed in PCT/EP2018/058301. More preferably the A2AR inhibitor is a thiocarbamate derivative of formula (I) as described below.

In one embodiment, the thiocarbamate derivative A2AR inhibitor is of Formula (I):

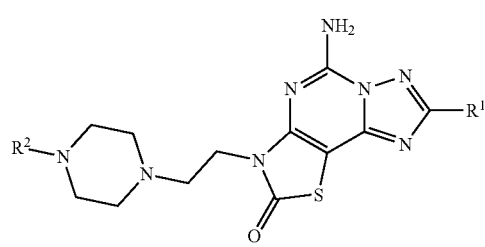

or a pharmaceutically acceptable salt or solvate thereof, wherein:
$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$R^2$ represents 6-membered aryl or 6-membered heteroaryl,
wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;
said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;
or the heteroaryl or aryl groups are optionally substituted with two substituents that form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred compounds of Formula (I) are of Formula (Ia):

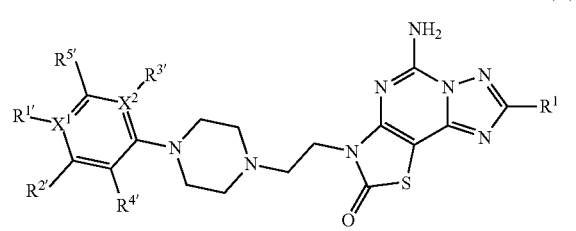

or a pharmaceutically acceptable salt or solvate thereof, wherein:

$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$X^1$ and $X^2$ represent each independently C or N;

$R^{1'}$ is absent when $X^1$ is N; or when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or $R^{1'}$ and $R^{2'}$ form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

In one specific embodiment of the invention, $R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro). In a preferred embodiment, $R^1$ represents 5-membered heteroaryl; more preferably, $R^1$ represents furyl.

In one specific embodiment of the invention, $X^1$ and $X^2$ represent each independently C or N. In another specific embodiment, $X^1$ and $X^2$ both represent C.

In one specific embodiment of the invention, $R^{1'}$ is absent when $X^1$ is N.

In another specific embodiment, when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{1'}$ substituents are optionally substituted by one or more substituent selected from halo, hydroxy, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkoxy, amino, dialkylamino, aminoalkylcarbonylamino, aminocarbonylalkylamino, heterocyclylalkylaminocarbonyl, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl) aminocarbonyl, heterocyclylcarbonyl, alkylsulfoxide and alkylsulfonealkyl.

In one specific embodiment of the invention, $R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{2'}$ substituents are optionally substituted by one or more substituent selected from oxo, halo, hydroxy, cyano, alkyl, heterocyclylalkyl, dihydroxyalkyl, dialkylaminoalkyl, heteroaryl, alkylheteroaryl, hydroxycarbonyl, alkyloxycarbonyl, aminocarbonyl, heterocyclylalkylaminocarbonyl, alkylaminoalkylcarbonyl, dialkylaminoalkylcarbonyl, alkylsulfoxide, alkylsulfonealkyl.

In another specific embodiment of the invention, $R^{1'}$ and $R^{2'}$ form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, $R^{3'}$ is absent when $X^2$ is N. In another specific embodiment of the invention, when $X^2$ is C, $R^{3'}$ represents H or halo. In a preferred embodiment, when $X^2$ is C, $R^{3'}$ represents H or F.

In one specific embodiment of the invention, $R^{4'}$ represents H or halo. In a preferred embodiment, $R^{4'}$ represents H or F.

In one specific embodiment of the invention, $R^{5'}$ represents H or halo. In a preferred embodiment, $R^{5'}$ represents H or F.

In one embodiment, preferred compounds of Formula (Ia) are those of Formula (Ia-1):

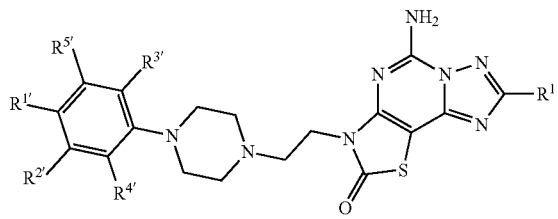

(Ia-1)

or a pharmaceutically acceptable salt or solvate thereof, wherein $R^1$, $R^{1'}$, $R^{2'}$, $R^{3'}$, $R^{4'}$ and $R^5$ are as defined in Formula (Ia).

In one embodiment, preferred compounds of Formula (Ia-1) are those of Formula (Ia-1a):

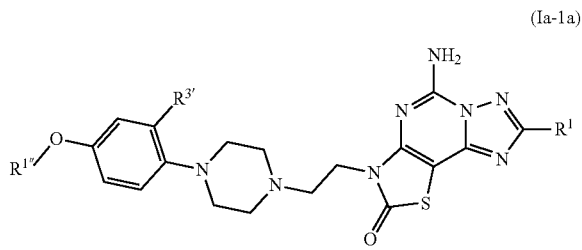

(Ia-1a)

or a pharmaceutically acceptable salt or solvate thereof, wherein:
$R^1$ and $R^{3'}$ are as defined in Formula (Ia); and
$R^{1''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, $R^{1''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{1'''}$ represents an alkyl or heterocyclyl group substituted by one or more group selected from hydroxy, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, heterocyclylcarbonyl, alkylsulfoxide, alkylsulfonealkyl.

In one embodiment, preferred compounds of Formula (Ia-1) are those of Formula (Ia-1b):

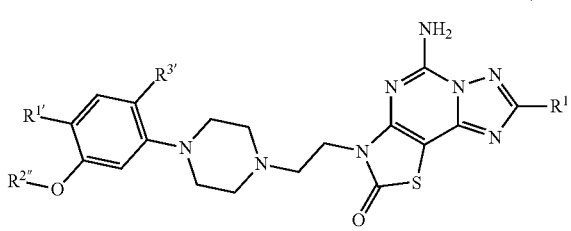

(Ia-1b)

or a pharmaceutically acceptable salt or solvate thereof, wherein:
$R^1$ and $R^{3'}$ are as defined in Formula (Ia);
$R^{1'}$ represents H or halo, preferably H or F; and
$R^{2'''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one specific embodiment of the invention, $R^{1'}$ represents H or halo. In a preferred embodiment, $R^{1'}$ represents H or F.

In one specific embodiment of the invention, $R^{2'''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{2'''}$ represents an alkyl or heterocyclyl group substituted by one or more group selected from hydroxy, cyano, heteroaryl, alkylheteroaryl, alkyne, hydroxycarbonyl, alkyloxycarbonyl, aminocarbonyl, alkylaminoalkylcarbonyl, dialkylaminoalkylcarbonyl, alkylsulfoxide, alkylsulfonealkyl.

In one embodiment, preferred compounds of Formula (Ia-1) are those of Formula (Ia-1c) or (Ia-1d):

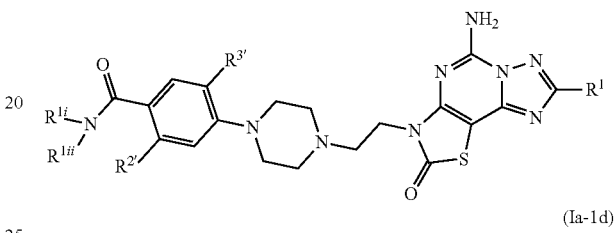

(Ia-1c)

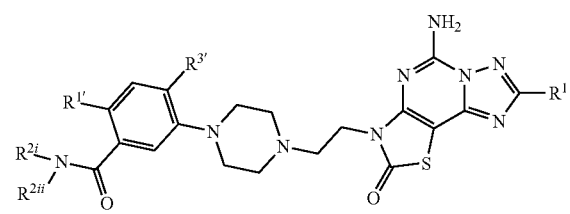

(Ia-1d)

or a pharmaceutically acceptable salt or solvate thereof, wherein:
$R^1$ and $R^{3'}$ are as defined in Formula (Ia);
$R^{1'}$ represents H or halo, preferably H or F;
$R^{2'}$ represents H or halo, preferably H or F;
$R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl; and
$R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In one specific embodiment of the invention, $R^{1'}$ represents H or halo. In a preferred embodiment, $R^{1'}$ represents H or F.

In one specific embodiment of the invention, $R^{2'}$ represents H or halo. In a preferred embodiment, $R^{2'}$ represents H or F.

In one specific embodiment of the invention, $R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In a preferred embodiment, $R^{1i}$ and $R^{1ii}$ represent each independently hydrogen, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl or heterocyclylalkylaminocarbonyl.

In one specific embodiment of the invention, $R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In a preferred embodiment, $R^{2i}$ and $R^{2ii}$ represent each independently hydrogen, alkyl, heterocyclylalkyl, dihydroxyalkyl, dialkylaminoalkyl or heterocyclylalkylaminocarbonyl. In a preferred embodiment, $R^{2i}$ and $R^{2ii}$ represent each independently hydrogen, alkyl or dialkylaminoalkyl.

In one embodiment, preferred compounds of Formula (Ia) are those of Formulae (Ia-2) or (Ia-3):

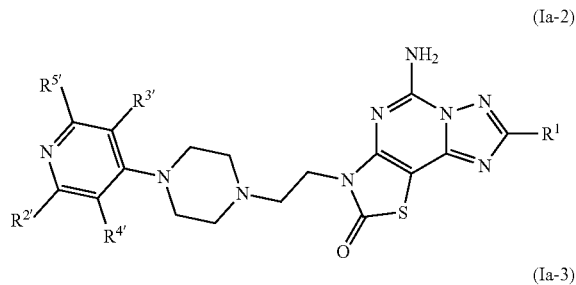

(Ia-2)

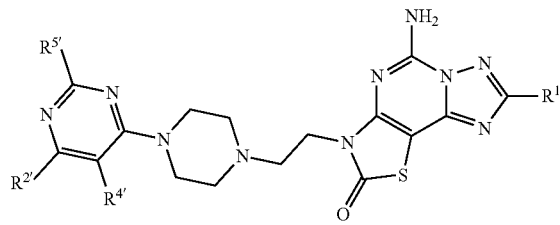

(Ia-3)

or a pharmaceutically acceptable salt or solvate thereof, wherein $R^1$, $R^{2'}$, $R^{3'}$, $R^{4'}$ and $R^{5'}$ are as defined in Formula (Ia).

Particularly preferred compounds of Formula (I) of the invention are those listed in Table 1 hereafter.

TABLE 1

| Cpd n° | Structure | Chemical name | MW |
|---|---|---|---|
| 1 | 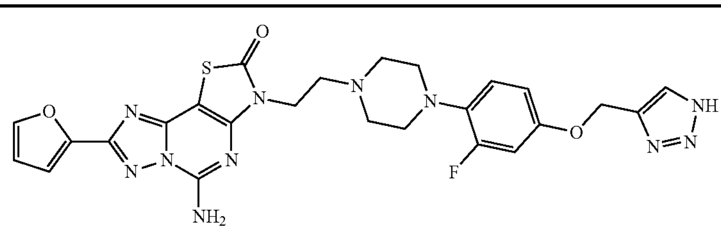 | 3-(2-(4-(4-(4-((1H-1,2,3-triazolo-4yl)methoxy-2fluorophenyl)piperazine-1-yl)ethyl)-5-amino-(8-(furan-2-yl)thiazolo[5,4-e][1,2,4]triazolo[1,5-c]pyrimidine-2(3H)-one | 577.60 |
| 2 | 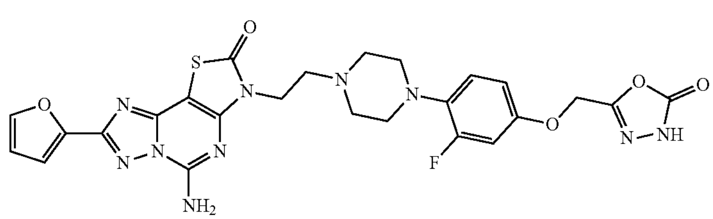 [SMILES: Nc1nc2c(sc(=O)n2CCN2CCN(c3ccc(OCc4n[nH]c(=O)o4)cc3F)CC2)c2nc(-c3ccco3)nn12] | 5-((4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)methyl)-1,3,4-oxadiazol-2(3H)-one | 594.58 |

TABLE 1-continued

| Cpd n° | Structure | Chemical name | MW |
|---|---|---|---|
| 3 | 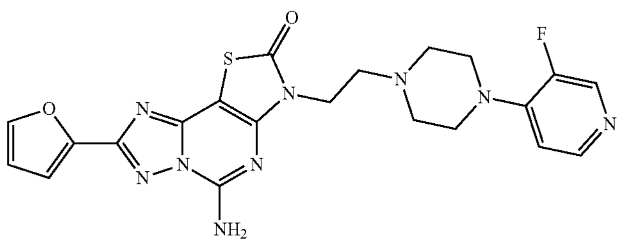 [SMILES: Nc1nc2c(sc(=O)n2CCN2CCN(c3ccncc3F)CC2)c2nc(-c3ccco3)nn12] | 5-amino-3-(2-(4-(3-fluoropyridin-4-yl)piperazin-1-yl)ethyl)-8-(furan-2-yl)thiazolo[5,4-e][1,2,4]triazolo[1,5-c]pyrimidin-2(3H)-one | 481.51 |
| 4 | 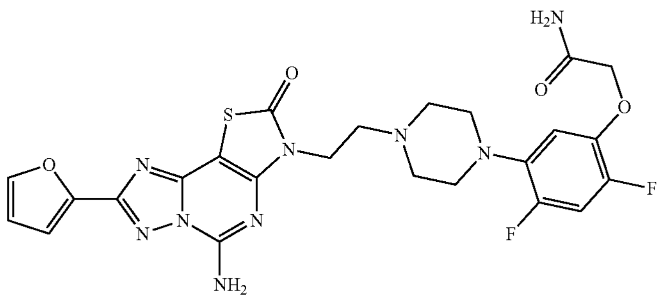 [SMILES: NC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)acetamide | 571.56 |
| 5 | 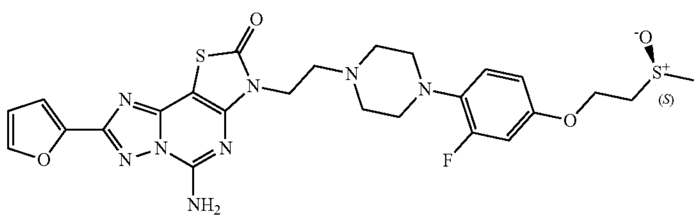 | (S)-5-amino-3-(2-(4-(2-fluoro-4-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 586.66 |
| 6 | 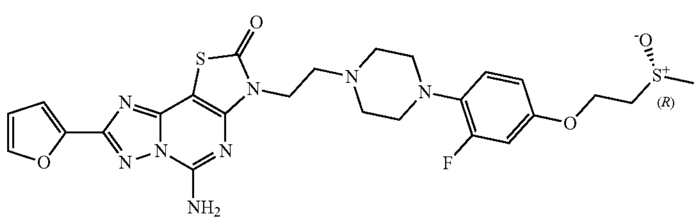 | (R)-5-amino-3-(2-(4-(2-fluoro-4-(2-(methylsulfinyl)ethoxy)phenyl)-piperazin-1-yl)ethyl)-8-(furan-2-yl)thiazolo[5,4-e][1,2,4]triazolo[1,5-c]pyrimidin-2(3H)-one | 586.66 |
| 7 | 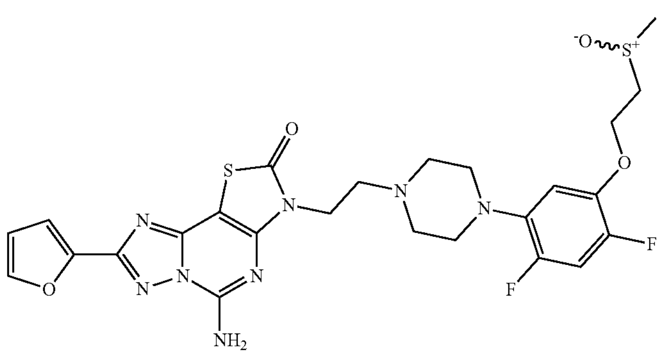 | (R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |

TABLE 1-continued

| Cpd n° | Structure | Chemical name | MW |
|---|---|---|---|
| 8a | 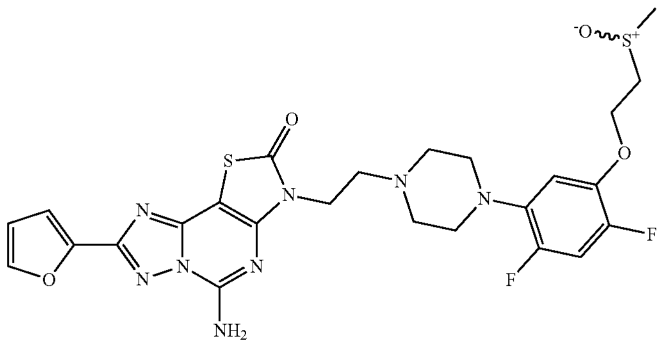 | (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |
| 8b | 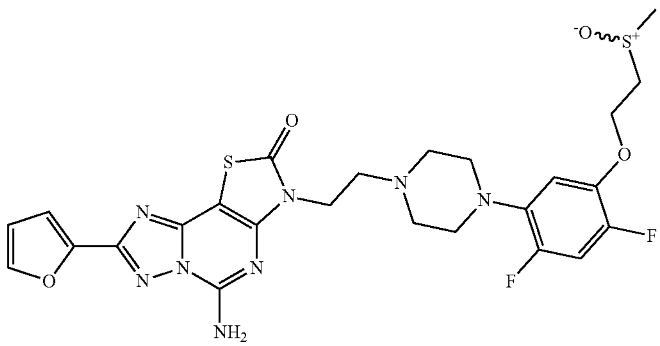 | (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |
| 9 | 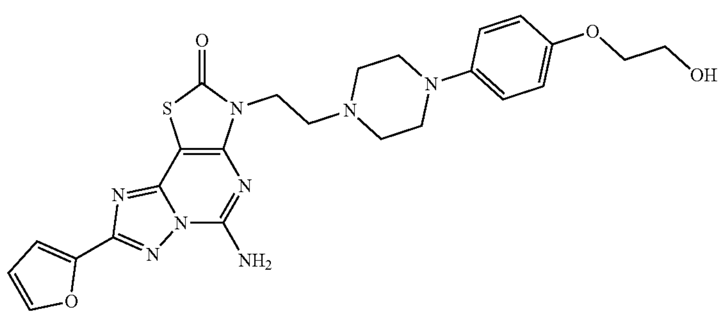 [SMILES: Nc1nc2c(sc(=O)n2CCN2CCN(c3ccc(OCCO)cc3)CC2)c2nc(-c3ccco3)nn12] | 5-amino-8-(furan-2-yl)-3-(2-(4-(4-(2-hydroxyethoxy)phenyl)piperazin-1-yl)ethyl)thiazolo[5,4-e][1,2,4]triazolo[1,5-c]pyrimidin-2(3H)-one | 522.58 |
| 10 | 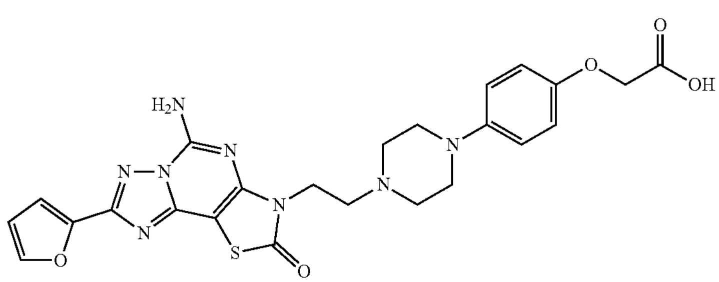 [SMILES: Nc1nc2c(sc(=O)n2CCN2CCN(c3ccc(OCC(=O)O)cc3)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)phenoxy)acetic acid | 536.56 |
| 11 | 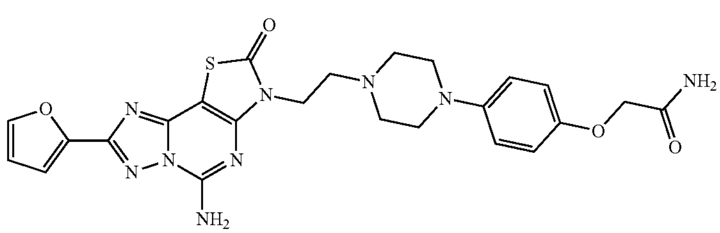 [SMILES: NC(=O)COc1ccc(N2CCN(CCn3c(=O)sc4c3nc(N)n3nc(-c5ccco5)nc43)CC2)cc1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)phenoxy)acetamide | 535.58 |

TABLE 1-continued

| Cpd n° | Structure | Chemical name | MW |
|---|---|---|---|
| 12 | 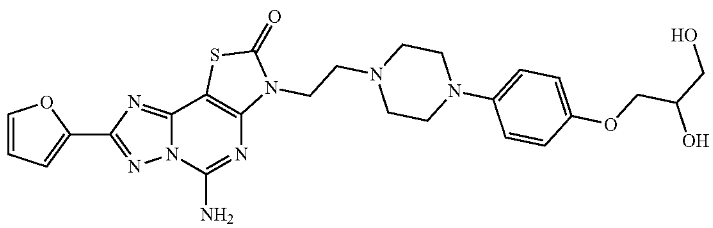 [SMILES: Nc1nc2c(sc(=O)n2CCN2CCN(c3ccc(OCC(O)CO)cc3)CC2)c2nc(-c3ccco3)nn12] | 5-amino-3-(2-(4-(4-(2,3-dihydroxypropoxy)phenyl)piperazin-1-yl)ethyl)-8-(furan-2-yl)thiazolo[5,4-e][1,2,4]triazolo[1,5-c]pyrimidin-2(3H)-one | 552.61 |
| 13 | 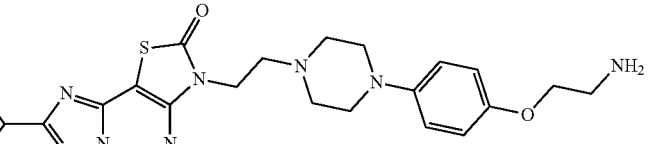 | 5-amino-3-(2-(4-(4-(2-aminoethoxy)phenyl)piperazin-1-yl)ethyl)-8-(furan-2-yl)thiazolo[5,4-e][1,2,4]triazolo[1,5-c]pyrimidin-2(3H)-one | 521.60 |
| 14 | 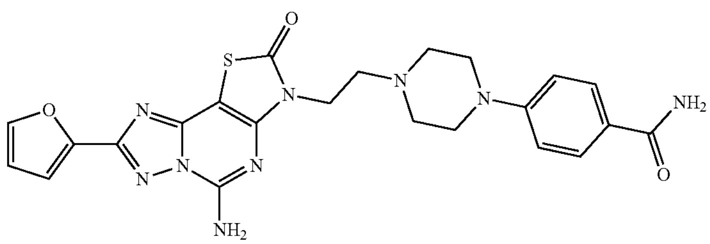 [SMILES: NC(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide | 505.55 |
| 15 | 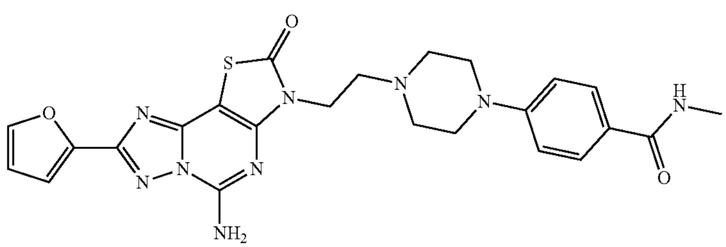 [SMILES: CNC(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzamide | 519.58 |
| 16 | 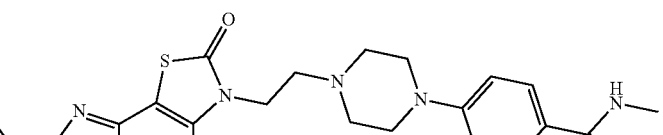 | 5-amino-8-(furan-2-yl)-3-(2-(4-(4-(2-morpholinoethoxy)phenyl)piperazin-1-yl)ethyl)thiazolo[5,4-e][1,2,4]triazolo[1,5-c]pyrimidin-2(3H)-one | 591.68 |
| 17 | 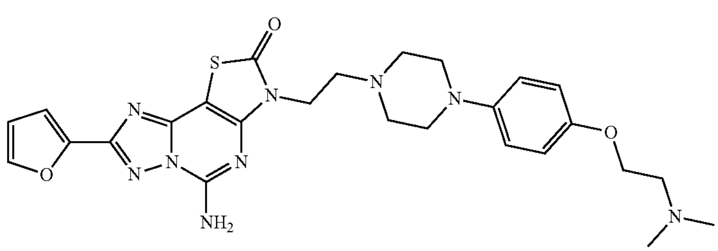 [SMILES: CN(C)CCOc1ccc(N2CCN(CCn3c(=O)sc4c3nc(N)n3nc(-c5ccco5)nc43)CC2)cc1] | 5-amino-3-(2-(4-(4-(2-(dimethylamino)ethoxy)phenyl)piperazin-1-yl)ethyl)-8-(furan-2-yl)thiazolo[5,4-e][1,2,4]triazolo[1,5-c]pyrimidin-2(3H)-one | 549.65 |

TABLE 1-continued

| Cpd n° | Structure | Chemical name | MW |
|---|---|---|---|
| 18 | 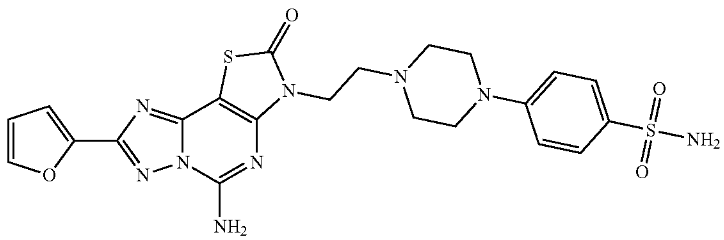 [SMILES: Nc1nc2c(sc(=O)n2CCN2CCN(c3ccc(S(N)(=O)=O)cc3)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzenesulfonamide | 541.61 |
| 19 | 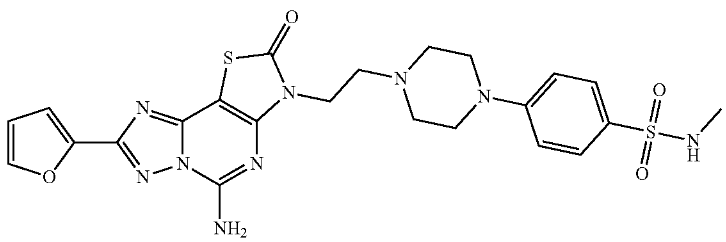 [SMILES: CNS(=O)(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzenesulfonamide | 555.63 |
| 20 | 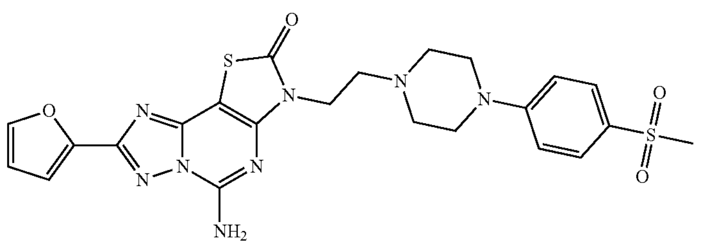 [SMILES: CS(=O)(=O)c1ccc(N2CCN(CCn3c(=O)sc4c3nc(N)n3nc(-c5ccco5)nc43)CC2)cc1] | 5-amino-8-(furan-2-yl)-3-(2-(4-(4-(methylsulfonyl)phenyl)piperazin-1-yl)ethyl)thiazolo[5,4-e][1,2,4]triazolo[1,5-c]pyrimidin-2(3H)-one | 540.62 |
| 21 | 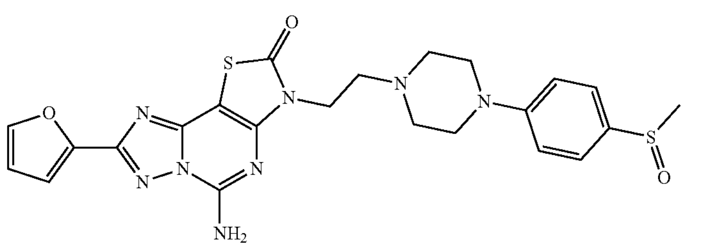 [SMILES: CS(=O)c1ccc(N2CCN(CCn3c(=O)sc4c3nc(N)n3nc(-c5ccco5)nc43)CC2)cc1] | 5-amino-8-(furan-2-yl)-3-(2-(4-(4-(methylsulfinyl)phenyl)piperazin-1-yl)ethyl)thiazolo[5,4-e][1,2,4]triazolo[1,5-c]pyrimidin-2(3H)-one | 524.62 |
| 22 | 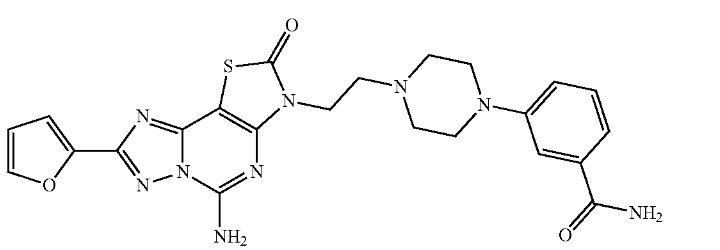 [SMILES: NC(=O)c1cccc(N2CCN(CCn3c(=O)sc4c3nc(N)n3nc(-c5ccco5)nc43)CC2)c1] | 3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide | 505.55 |
| 23 | 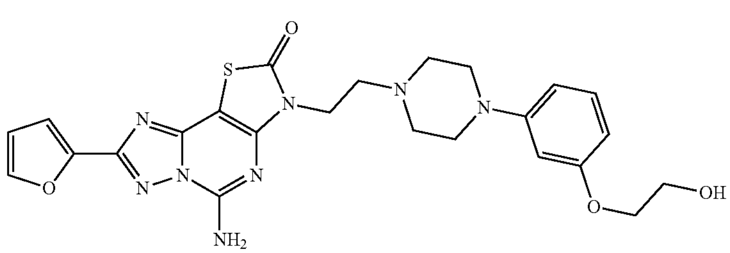 [SMILES: Nc1nc2c(sc(=O)n2CCN2CCN(c3cccc(OCCO)c3)CC2)c2nc(-c3ccco3)nn12] | 5-amino-8-(furan-2-yl)-3-(2-(4-(3-(2-hydroxyethoxy)phenyl)piperazin-1-yl)ethyl)thiazolo[5,4-e][1,2,4]triazolo[1,5-c]pyrimidin-2(3H)-one | 522.58 |

TABLE 1-continued

| Cpd n° | Structure | Chemical name | MW |
|---|---|---|---|
| 24 | 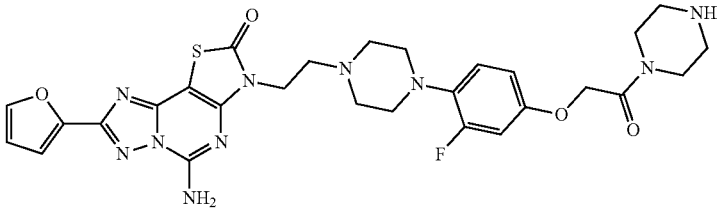 [SMILES: Nc1nc2c(sc(=O)n2CCN2CCN(c3ccc(OCC(=O)N4CCNCC4)cc3F)CC2)c2nc(-c3ccco3)nn12] | 5-amino-3-(2-(4-(2-fluoro-4-(2-oxo-2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one | 622.67 |
| 25 | 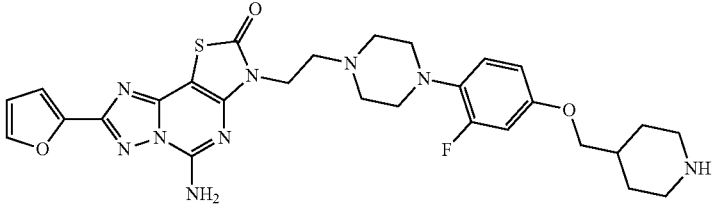 [SMILES: Nc1nc2c(sc(=O)n2CCN2CCN(c3ccc(OCC4CCNCC4)cc3F)CC2)c2nc(-c3ccco3)nn12] | 5-amino-3-(2-(4-(2-fluoro-4-(piperidin-4-ylmethoxy)phenyl)piperazin-1-yl)ethyl)-8-(furan-2-yl)thiazolo[5,4-e][1,2,4]triazolo[1,5-c]pyrimidin-2(3H)-one | 593.68 |
| 26 | 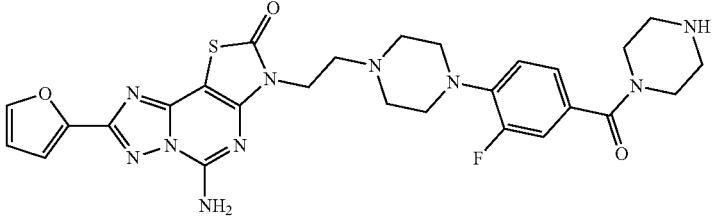 [SMILES: Nc1nc2c(sc(=O)n2CCN2CCN(c3ccc(C(=O)N4CCNCC4)cc3F)CC2)c2nc(-c3ccco3)nn12] | 5-amino-3-(2-(4-(2-fluoro-4-(piperazine-1-carbonyl)phenyl)piperazin-1-yl)ethyl)-8-(furan-2-yl)thiazolo[5,4-e][1,2,4]triazolo[1,5-c]pyrimidin-2(3H)-one | 592.65 |
| 27 | 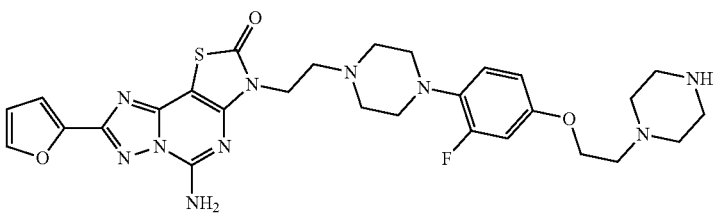 [SMILES: Nc1nc2c(sc(=O)n2CCN2CCN(c3ccc(OCCN4CCNCC4)cc3F)CC2)c2nc(-c3ccco3)nn12] | 5-amino-3-(2-(4-(2-fluoro-4-(2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one | 608.69 |
| 28 | 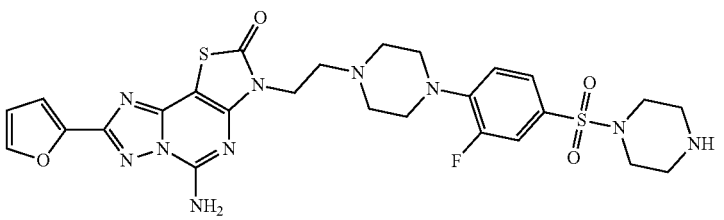 [SMILES: Nc1nc2c(sc(=O)n2CCN2CCN(c3ccc(S(=O)(=O)N4CCNCC4)cc3F)CC2)c2nc(-c3ccco3)nn12] | 5-amino-3-(2-(4-(2-fluoro-4-(piperazin-1-ylsulfonyl)phenyl)piperazin-1-yl)ethyl)-8-(furan-2-yl)thiazolo[5,4-e][1,2,4]triazolo[1,5-c]pyrimidin-2(3H)-one | 628.70 |
| 29 | 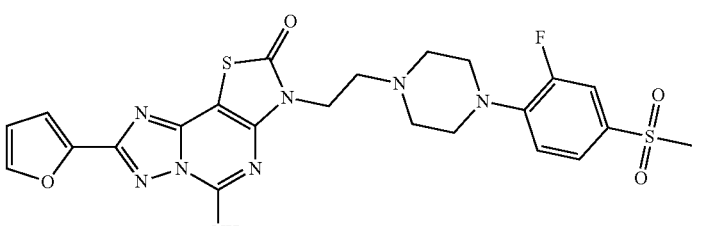 | 5-amino-3-(2-(4-(2-fluoro-4-(methylsulfonyl)phenyl)piperazin-1-yl)ethyl)-8-(furan-2-yl)thiazolo[5,4-e][1,2,4]triazolo[1,5-c]pyrimidin-2(3H)-one | 558.61 |
| 30 | 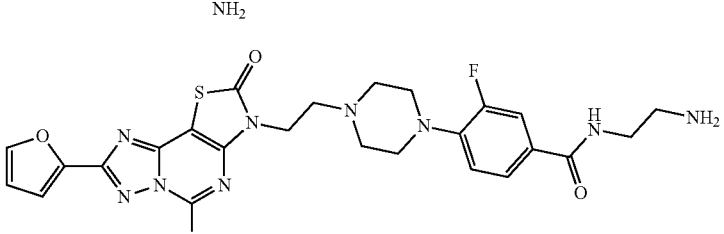 | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-aminoethyl)-3-fluorobenzamide | 566.61 |

TABLE 1-continued

| Cpd n° | Structure | Chemical name | MW |
|---|---|---|---|
| 31 | 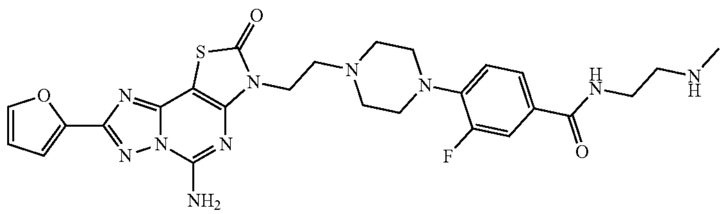 [SMILES: CNCCNC(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylamino)ethyl)benzamide | 580.64 |
| 32 | 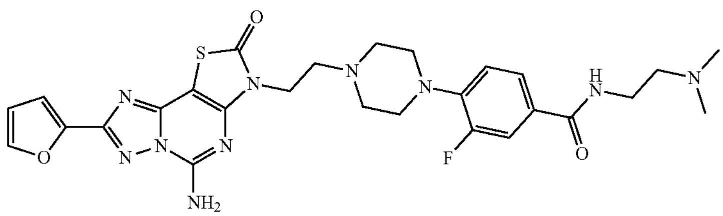 [SMILES: CN(C)CCNC(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluorobenzamide | 594.66 |
| 33 | 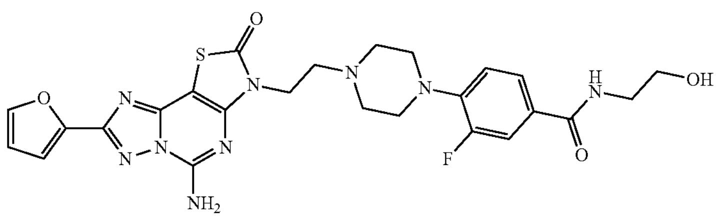 [SMILES: Nc1nc2c(sc(=O)n2CCN2CCN(c3ccc(C(=O)NCCO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-hydroxyethyl)benzamide | 567.60 |
| 34 | 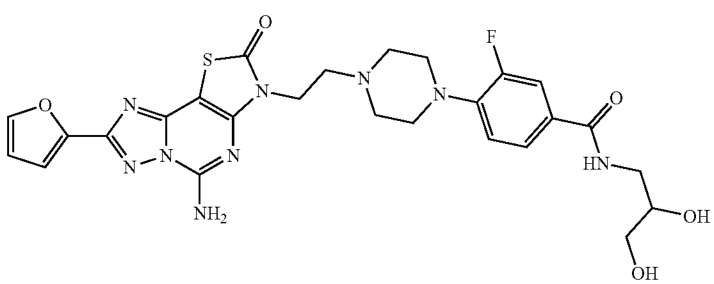 [SMILES: Nc1nc2c(sc(=O)n2CCN2CCN(c3ccc(C(=O)NCC(O)CO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-3-fluorobenzamide | 597.62 |
| 35 | 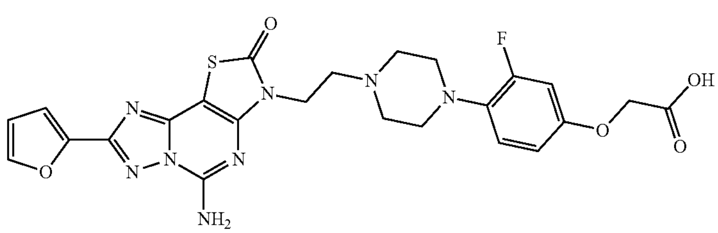 [SMILES: Nc1nc2c(sc(=O)n2CCN2CCN(c3ccc(OCC(=O)O)cc3F)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetic acid | 554.55 |
| 36 | 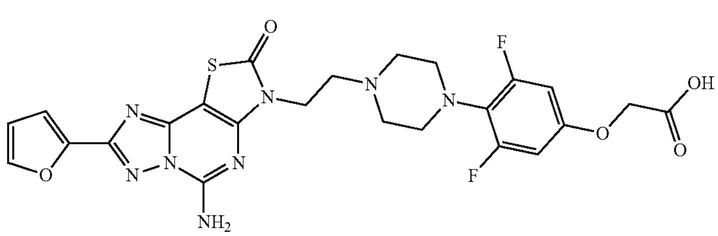 [SMILES: Nc1nc2c(sc(=O)n2CCN2CCN(c3c(F)cc(OCC(=O)O)cc3F)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3,5-difluorophenoxy) acetic acid | 572.54 |

TABLE 1-continued

| Cpd n° | Structure | Chemical name | MW |
|---|---|---|---|
| 37 | 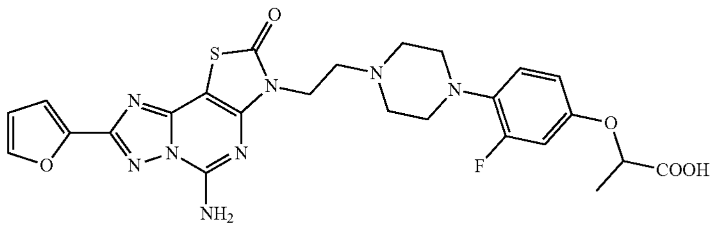 | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 38 | 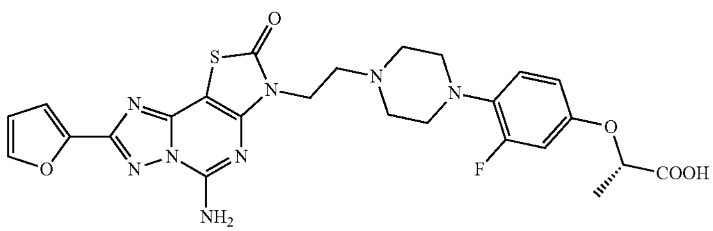 [SMILES: C[C@H](Oc1ccc(N2CCN(CCn3c(=O)sc4c3nc(N)n3nc(-c5ccco5)nc43)CC2)c(F)c1)C(=O)O] | (S)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 39 | 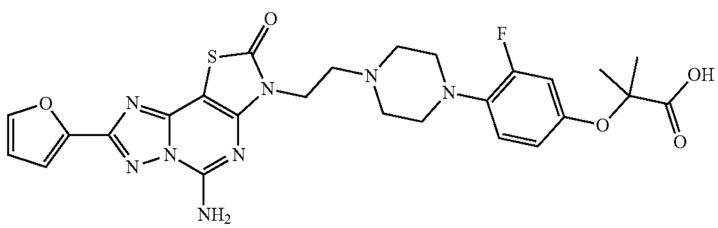 [SMILES: CC(C)(Oc1ccc(N2CCN(CCn3c(=O)sc4c3nc(N)n3nc(-c5ccco5)nc43)CC2)c(F)c1)C(=O)O] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-2-methylpropanoic acid | 582.61 |
| 40 | 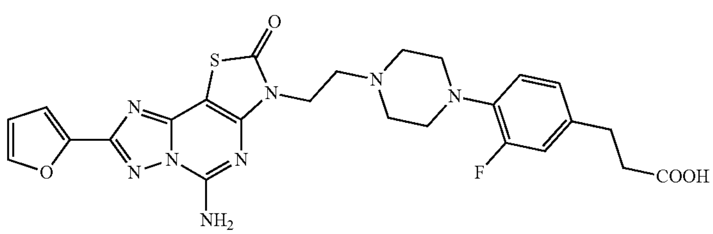 [SMILES: Nc1nc2c(sc(=O)n2CCN2CCN(c3ccc(CCC(=O)O)cc3F)CC2)c2nc(-c3ccco3)nn12] | 3-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenyl)propanoic acid | 552.58 |
| 41 | 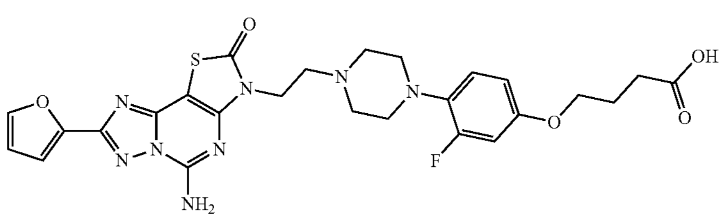 [SMILES: Nc1nc2c(sc(=O)n2CCN2CCN(c3ccc(OCCCC(=O)O)cc3F)CC2)c2nc(-c3ccco3)nn12] | 4-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)butanoic acid | 582.61 |
| 42 | 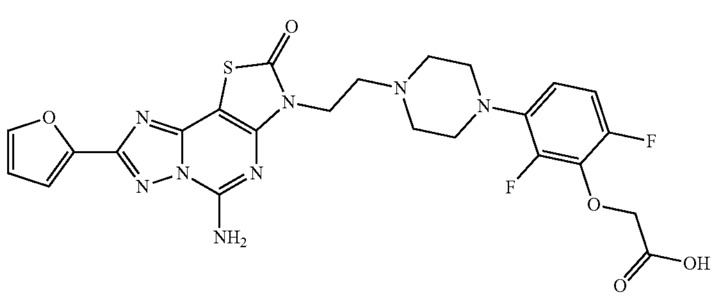 [SMILES: Nc1nc2c(sc(=O)n2CCN2CCN(c3ccc(F)c(OCC(=O)O)c3F)CC2)c2nc(-c3ccco3)nn12] | 2-(3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,6-difluorophenoxy) acetic acid | 572.54 |

TABLE 1-continued

| Cpd n° | Structure | Chemical name | MW |
|---|---|---|---|
| 43 | 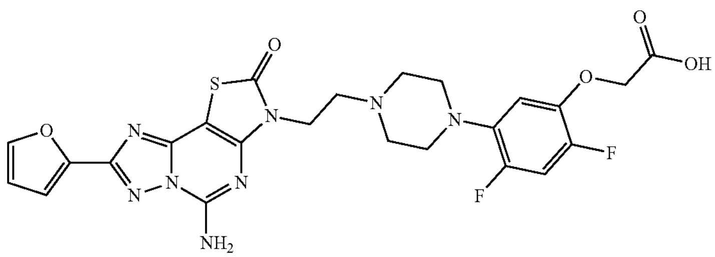 [SMILES: Nc1nc2c(sc(=O)n2CCN2CCN(c3cc(OCC(=O)O)c(F)cc3F)CC2)c2nc(-c3ccco3)nn12] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetic acid | 572.54 |
| 44 | 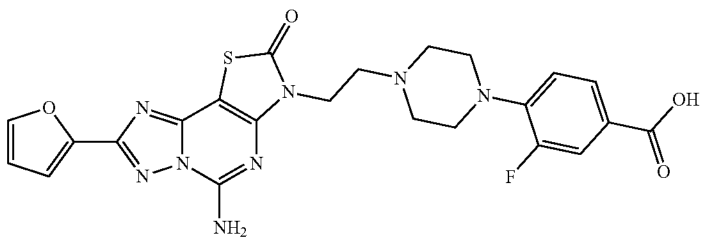 [SMILES: Nc1nc2c(sc(=O)n2CCN2CCN(c3ccc(C(=O)O)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorobenzoic acid | 524.53 |
| 45 | 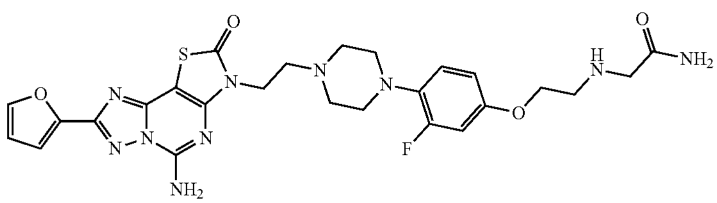 [SMILES: NC(=O)CNCCOc1ccc(N2CCN(CCn3c(=O)sc4c3nc(N)n3nc(-c5ccco5)nc43)CC2)c(F)c1] | 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)amino)acetamide | 596.64 |
| 46 | 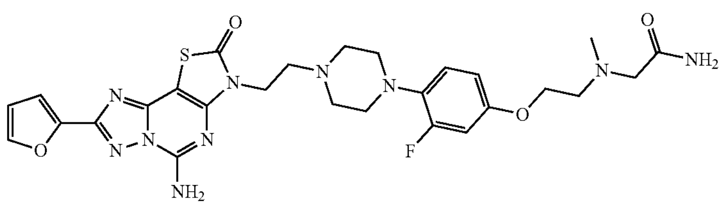 [SMILES: CN(CCOc1ccc(N2CCN(CCn3c(=O)sc4c3nc(N)n3nc(-c5ccco5)nc43)CC2)c(F)c1)CC(N)=O] | 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)(methyl)amino)acetamide | 610.66 |
| 47 | 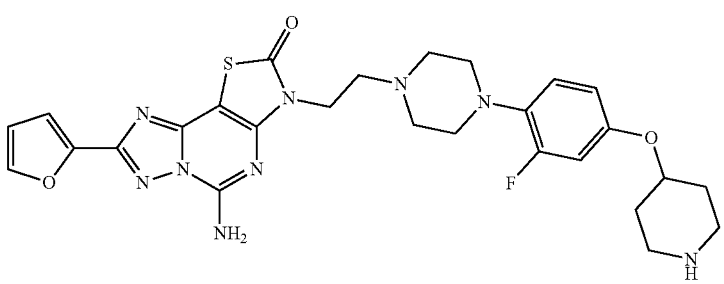 [SMILES: Nc1nc2c(sc(=O)n2CCN2CCN(c3ccc(OC4CCNCC4)cc3F)CC2)c2nc(-c3ccco3)nn12] | 5-amino-3-(2-(4-(2-fluoro-4-(piperidin-4-yloxy)phenyl)piperazin-1-yl)ethyl)-8-(furan-2-yl)thiazolo[5,4-e][1,2,4]triazolo[1,5-c]pyrimidin-2(3H)-one | 579.65 |
| 48 | 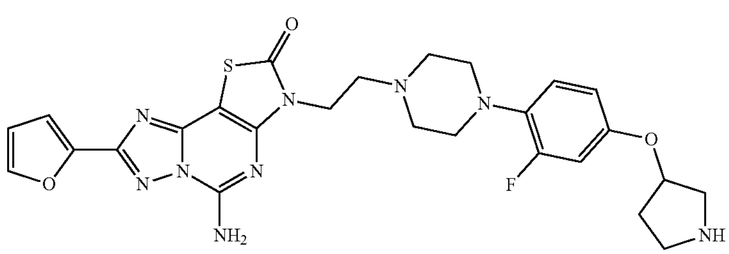 [SMILES: Nc1nc2c(sc(=O)n2CCN2CCN(c3ccc(OC4CCNC4)cc3F)CC2)c2nc(-c3ccco3)nn12] | 5-amino-3-(2-(4-(2-fluoro-4-(pyrrolidin-3-yloxy)phenyl)piperazin-1-yl)ethyl)-8-(furan-2-yl)thiazolo[5,4-e][1,2,4]triazolo[1,5-c]pyrimidin-2(3H)-one | 565.62 |

TABLE 1-continued

| Cpd n° | Structure | Chemical name | MW |
|---|---|---|---|
| 49 | 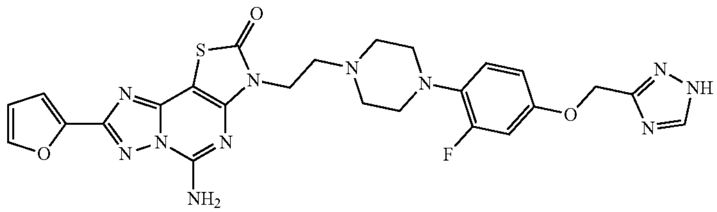 [SMILES: Nc1nc2c(sc(=O)n2CCN2CCN(c3ccc(OCc4nc[nH]n4)cc3F)CC2)c2nc(-c3ccco3)nn12] | 3-(2-(4-(4-((1H-1,2,4-triazol-3-yl)methoxy)-2-fluorophenyl)piperazin-1-yl)ethyl)-5-amino-8-(furan-2-yl)thiazolo[5,4-e][1,2,4]triazolo[1,5-c]pyrimidin-2(3H)-one | 577.59 |
| 50 | 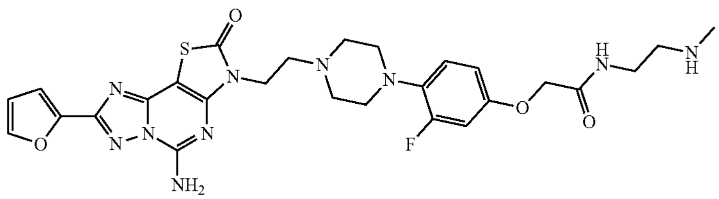 [SMILES: CNCCNC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(methylamino)ethyl)acetamide | 610.66 |
| 51 | 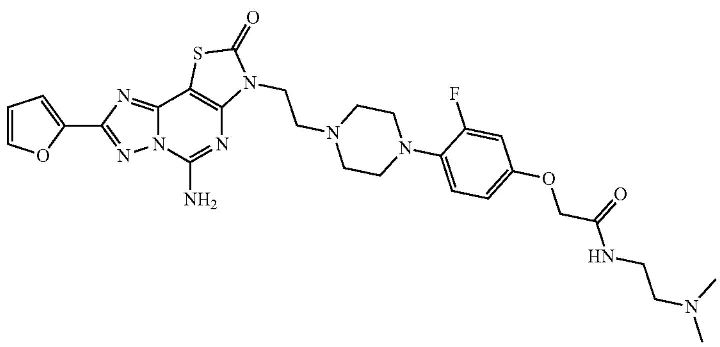 [SMILES: CN(C)CCNC(=O)COc1ccc(N2CCN(CCn3c(=O)sc4c3nc(N)n3nc(-c5ccco5)nc43)CC2)c(F)c1] | 2-(4-(4-(2-(5-amino-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(dimethylamino)ethyl)acetamide | 624.69 |
| 52 | 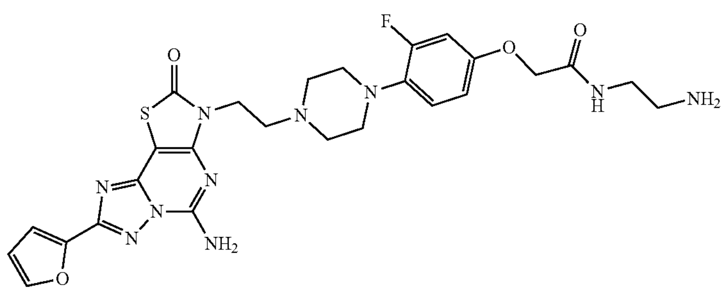 [SMILES: NCCNC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-aminoethyl)acetamide | 596.64 |
| 53 | 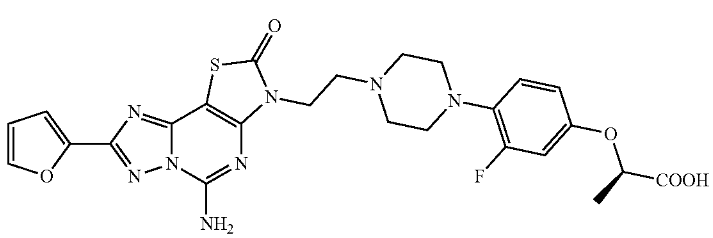 [SMILES: C[C@@H](Oc1ccc(N2CCN(CCn3c(=O)sc4c3nc(N)n3nc(-c5ccco5)nc43)CC2)c(F)c1)C(=O)O] | (R)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 54 | 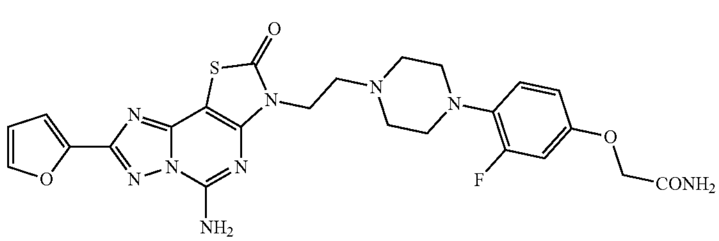 [SMILES: NC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetamide | 553.57 |

TABLE 1-continued

| Cpd n° | Structure | Chemical name | MW |
|---|---|---|---|
| 55 | 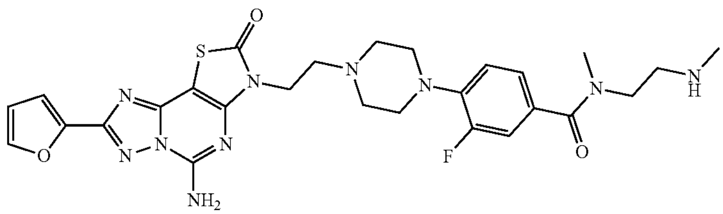 [SMILES: CNCCN(C)C(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-methyl-N-(2-(methylamino)ethyl) benzamide | 594.66 |
| 56 | 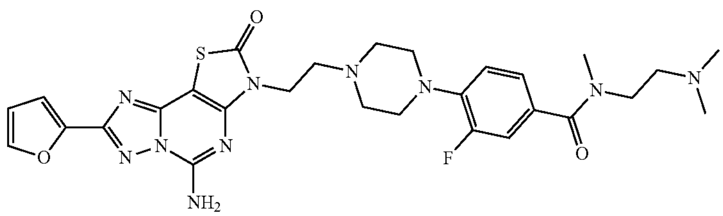 [SMILES: CN(C)CCN(C)C(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluoro-N-methylbenzamide | 608.69 |
| 57 | 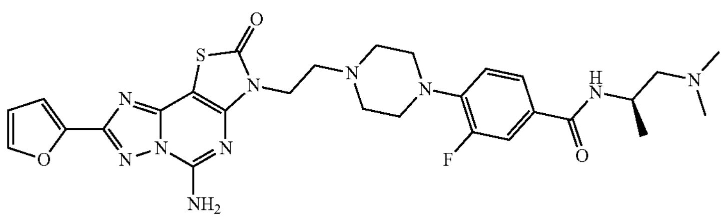 [SMILES: C[C@H](CN(C)C)NC(=O)c1ccc(N2CCN(CCn3c(=O)sc4c3nc(N)n3nc(-c5ccco5)nc43)CC2)c(F)c1] | (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(1-(dimethylamino)propan-2-yl)-3-fluorobenzamide | 608.69 |
| 58 | 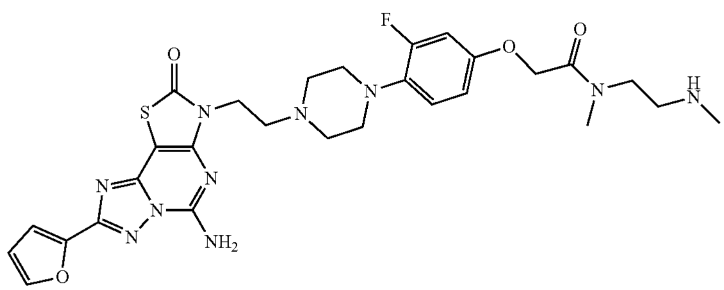 [SMILES: CNCCN(C)C(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-methyl-N-(2-(methylamino)ethyl) acetamide | 624.69 |
| 59 | 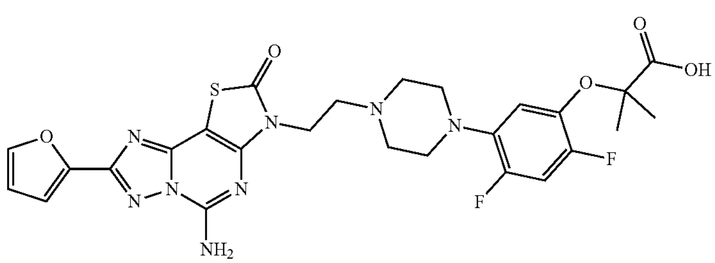 [SMILES: CC(C)(Oc1cc(N2CCN(CCn3c(=O)sc4c3nc(N)n3nc(-c5ccco5)nc43)CC2)c(F)cc1F)C(=O)O] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-2-methylpropanoic acid | 600.60 |
| 60 | 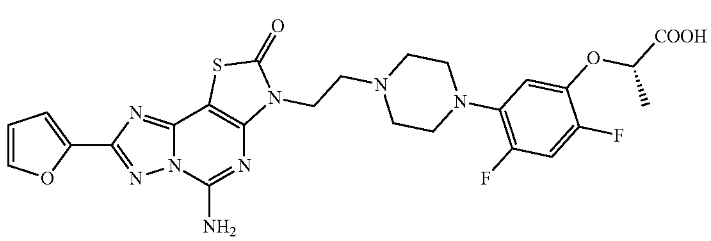 [SMILES: C[C@H](Oc1cc(N2CCN(CCn3c(=O)sc4c3nc(N)n3nc(-c5ccco5)nc43)CC2)c(F)cc1F)C(=O)O] | (S)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) propanoic acid | 586.57 |

TABLE 1-continued

| Cpd n° | Structure | Chemical name | MW |
|---|---|---|---|
| 61 | 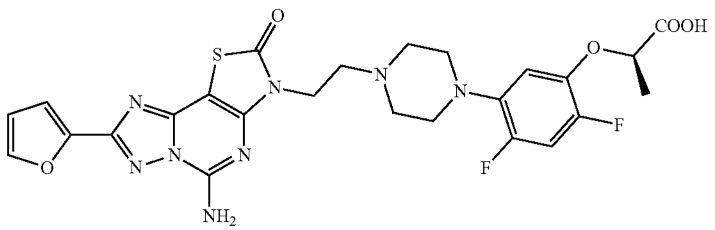 [SMILES: C[C@@H](Oc1cc(N2CCN(CCn3c(=O)sc4c3nc(N)n3nc(-c5ccco5)nc43)CC2)c(F)cc1F)C(=O)O] | (R)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) propanoic acid | 586.57 |
| 62 | 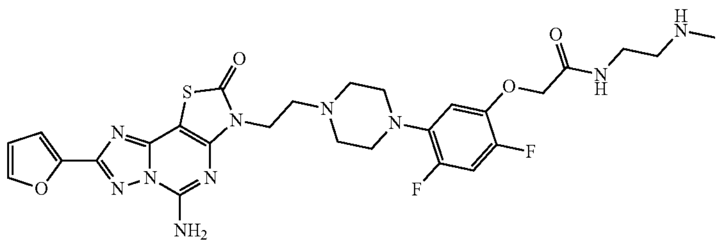 [SMILES: CNCCNC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(methylamino)ethyl) acetamide | 628.65 |
| 63 | 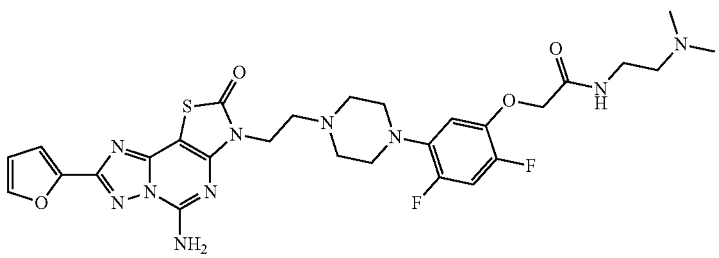 [SMILES: CN(C)CCNC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(dimethylamino)ethyl) acetamide | 642.68 |
| 64 | 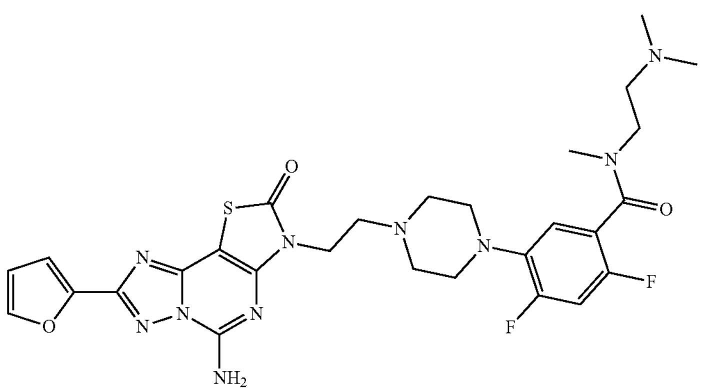 [SMILES: CN(C)CCN(C)C(=O)c1cc(N2CCN(CCn3c(=O)sc4c3nc(N)n3nc(-c5ccco5)nc43)CC2)c(F)cc1F] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluoro-N-methylbenzamide | 626.69 |
| 65 | 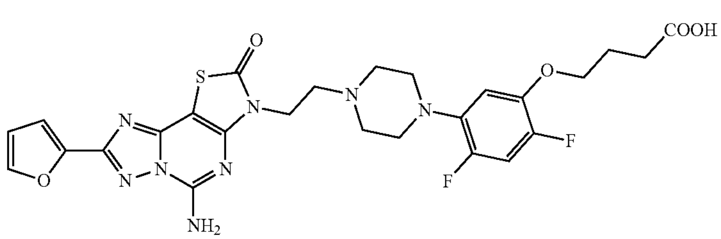 [SMILES: Nc1nc2c(sc(=O)n2CCN2CCN(c3cc(OCCCC(=O)O)c(F)cc3F)CC2)c2nc(-c3ccco3)nn12] | 4-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) butanoic acid | 600.60 |

TABLE 1-continued

| Cpd n° | Structure | Chemical name | MW |
|---|---|---|---|
| 66 | 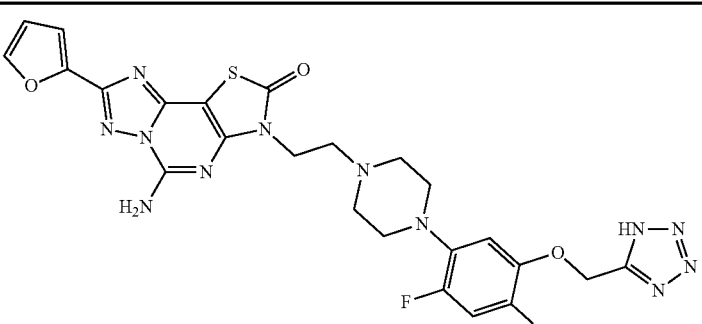 | 3-(2-(4-(5-((1H-tetrazol-5-yl)methoxy)-2,4-difluorophenyl)piperazin-1-yl)ethyl)-5-amino-8-(furan-2-yl)thiazolo[5,4-e][1,2,4]triazolo[1,5-c]pyrimidin-2(3H)-one | 596.58 |
| 67 | 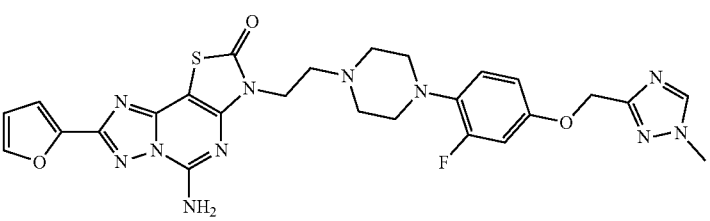 [SMILES: Cn1cnc(COc2ccc(N3CCN(CCn4c(=O)sc5c4nc(N)n4nc(-c6ccco6)nc54)CC3)c(F)c2)n1] | 5-amino-3-(2-(4-(2-fluoro-4-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one | 591.62 |
| 68 | 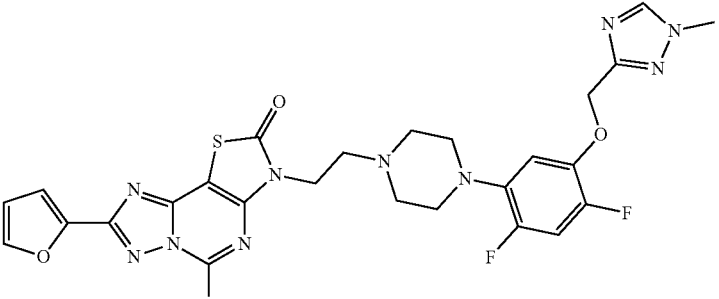 | 5-amino-3-(2-(4-(2,4-difluoro-5-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one | 609.62 |
| 69 | 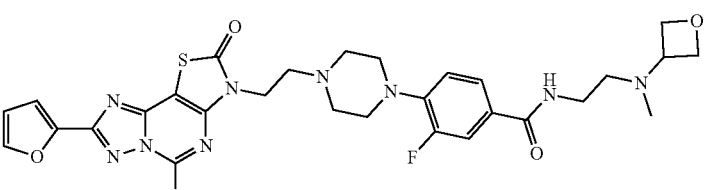 | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methyl(oxetan-3-yl)amino)ethyl)benzamide | 636.70 |
| 70 | 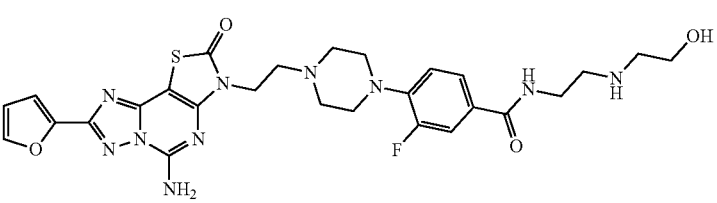 [SMILES: Nc1nc2c(sc(=O)n2CCN2CCN(c3ccc(C(=O)NCCNCCO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-((2-hydroxyethyl)amino)ethyl)benzamide | 610.67 |
| 71 | 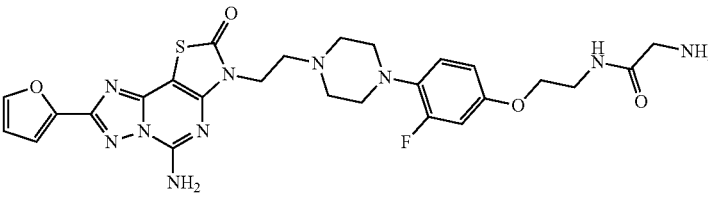 | 2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)acetamide | 596.64 |

TABLE 1-continued

| Cpd n° | Structure | Chemical name | MW |
|---|---|---|---|
| 72 | 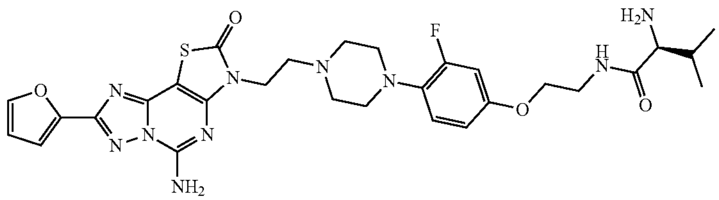 [SMILES: CC(C)[C@H](N)C(=O)NCCOc1ccc(N2CCN(CCn3c(=O)sc4c3nc(N)n3nc(-c5ccco5)nc43)CC2)c(F)c1] | (S)-2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)-3-methylbutanamide | 638.72 |
| 73 | 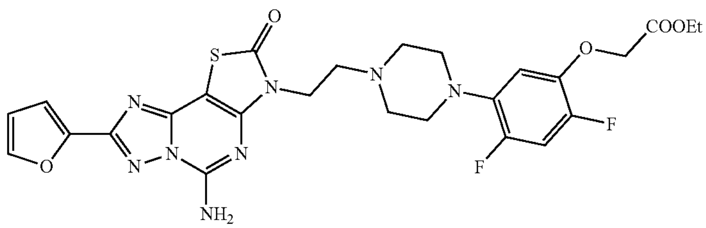 [SMILES: CCOC(=O)COc1cc(N2CCN(CCn3c(=O)sc4c3nc(N)n3nc(-c5ccco5)nc43)CC2)c(F)cc1F] | ethyl 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetate | 600.60 |
| 74 | 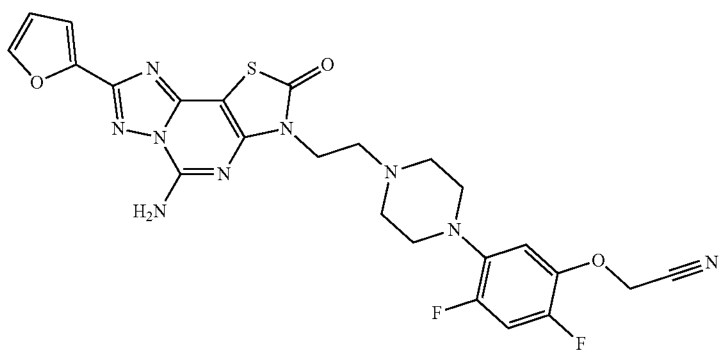 [SMILES: N#CCOc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetonitrile | 553.54 |
| 75 | 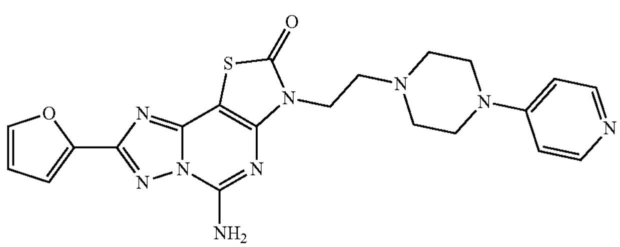 [SMILES: Nc1nc2c(sc(=O)n2CCN2CCN(c3ccncc3)CC2)c2nc(-c3ccco3)nn12] | 5-amino-8-(furan-2-yl)-3-(2-(4-(pyridin-4-yl)piperazin-1-yl)ethyl)thiazolo[5,4-e][1,2,4]triazolo[1,5-c]pyrimidin-2(3H)-one | 463.52 |
| 76 | 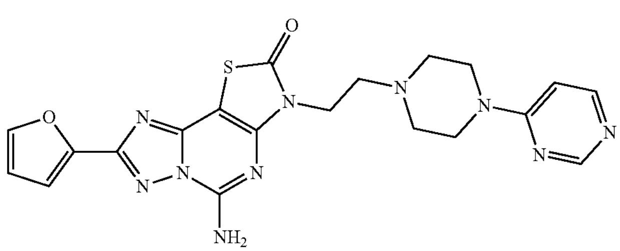 [SMILES: Nc1nc2c(sc(=O)n2CCN2CCN(c3ccncn3)CC2)c2nc(-c3ccco3)nn12] | 5-amino-8-(furan-2-yl)-3-(2-(4-(pyrimidin-4-yl)piperazin-1-yl)ethyl)thiazolo[5,4-e][1,2,4]triazolo[1,5-c]pyrimidin-2(3H)-one | 464.50 |

TABLE 1-continued

| Cpd n° | Structure | Chemical name | MW |
|---|---|---|---|
| 77 | 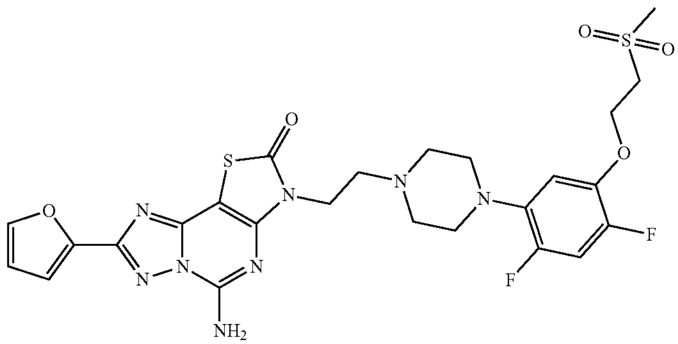 [SMILES: CS(=O)(=O)CCOc1cc(N2CCN(CCn3c(=O)sc4c3nc(N)n3nc(-c5ccco5)nc43)CC2)c(F)cc1F] | 5-amino-3-(2-(4-(2,4-difluoro-5-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one | 620.65 |
| 78 | 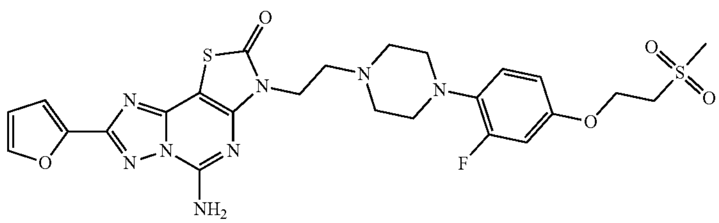 [SMILES: CS(=O)(=O)CCOc1ccc(N2CCN(CCn3c(=O)sc4c3nc(N)n3nc(-c5ccco5)nc43)CC2)c(F)c1] | 5-amino-3-(2-(4-(2-fluoro-4-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one | 602.66 |
| 79 | 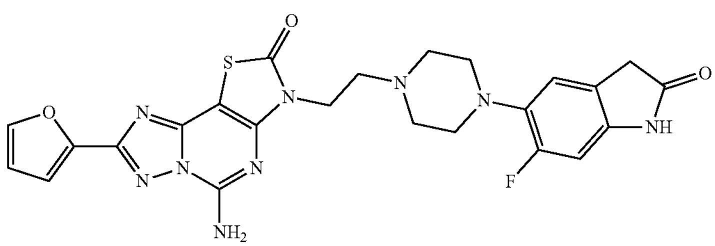 [SMILES: Nc1nc2c(sc(=O)n2CCN2CCN(c3cc4c(cc3F)NC(=O)C4)CC2)c2nc(-c3ccco3)nn12] | 5-amino-3-(2-(4-(6-fluoro-2-oxoindolin-5-yl)piperazin-1-yl)ethyl)-8-(furan-2-yl)thiazolo[5,4-e][1,2,4]triazolo[1,5-c]pyrimidin-2(3H)-one | 535.55 |
| 80 | 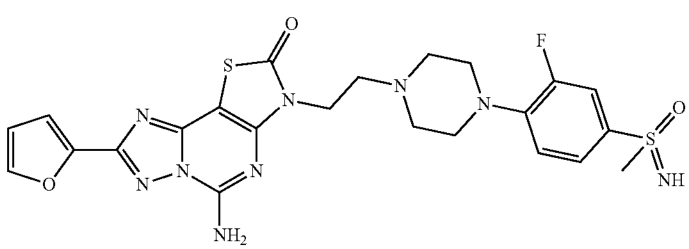 [SMILES: CS(=N)(=O)c1ccc(N2CCN(CCn3c(=O)sc4c3nc(N)n3nc(-c5ccco5)nc43)CC2)c(F)c1] | 5-amino-3-(2-(4-(2-fluoro-4-(S-methylsulfonimidoyl)phenyl)piperazin-1-yl)ethyl)-8-(furan-2-yl)thiazolo[5,4-e][1,2,4]triazolo[1,5-c]pyrimidin-2(3H)-one | 557.62 |
| 81 | 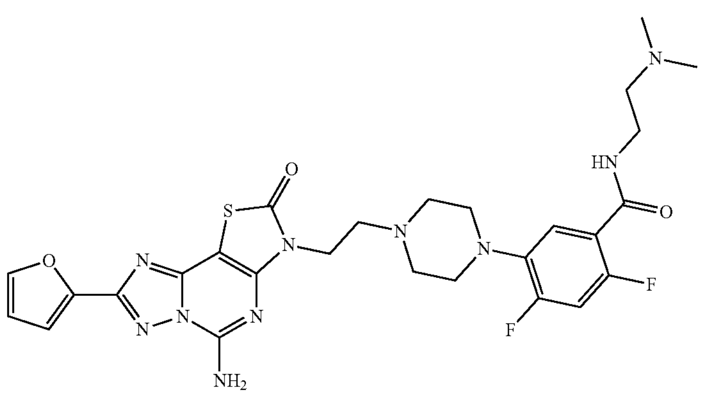 [SMILES: CN(C)CCNC(=O)c1cc(N2CCN(CCn3c(=O)sc4c3nc(N)n3nc(-c5ccco5)nc43)CC2)c(F)cc1F] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluorobenzamide | 612.65 |

TABLE 1-continued

| Cpd n° | Structure | Chemical name | MW |
|---|---|---|---|
| 82 | 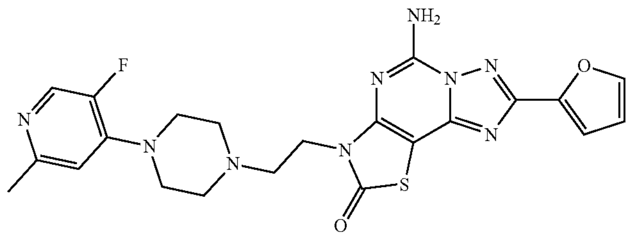 [SMILES: Cc1cc(N2CCN(CCn3c(=O)sc4c3nc(N)n3nc(-c5ccco5)nc43)CC2)c(F)cn1] | 5-amino-3-(2-(4-(5-fluoro-2-methylpyridin-4-yl)piperazin-1-yl)ethyl)-8-(furan-2-yl)thiazolo[5,4-e][1,2,4]triazolo[1,5-c]pyrimidin-2(3H)-one | 495.53 |
| 83 | 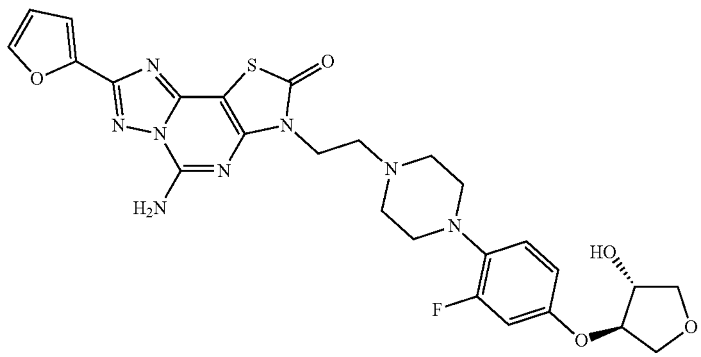 [SMILES: Nc1nc2c(sc(=O)n2CCN2CCN(c3ccc(O[C@@H]4COC[C@H]4O)cc3F)CC2)c2nc(-c3ccco3)nn12] | 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one | 582.61 |
| 84 | 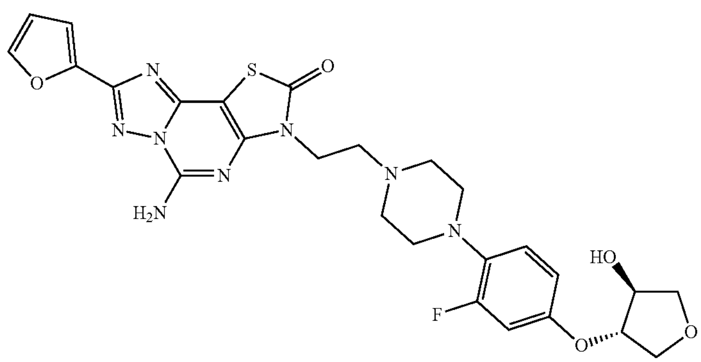 [SMILES: Nc1nc2c(sc(=O)n2CCN2CCN(c3ccc(O[C@H]4COC[C@@H]4O)cc3F)CC2)c2nc(-c3ccco3)nn12] | 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one | 582.61 |
| 85 | 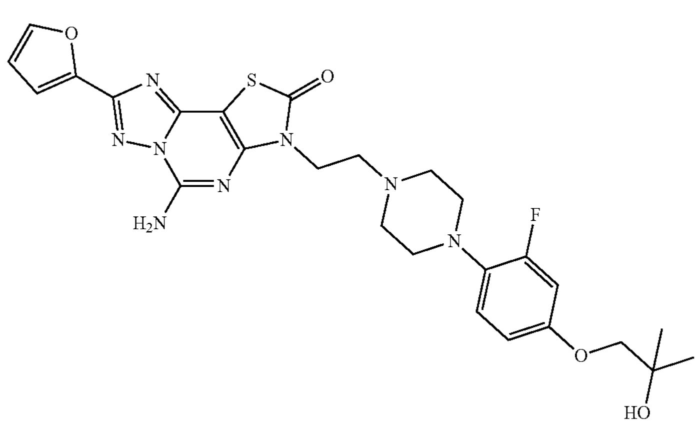 [SMILES: CC(C)(O)COc1ccc(N2CCN(CCn3c(=O)sc4c3nc(N)n3nc(-c5ccco5)nc43)CC2)c(F)c1] | 5-amino-3-(2-(4-(2-fluoro-4-(2-hydroxy-2-methylpropoxy)phenyl)piperazin-1-yl)ethyl)-8-(furan-2-yl)thiazolo[5,4-e][1,2,4]triazolo[1,5-c]pyrimidin-2(3H)-one | 568.62 |

TABLE 1-continued

| Cpd n° | Structure | Chemical name | MW |
|---|---|---|---|
| 86 | 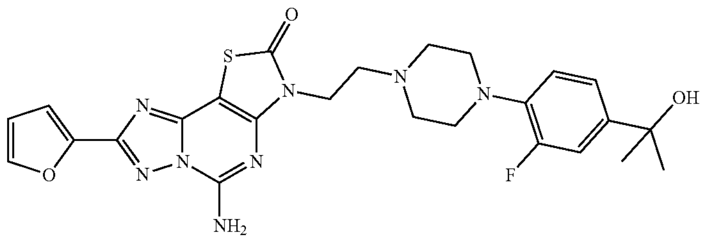 [SMILES: CC(C)(O)c1ccc(N2CCN(CCn3c(=O)sc4c3nc(N)n3nc(-c5ccco5)nc43)CC2)c(F)c1] | 5-amino-3-(2-(4-(2-fluoro-4-(2-hydroxypropan-2-yl)phenyl)piperazin-1-yl)ethyl)-8-(furan-2-yl)thiazolo[5,4-e][1,2,4]triazolo[1,5-c]pyrimidin-2(3H)-one | 538.60 |
| 87 | 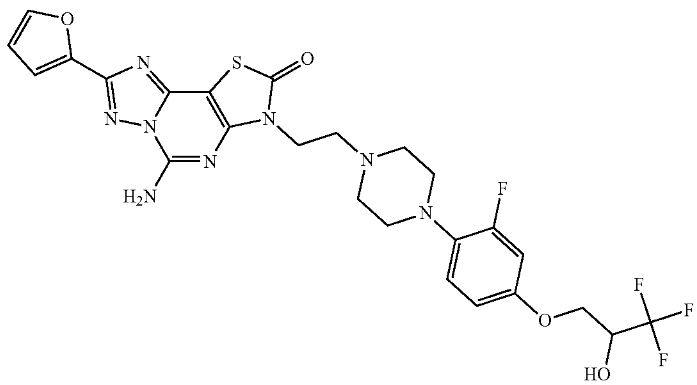 [SMILES: Nc1nc2c(sc(=O)n2CCN2CCN(c3ccc(OCC(O)C(F)(F)F)cc3F)CC2)c2nc(-c3ccco3)nn12] | 5-amino-3-(2-(4-(2-fluoro-4-(3,3,3-trifluoro-2-hydroxypropoxy)phenyl)piperazin-1-yl)ethyl)-8-(furan-2-yl)thiazolo[5,4-e][1,2,4]triazolo[1,5-c]pyrimidin-2(3H)-one | 608.57 |
| 88 | 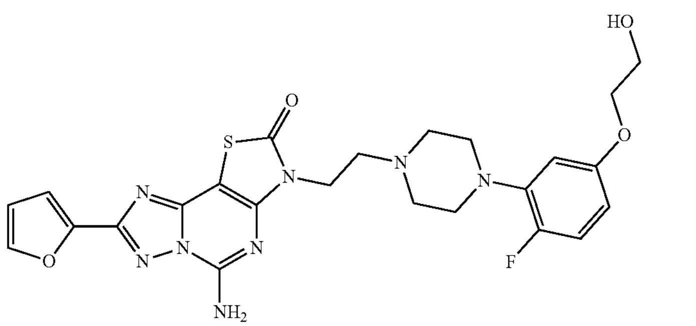 [SMILES: Nc1nc2c(sc(=O)n2CCN2CCN(c3cc(OCCO)ccc3F)CC2)c2nc(-c3ccco3)nn12] | 5-amino-3-(2-(4-(2-fluoro-5-(2-hydroxyethoxy)phenyl)piperazin-1-yl)ethyl)-8-(furan-2-yl)thiazolo[5,4-e][1,2,4]triazolo[1,5-c]pyrimidin-2(3H)-one | 540.57 |
| 89 | 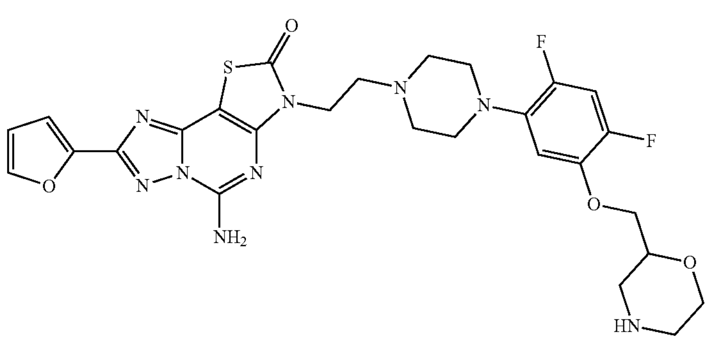 [SMILES: Nc1nc2c(sc(=O)n2CCN2CCN(c3cc(OCC4CNCCO4)c(F)cc3F)CC2)c2nc(-c3ccco3)nn12] | 5-amino-3-(2-(4-(2,4-difluoro-5-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one | 613.64 |

TABLE 1-continued

| Cpd n° | Structure | Chemical name | MW |
|---|---|---|---|
| 90 | 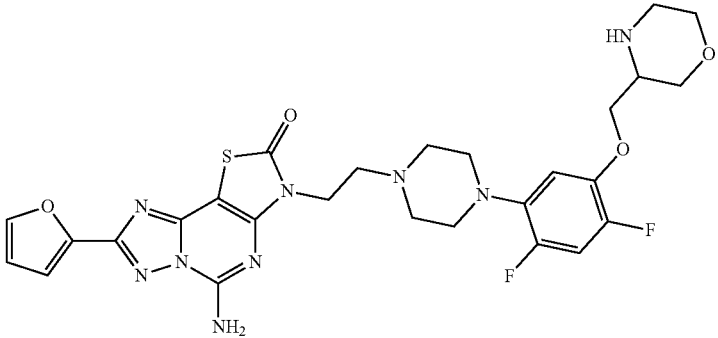 [SMILES: Nc1nc2c(sc(=O)n2CCN2CCN(c3cc(OCC4COCCN4)c(F)cc3F)CC2)c2nc(-c3ccco3)nn12] | 5-amino-3-(2-(4-(2,4-difluoro-5-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one | 613.64 |
| 91 | 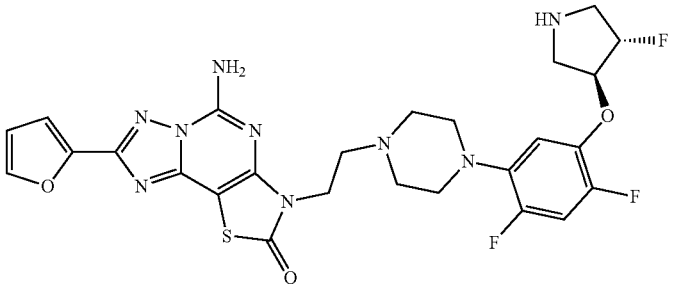 [SMILES: Nc1nc2c(sc(=O)n2CCN2CCN(c3cc(O[C@H]4CNC[C@@H]4F)c(F)cc3F)CC2)c2nc(-c3ccco3)nn12] | 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 92 | 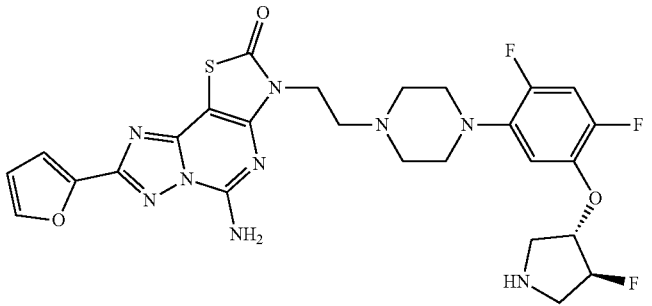 [SMILES: Nc1nc2c(sc(=O)n2CCN2CCN(c3cc(O[C@H]4CNC[C@@H]4F)c(F)cc3F)CC2)c2nc(-c3ccco3)nn12] | 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 93 | 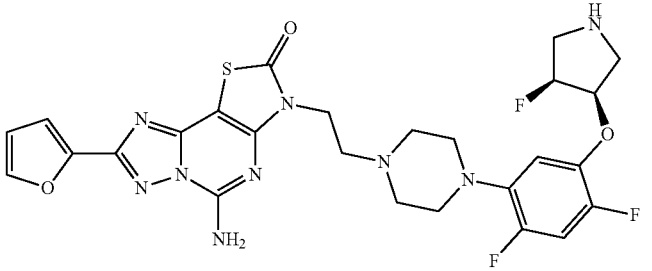 [SMILES: Nc1nc2c(sc(=O)n2CCN2CCN(c3cc(O[C@@H]4CNC[C@@H]4F)c(F)cc3F)CC2)c2nc(-c3ccco3)nn12] | 5-amino-3-(2-(4-(2,4-difluoro-5-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 94 | 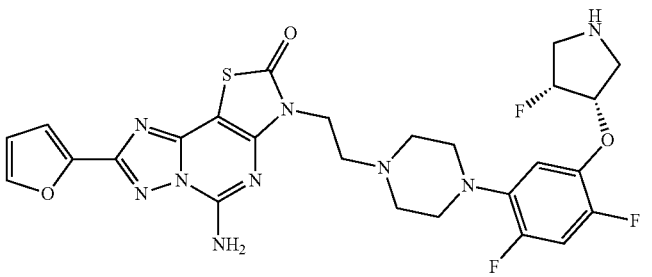 [SMILES: Nc1nc2c(sc(=O)n2CCN2CCN(c3cc(O[C@H]4CNC[C@H]4F)c(F)cc3F)CC2)c2nc(-c3ccco3)nn12] | 5-amino-3-(2-(4-(2,4-difluoro-5-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |

TABLE 1-continued

| Cpd n° | Structure | Chemical name | MW |
|---|---|---|---|
| 95 | 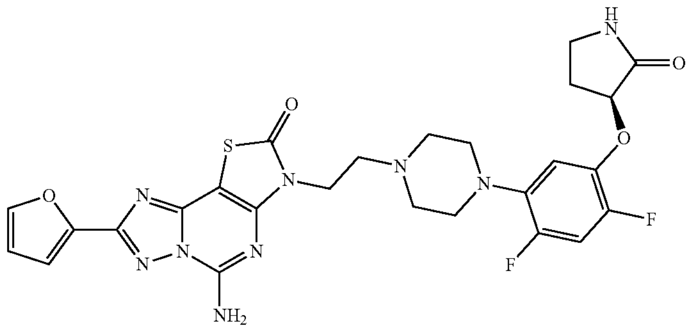 [SMILES: Nc1nc2c(sc(=O)n2CCN2CCN(c3cc(O[C@H]4CCNC4=O)c(F)cc3F)CC2)c2nc(-c3ccco3)nn12] | (S)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 597.60 |
| 96 | 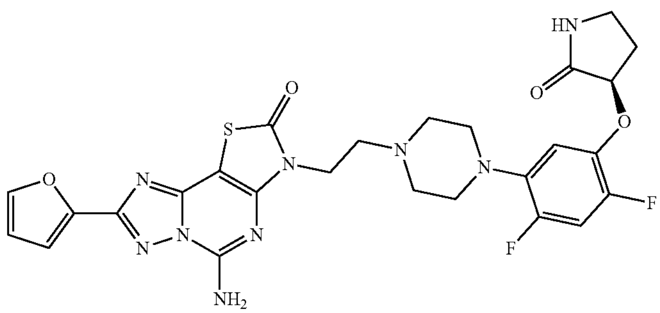 [SMILES: Nc1nc2c(sc(=O)n2CCN2CCN(c3cc(O[C@@H]4CCNC4=O)c(F)cc3F)CC2)c2nc(-c3ccco3)nn12] | (R)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 597.60 |
| 97 | 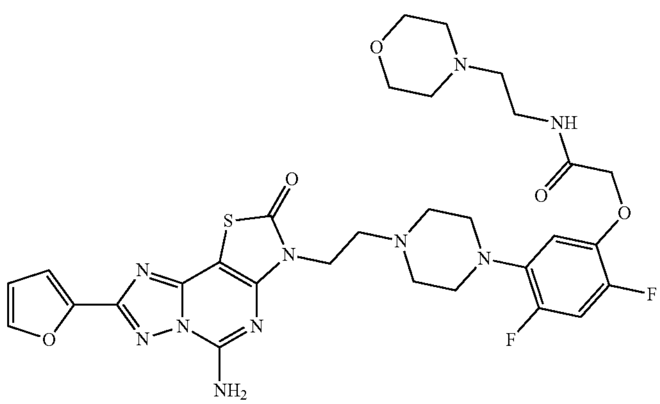 [SMILES: Nc1nc2c(sc(=O)n2CCN2CCN(c3cc(OCC(=O)NCCN4CCOCC4)c(F)cc3F)CC2)c2nc(-c3ccco3)nn12] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-morpholinoethyl)acetamide | 684.72 |
| 98 | 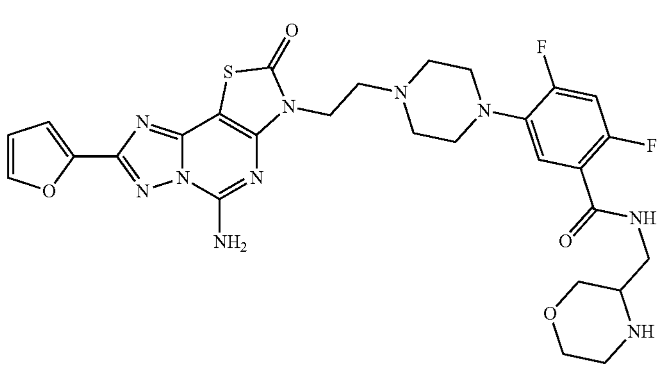 [SMILES: Nc1nc2c(sc(=O)n2CCN2CCN(c3cc(C(=O)NCC4COCCN4)c(F)cc3F)CC2)c2nc(-c3ccco3)nn12] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(morpholin-3-ylmethyl)benzamide | 640.66 |

TABLE 1-continued

| Cpd n° | Structure | Chemical name | MW |
|---|---|---|---|
| 99 | 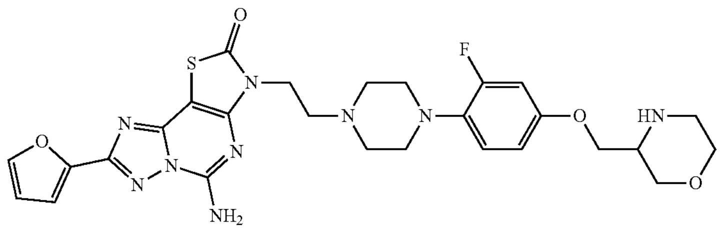 [SMILES: Nc1nc2c(sc(=O)n2CCN2CCN(c3ccc(OCC4COCCN4)cc3F)CC2)c2nc(-c3ccco3)nn12] | 5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one | 595.65 |
| 100 | 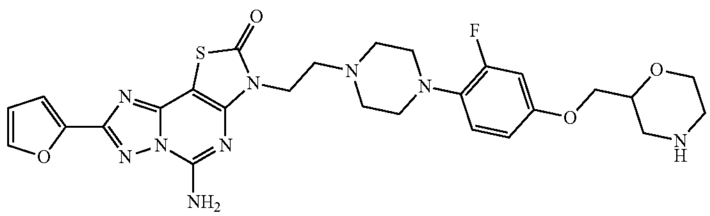 [SMILES: Nc1nc2c(sc(=O)n2CCN2CCN(c3ccc(OCC4CNCCO4)cc3F)CC2)c2nc(-c3ccco3)nn12] | 5-amino-3-(2-(4-(2-fluoro-4-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one | 595.65 |
| 101 | 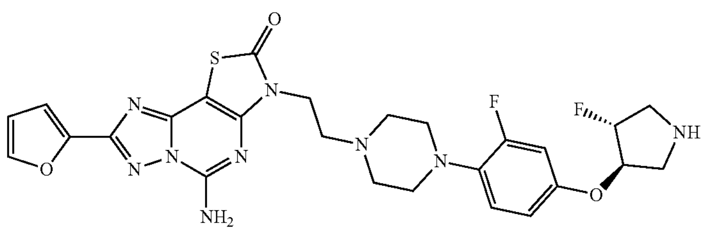 [SMILES: Nc1nc2c(sc(=O)n2CCN2CCN(c3ccc(O[C@@H]4CNC[C@H]4F)cc3F)CC2)c2nc(-c3ccco3)nn12] | 5-amino-3-(2-(4-(2-fluoro-4-(((3R,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 102 | 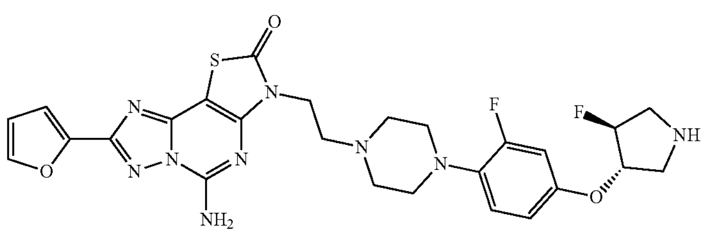 [SMILES: Nc1nc2c(sc(=O)n2CCN2CCN(c3ccc(O[C@H]4CNC[C@@H]4F)cc3F)CC2)c2nc(-c3ccco3)nn12] | 5-amino-3-(2-(4-(2-fluoro-4-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 103 | 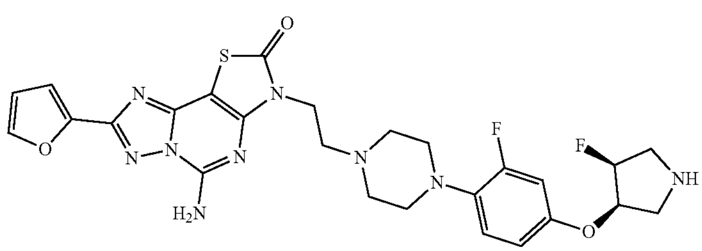 [SMILES: Nc1nc2c(sc(=O)n2CCN2CCN(c3ccc(O[C@@H]4CNC[C@@H]4F)cc3F)CC2)c2nc(-c3ccco3)nn12] | 5-amino-3-(2-(4-(2-fluoro-4-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 104 | 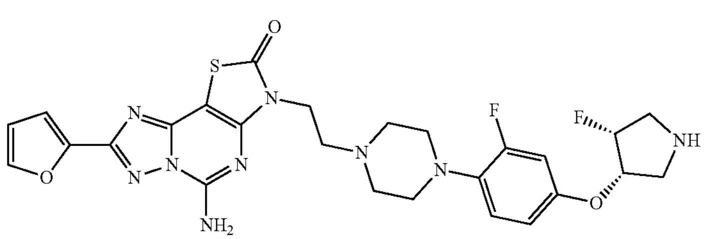 [SMILES: Nc1nc2c(sc(=O)n2CCN2CCN(c3ccc(O[C@H]4CNC[C@H]4F)cc3F)CC2)c2nc(-c3ccco3)nn12] | 5-amino-3-(2-(4-(2-fluoro-4-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |

TABLE 1-continued

| Cpd n° | Structure | Chemical name | MW |
|---|---|---|---|
| 105 | 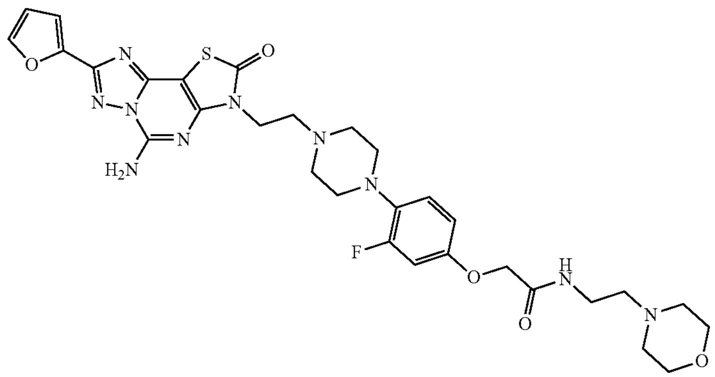 [SMILES: Nc1nc2c(sc(=O)n2CCN2CCN(c3ccc(OCC(=O)NCCN4CCOCC4)cc3F)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-morpholinoethyl)acetamide | 666.73 |
| 106 | 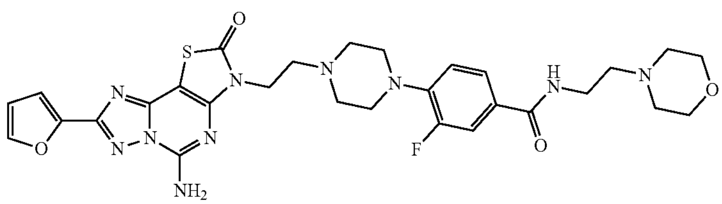 [SMILES: Nc1nc2c(sc(=O)n2CCN2CCN(c3ccc(C(=O)NCCN4CCOCC4)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-morpholinoethyl)benzamide | 636.70 |
| 107 | 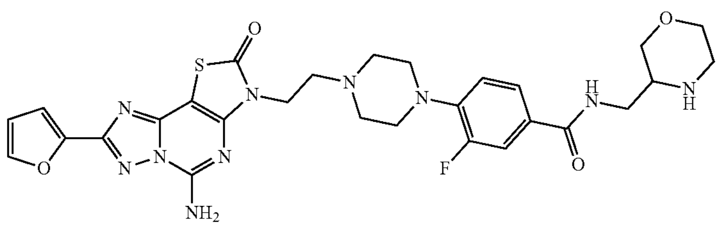 [SMILES: Nc1nc2c(sc(=O)n2CCN2CCN(c3ccc(C(=O)NCC4COCCN4)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(morpholin-3-ylmethyl)benzamide | 622.67 |
| 108 | 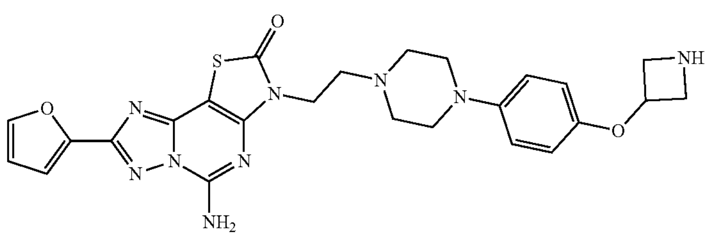 [SMILES: Nc1nc2c(sc(=O)n2CCN2CCN(c3ccc(OC4CNC4)cc3)CC2)c2nc(-c3ccco3)nn12] | 5-amino-3-(2-(4-(4-(azetidin-3-yloxy)phenyl)piperazin-1-yl)ethyl)-8-(furan-2-yl)thiazolo[5,4-e][1,2,4]triazolo[1,5-c]pyrimidin-2(3H)-one | 533.61 |
| 109 | 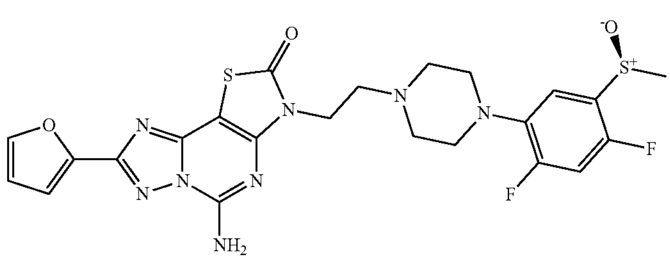 | (S)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one | 560.60 |
| 110 | 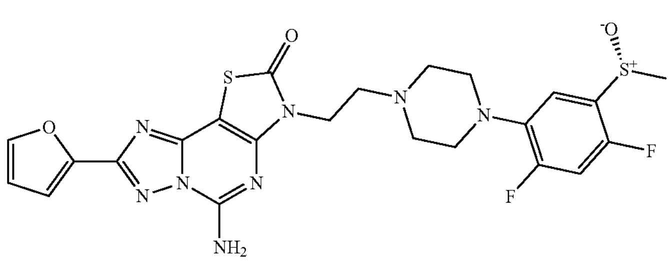 | (R)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one | 560.60 |

TABLE 1-continued

| Cpd n° | Structure | Chemical name | MW |
|---|---|---|---|
| 111 | 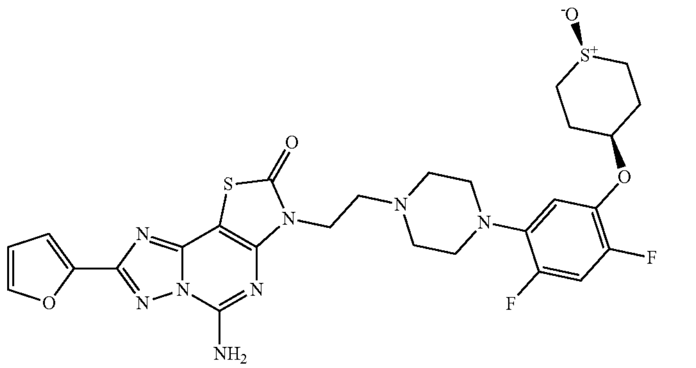 | 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 630.69 |
| 112 | 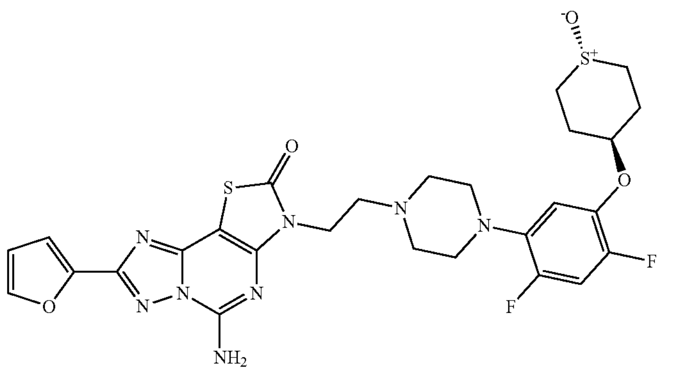 | 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 630.69 |
| 113 | 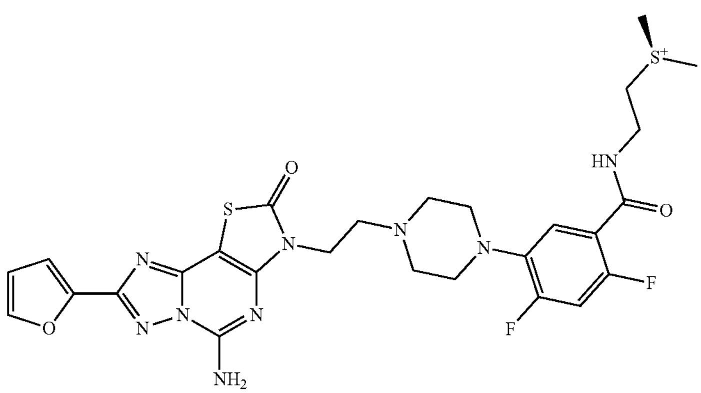 | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide | 631.68 |
| 114 | 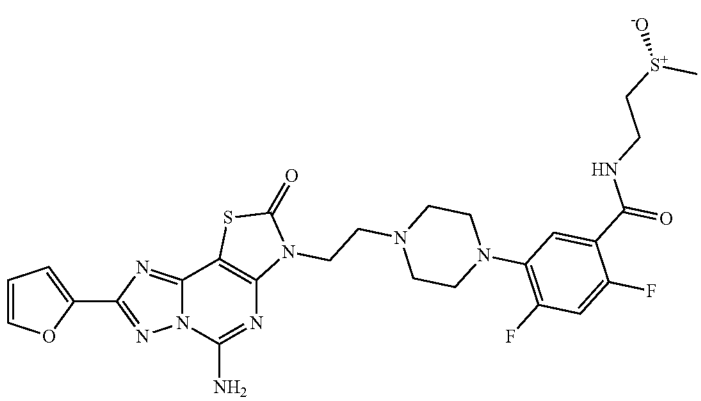 | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide | 631.68 |

TABLE 1-continued

| Cpd n° | Structure | Chemical name | MW |
|---|---|---|---|
| 115 | 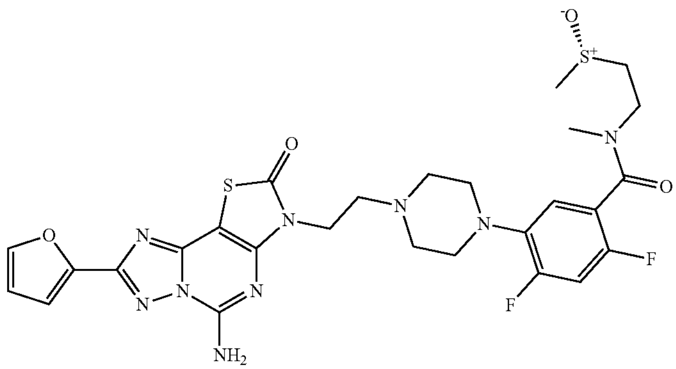 | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide | 645.70 |
| 116 | 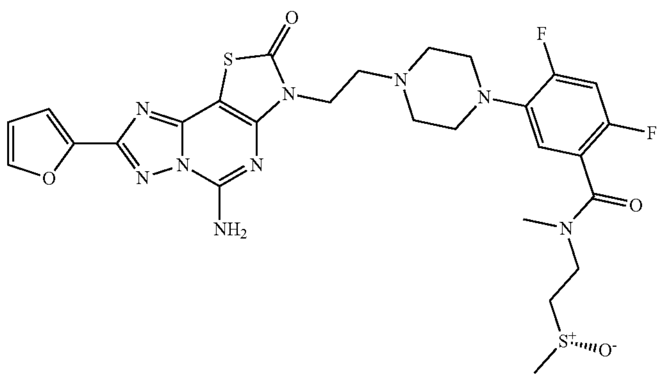 [SMILES: CN(CC[S@@+](C)[O-])C(=O)c1cc(N2CCN(CCn3c(=O)sc4c3nc(N)n3nc(-c5ccco5)nc43)CC2)c(F)cc1F] | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide | 645.70 |
| 117 | 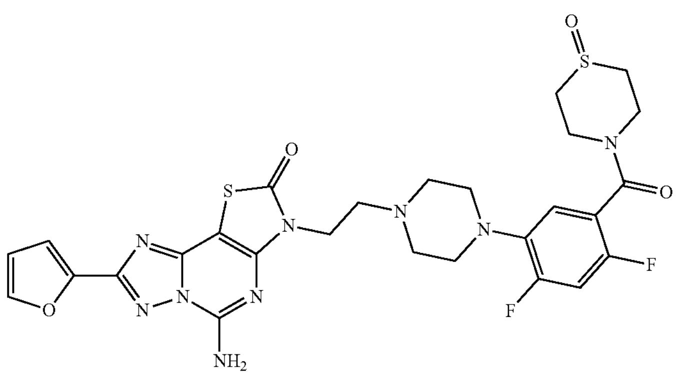 [SMILES: Nc1nc2c(sc(=O)n2CCN2CCN(c3cc(C(=O)N4CCS(=O)CC4)c(F)cc3F)CC2)c2nc(-c3ccco3)nn12] | 5-amino-3-(2-(4-(2,4-difluoro-5-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one | 643.69 |
| 118 | 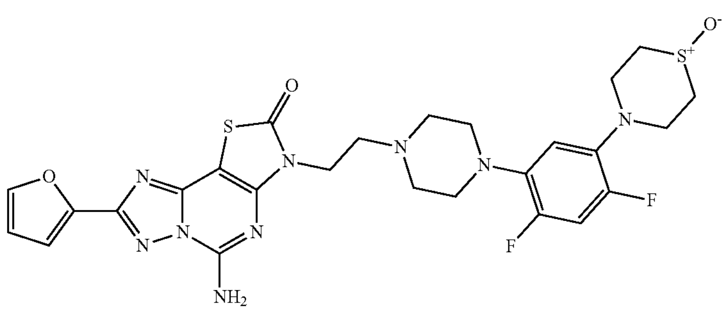 [SMILES: Nc1nc2c(sc(=O)n2CCN2CCN(c3cc(N4CC[S+]([O-])CC4)c(F)cc3F)CC2)c2nc(-c3ccco3)nn12] | 5-amino-3-(2-(4-(2,4-difluoro-5-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one | 615.68 |

TABLE 1-continued

| Cpd n° | Structure | Chemical name | MW |
|---|---|---|---|
| 119 | 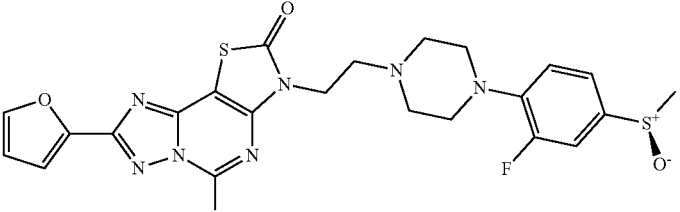 | (R)-5-amino-3-(2-(4-(2-fluoro-4-(methylsulfinyl)phenyl)piper-azin-1-yl)ethyl)-8-(furan-2-yl)thiazolo[5,4-e][1,2,4]triazolo[1,5-c]pyrimidin-2(3H)-one | 542.61 |
| 120 | 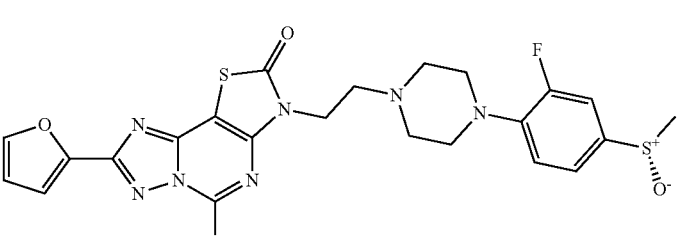 | (S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one | 542.61 |
| 121 | 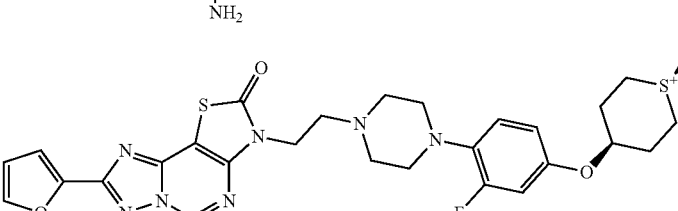 | 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 612.70 |
| 122 | 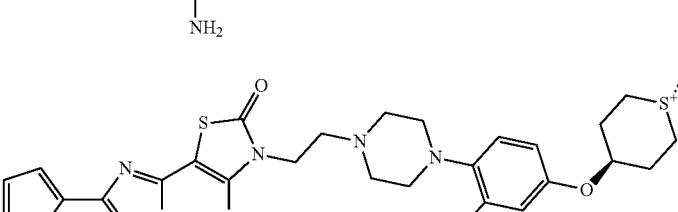 | 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)thiazolo [5,4-e][1,2,4]triazolo[1,5-c]pyrimidin-2(3H)-one | 612.70 |
| 123 | 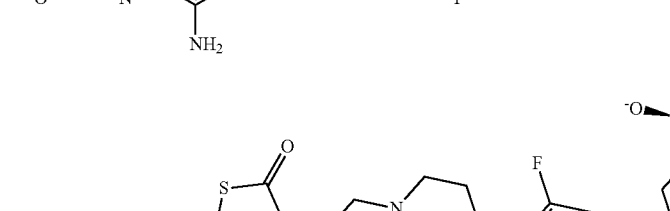 | (S)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide | 613.69 |
| 124 | 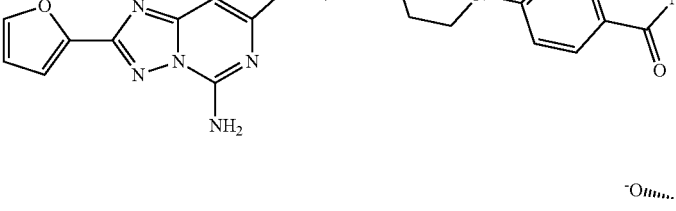 | (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide | 613.69 |

TABLE 1-continued

| Cpd n° | Structure | Chemical name | MW |
|---|---|---|---|
| 125 | 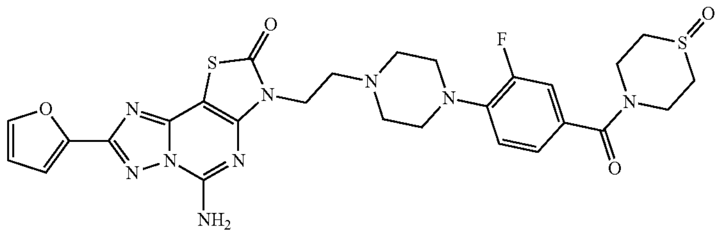 [SMILES: Nc1nc2c(sc(=O)n2CCN2CCN(c3ccc(C(=O)N4CCS(=O)CC4)cc3F)CC2)c2nc(-c3ccco3)nn12] | 5-amino-3-(2-(4-(2-fluoro-4-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one | 625.70 |
| 126 | 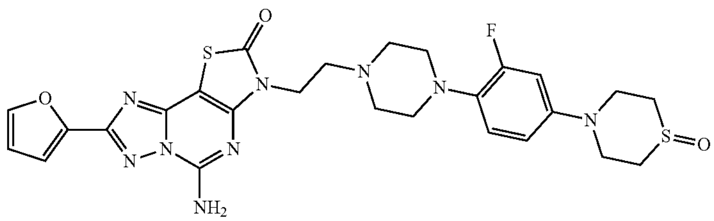 [SMILES: Nc1nc2c(sc(=O)n2CCN2CCN(c3ccc(N4CCS(=O)CC4)cc3F)CC2)c2nc(-c3ccco3)nn12] | 5-amino-3-(2-(4-(2-fluoro-4-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one | 597.69 |
| 127 | 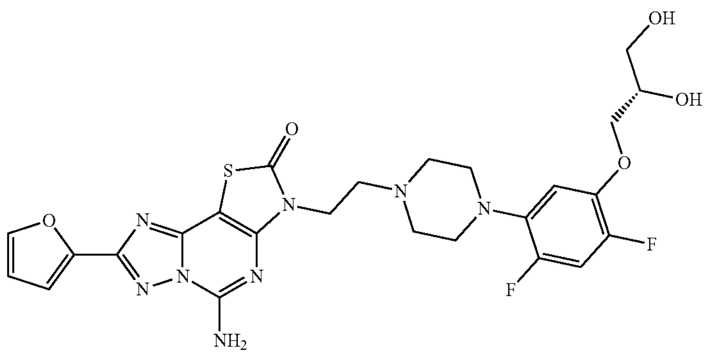 [SMILES: Nc1nc2c(sc(=O)n2CCN2CCN(c3cc(OC[C@@H](O)CO)c(F)cc3F)CC2)c2nc(-c3ccco3)nn12] | (S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one | 588.59 |
| 128 | 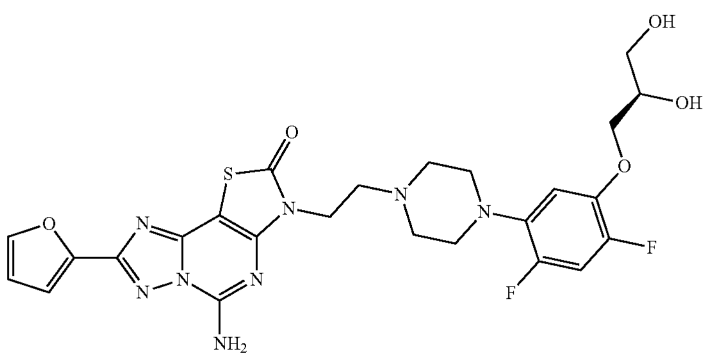 [SMILES: Nc1nc2c(sc(=O)n2CCN2CCN(c3cc(OC[C@H](O)CO)c(F)cc3F)CC2)c2nc(-c3ccco3)nn12] | (R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one | 588.59 |
| 129 | 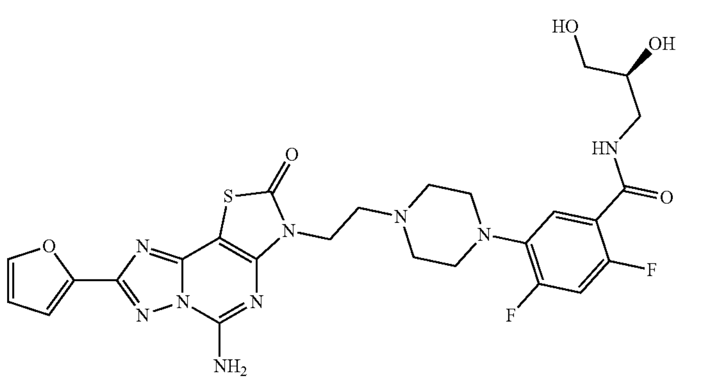 [SMILES: Nc1nc2c(sc(=O)n2CCN2CCN(c3cc(C(=O)NC[C@H](O)CO)c(F)cc3F)CC2)c2nc(-c3ccco3)nn12] | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide | 615.61 |

TABLE 1-continued

| Cpd n° | Structure | Chemical name | MW |
|---|---|---|---|
| 130 | 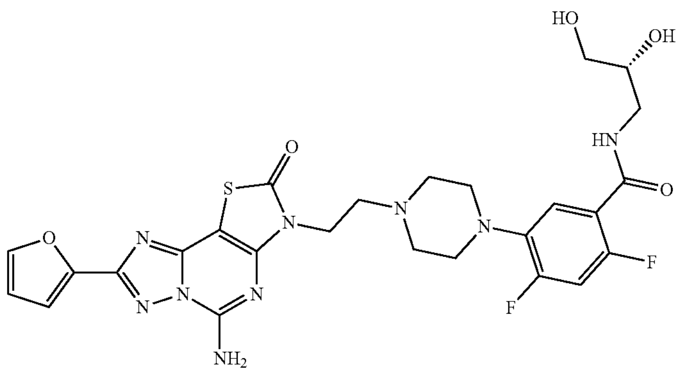 [SMILES: Nc1nc2c(sc(=O)n2CCN2CCN(c3cc(C(=O)NC[C@@H](O)CO)c(F)cc3F)CC2)c2nc(-c3ccco3)nn12] | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide | 615.61 |
| 131 | 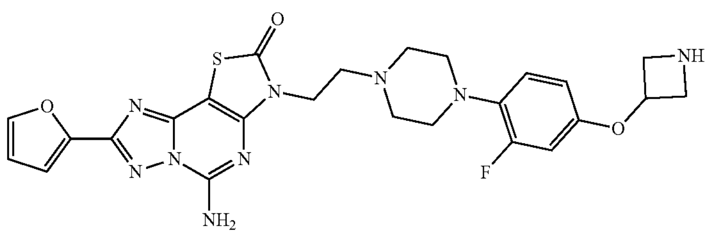 [SMILES: Nc1nc2c(sc(=O)n2CCN2CCN(c3ccc(OC4CNC4)cc3F)CC2)c2nc(-c3ccco3)nn12] | 5-amino-3-(2-(4-(4-(azetidin-3-yloxy)-2-fluorophenyl)piperazin-1-yl)ethyl)-8-(furan-2-yl)thiazolo[5,4-e][1,2,4]triazolo[1,5-c]pyrimidin-2(3H)-one | 551.60 |
| 132 | 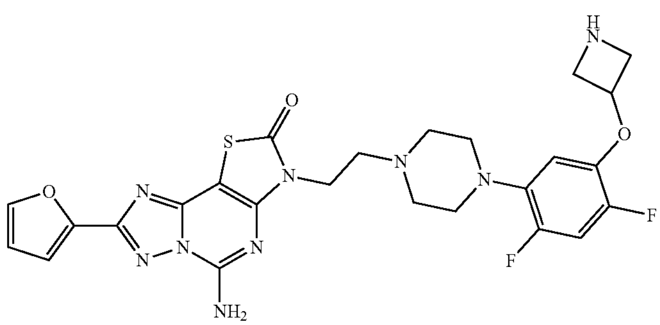 [SMILES: Nc1nc2c(sc(=O)n2CCN2CCN(c3cc(OC4CNC4)c(F)cc3F)CC2)c2nc(-c3ccco3)nn12] | 5-amino-3-(2-(4-(5-(azetidin-3-yloxy)-2,4-difluorophenyl)piperazin-1-yl)ethyl)-8-(furan-2-yl)thiazolo[5,4-e][1,2,4]triazolo[1,5-c]pyrimidin-2(3H)-one | 569.59 |
| 133 | | (S)-5-amino-3-(2-(4-(2,4-difluoro-5-(3-(methylsulfinyl)propoxy)phenyl)piperazin-1-yl)ethyl)-8-(furan-2-yl)thiazolo[5,4-e][1,2,4]triazolo[1,5-c]pyrimidin-2(3H)-one | 618.68 | and pharmaceutically acceptable salts and solvates thereof.

In Table 1, the term "Cpd" means compound.

The compounds of Table 1 were named using ChemBioDraw© Ultra version 12.0 (PerkinElmer).

In one embodiment, the compound of Formula (I) is selected from:
(R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 7);
(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a) and
(−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8b).

In a specific embodiment, the compound of Formula (I) is selected from:
(R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 7); and
(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a).

In preferred embodiment, the compound of Formula (I) is (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a).

In one embodiment, the present invention also relates to enantiomers, salts, solvates, polymorphs, multi-component complexes and liquid crystals of compounds of Formula (I) and subformulae thereof.

In one embodiment, the present invention also relates to polymorphs and crystal habits of compounds of Formula (I) and subformulae thereof, prodrugs and isomers thereof (including optical, geometric and tautomeric isomers) and isotopically-labeled compounds of Formula (I) and subformulae thereof.

The compounds of Formula (I) and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically acceptable salts of the compounds of Formula (I) and subformulae thereof include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, tosylate, esylate and acetate. In a particularly preferred embodiment, the compounds of Formula (I) is under the form of a HCl salt or esylate salt.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula (I) and subformulae thereof may be prepared by one or more of these methods:
(i) by reacting the compound of Formula (I) with the desired acid;
(ii) by reacting the compound of Formula (I) with the desired base;
(iii) by removing an acid- or base-labile protecting group from a suitable precursor of the compound of Formula (I) or by ring-opening a suitable cyclic precursor, for example, a lactone or lactam, using the desired acid; or
(iv) by converting one salt of the compound of Formula (I) to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, esylate, tosylate and the like, can be used as the dosage form.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula (I) above.

The compounds of the invention may be in the form of pharmaceutically acceptable solvates. Pharmaceutically acceptable solvates of the compounds of Formula (I) and subformulae thereof contains stoichiometric or sub-stoichiometric amounts of one or more pharmaceutically acceptable solvent molecule such as ethanol or water. The term "hydrate" refers to when the said solvent is water.

The invention also generally covers all pharmaceutically acceptable predrugs and prodrugs of the compounds of Formula (I) and subformulae thereof.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Pharmaceutical Composition

The invention thus relates to a pharmaceutical composition comprising as pharmaceutically active ingredient an A2A inhibitor, preferably being a thiocarbamate derivative, more preferably a thiocarbamate derivative of formula (I) as described above, and at least one pharmaceutically acceptable carrier, diluent, excipient and/or adjuvant.

In one embodiment, the pharmaceutical composition of the invention comprises an A2A inhibitor, such as a thiocarbamate derivative of formula (I) as described above, and at least one lipid carrier. In one embodiment, the lipid carrier is selected from lauroyl polyoxyl-32 glycerides, D-α-tocopherol-polyethylene glycol-1000 succinate and mixtures thereof. In one embodiment, the lipid carrier is lauroyl polyoxyl-32 glycerides. In another embodiment, the lipid carrier is-α-tocopherol-polyethylene glycol-1000 succinate. In another embodiment, the lipid carrier is a mixture of lauroyl polyoxyl-32 glycerides and D-α-tocopherol-polyethylene glycol-1000 succinate.

In one embodiment, the invention thus provides a pharmaceutical composition comprising:
(a) a compound of Formula (I);

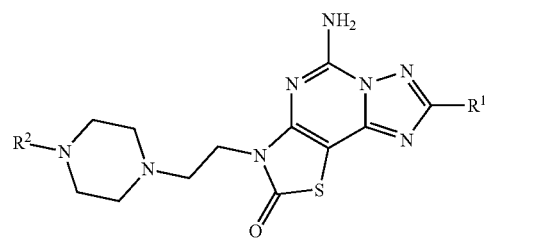

(I)

or a pharmaceutically acceptable salt or solvate thereof, wherein $R^1$ and $R^2$ are as defined above;
(b) a lipid carrier selected from lauroyl polyoxyl-32 glycerides, D-α-tocopherol-polyethylene glycol-1000 succinate and mixtures thereof; and
(c) optionally one or more other pharmaceutically acceptable carrier, diluent, excipient and/or adjuvant.

In one embodiment, the invention provides a pharmaceutical composition comprising:
(a) a compound of Formula (I) or a pharmaceutically acceptable salt or solvate thereof, wherein $R^1$ and $R^2$ are as defined above;
(b) lauroyl polyoxyl-32 glycerides; and
(c) optionally one or more other pharmaceutically acceptable carrier, diluent, excipient and/or adjuvant.

In another embodiment, the invention provides a pharmaceutical composition comprising:
(a) a compound of Formula (I) or a pharmaceutically acceptable salt or solvate thereof, wherein $R^1$ and $R^2$ are as defined above;
(b) D-α-tocopherol-polyethylene glycol-1000 succinate; and
(c) optionally one or more other pharmaceutically acceptable carrier, diluent, excipient and/or adjuvant.

Active Ingredient

The pharmaceutical composition of the invention thus comprises as pharmaceutically active ingredient a compound of Formula (I) or a pharmaceutically acceptable salt or solvate thereof, wherein $R^1$ and $R^2$ are as defined above.

All the embodiment relative to the A2AR inhibitor detailed above apply to the pharmaceutical composition of the invention.

Lipid Carrier

The pharmaceutical composition of the invention comprises a lipid carrier, preferably lauroyl polyoxyl-32 glycerides, D-α-tocopherol-polyethylene glycol-1000 succinate or a mixture thereof.

In one embodiment, the pharmaceutical composition of the invention comprises lauroyl polyoxyl-32 glycerides. This excipient corresponds to Gelucire© 44/14 manufactured by Gattefossé (Saint-Priest—France). This excipient is also known under the following references:
lauroyl polyoxyl-32 glycerides NF/USP (NF: National Formulary; USP: US Pharmacopeia);
lauroyl macrogol-32 glycerides EP (European Pharmacopeia);
hydrogenated coconut PEG-32 esters (INCI);
CAS number 57107-95-6.

Gelucire® 44/14 corresponds to a well-defined multiconstituent substance constituted of mono-, di- and triglycerides and PEG-32 mono- and diesters of lauric acid ($C_{12}$). Gelucire® 44/14 has a melting point ranging from 42.5° C. to 47.5° C. (with a mean at 44° C.) and a hydrophilic/lipophilic balance (HLB) value of 14.

Gelucire® 44/14 is used in order to enhance wetting, dissolution, solubility and bioavailability of the active ingredient.

In another embodiment, the pharmaceutical composition of the invention comprises D-α-tocopherol-polyethylene glycol-1000 succinate. This excipient corresponds to Vitamin E TPGS and is also known under the following references:

D-α-Tocopherol polyethylene glycol-1000 succinate;
Tocophersolan;
Tocofersolan;
VEGS;
α-[4-[[(2R)-3,4-dihydro-2,5,7,8-tetramethyl-2-[(4R,8R)-4,8,12-trimethyltridecyl]-2H-1-benzopyran-6-yl]oxy]-1,4-dioxobutyl]-ω-hydroxy-poly(oxy-1,2-ethanediyl);
Vitamin E PEG succinate;
CAS number 9002-96-4.

Vitamin E TPGS corresponds to a well-defined substance constituted of D-α-Tocopherol (Vitamin E) conjugated to polyethylene glycol 1000 through a succinic acid linker and has a melting point ranging from 37° C. to 41° C. and a hydrophilic/lipophilic balance (HLB) value of 13.

Vitamin E TPGS is used in order to enhance wetting, dissolution, solubility and bioavailability of the active ingredient.

The pharmaceutical composition may comprise Vitamin E TPGS in addition or in place of lauroyl polyoxyl-32 glycerides.

Further Ingredients

The pharmaceutical composition of the invention may optionally comprise one or more other pharmaceutically acceptable carrier, diluent, excipient and/or adjuvant. Such suitable carrier, diluent, excipient and/or adjuvant for use in the preparation of the administration forms will be clear to the skilled person; reference is made to the latest edition of Remington's Pharmaceutical Sciences.

Especially, the pharmaceutical composition of the invention can optionally contain such inactive substances that are commonly used in pharmaceutical formulations, such as for example cosolvents, antioxidants, surfactants, wetting agents, emulsifying agents, buffering agents, pH modifying agents, preserving agents (or preservating agents), isotonifiers, stabilizing agents, granulating agents or binders, precipitation inhibitors, lubricants, disintegrants, glidants, diluents or fillers, adsorbents, dispersing agents, suspending agents, bulking agents, release agents, sweetening agents, flavoring agents, and the like.

According to one embodiment, the pharmaceutical composition of the invention comprises one or more pharmaceutically acceptable inactive ingredients selected from: caprylic acid, polyethylene glycol, propylene glycol, ethanol, glycerol, dimethylsulfoxide, dimethylacetamide, dimethylisosorbide, cellulose derivatives (including hydroxypropylmethylcellulose, methylcellulose, hydroxypropylcellulose, hydroxypropylmethylcellulose phthalate and hydroxypropylmethylcellulose acetate succinate), cremophor RH40 (polyoxyl 40 hydrogenated castor oil), cremophor EL (polyoxyl 35 hydrogenated castor oil), polysorbate 20 (polyoxyethylenesorbitan monolaurate), polysorbate 80 (polyoxyethylenesorbitan monooleate), poloxamer 188 (poly(ethylene glycol)-block-poly(propylene glycol)-block-poly(ethylene glycol)), poloxamer 407 (Poly(ethylene glycol)-block-poly(propylene glycol)-block-poly(ethylene glycol)), vitamin E TPGS (vitamin E polyethylene glycol succinate), solutol HS15 (polyoxyethylated 12-hydroxystearic acid), labrasol (caprylocaproyl polyoxyl-8 glycerides), labrafil M1944 (Oleoyl polyoxyl-6 glycerides), polyvinylpyrrolidone (also called povidone, preferably polyvinylpyrrolidone K17, K19, K29-K32, K90), polyvinylpyrrolidone polyvinylacetate copolymer, polyvinyl caprolactam-polyvinyl acetate-polyethylene glycol graft copolymer (Soluplus®) polylactide polyethylene glycol block copolymer, carboxymethylcellulose (Na/Ca), polyethylene glycol methyl ether-block-poly(D-L-lactide) copolymer, sodium lauryl sulfate, sodium docusate, propylene glycol monolaurate, propylene glycol dilaurate, propylene glycol monocaprylate, polyethylene glycol 660 12-monostearate, poly(butyl methacrylate-co-(2-dimethylaminoethyl) methacrylate-co-methyl methacrylate) 1:2:1, sodium lauryl sulphate.

In a preferred embodiment, the pharmaceutical composition of the invention comprises one or more pharmaceutically acceptable cosolvents. Preferably cosolvents are selected from caprylic acid, polyethylene glycol (PEG), propylene glycol, ethanol, dimethylsulfoxide, dimethylacetamide, dimethylisosorbide and mixtures thereof. In a specific embodiment, the pharmaceutical composition of the invention comprises caprylic acid and/or PEG. Advantageously, when the composition comprises PEG as cosolvent, PEG is of low molecular weight, preferably PEG is PEG 400. In an alternative embodiment, when the composition comprises PEG, it is of a moderate molecular weight, preferably PEG 3350.

In one embodiment, the pharmaceutical composition of the invention further comprises one or more antioxidant; preferably the antioxidant is selected from butylated hydroxytoluene (BHT), butylated hydroxyanisole (BHA), citric acid, sodium metabisulfite, ascorbic acid, methionine and vitamin E; more preferably the antioxidant is BHT.

In some embodiments, surfactants are added, such as for example polyethylene glycols, polyoxyethylene sorbitan fatty acid esters, sorbitan esters, sodium docusate, sodium lauryl sulfate, polysorbates (20, 80, etc.), poloxamers (188, 407 etc.), pluronic polyols, polyoxyethylene sorbitan monoethers (TWEEN©-20, TWEEN-80, etc.), vitamin E TPGS (Vitamin E polyethylene glycol succinate), cremophor RH40 (polyoxyl 40 hydrogenated castor oil), cremophor EL (polyoxyl 35 hydrogenated castor oil), polyethylene glycol 660 12-monostearate, solutol HS15 (Polyoxyethylated 12-hydroxystearic acid), labrasol (caprylocaproyl polyoxyl-8 glycerides), labrafil M1944 (Oleoyl polyoxyl-6 glycerides), polylactide polyethylene glycol block copolymer, polyvinyl caprolactam-polyvinyl acetate-polyethylene glycol graft copolymer (Soluplus®).

In some embodiments, wetting agents are added, such as for example sodium lauryl sulphate, vitamin E TPGS, sodium docusate, polysorbate 80, poloxamer 407. A preferred wetting agent is poloxamer 407.

In some embodiments, emulsifying agents are added, such as for example carbomer, carrageenan, lanolin, lecithin, mineral oil, oleic acid, oleyl alcohol, pectin, poloxamer, polyoxyethylene sorbitan fatty acid esters, sorbitan esters, triethanolamine, propylene glycol monolaurate, propylene glycol dilaurate, propylene glycol monocaprylate. Preferred emulsifying agents are for example poloxamer, propylene glycol monolaurate, propylene glycol dilaurate, and propylene glycol monocaprylate.

In some embodiments, buffering agents are used to help to maintain the pH in the range that approximates physiological conditions Suitable buffering agents include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments, pH modifiers are added, such as for example sodium hydroxide, sodium bicarbonate, magnesium oxide, potassium hydroxide, meglumine, sodium carbonate, citric acid, tartaric acid, ascorbic acid, fumaric acid, succinic acid and malic acid.

In some embodiments, preservatives agents are added to retard microbial growth. Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" are added and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall or helps to inhibit the precipitation, particle growth or agglomeration of the active ingredient. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone; poloxamer 407; cellulose derivatives such as hydroxypropylmethylcellulose, hydroxypropylmethylcellulose phthalate or hydroxypropylmethylcellulose acetate succinate; carboxymethylcellulose (Na/Ca); monosaccharides, such as xylose, mannose, fructose, glucose; disaccharides such as lactose, maltose, sucrose and trisaccacharides such as raffinose; polysaccharides such as dextran; polyethylene glycol methyl ether-block-poly(D-L-lactide) copolymer; poly(butyl methacrylate-co-(2-dimethylaminoethyl) methacrylate-co-methyl methacrylate) 1:2:1. Preferred stabilizers are for example glycerol; polyethylene glycol; polyvinylpyrrolidone; cellulose derivatives such as hydroxypropylmethylcellulose, hydroxypropylmethylcellulose phthalate or hydroxypropylmethylcellulose acetate succinate; carboxymethylcellulose (Na/Ca); polyethylene glycol methyl ether-block-poly(D-L-lactide) copolymer; poly(butyl methacrylate-co-(2-dimethylaminoethyl) methacrylate-co-methyl methacrylate) 1:2:1; polyvinyl caprolactam-polyvinyl acetate-polyethylene glycol graft copolymer and polyvinylpyrrolidone polyvinylacetate copolymer.

In some embodiments granulating agent/binder(s) are added, such as for example starch, gums (inclusive of natural, semisynthetic and synthetic), microcrystalline cellulose, ethyl cellulose, methylcellulose, hydroxypropylcellulose, polymers such as povidone, polyvinylpyrrolidone polyvinylacetate copolymer and the like. Preferred granulating agents are for example methylcellulose, hydroxypropylcellulose, povidone and polyvinylpyrrolidone polyvinylacetate copolymer.

In some embodiments precipitation inhibitors are added, such as for example water soluble derivatives of cellulose including hydroxypropylmethylcellulose and methylcellulose, and water soluble polymers such as polyvinylpyrrolidone, polyvinylpyrrolidone polyvinylacetate copolymer, polyvinyl caprolactam-polyvinyl acetate-polyethylene glycol graft copolymer or poloxaner 407. Preferred precipitation inhibitors are for example hydroxypropylmethylcellulose and polyvinyl caproactam-polyvinyl acetate-polyethylene glycol graft copolymer.

In some embodiments lubricants are added, such as for example magnesium stearate, glyceryl esters, behenoyl polyoxyl-8 glycerides Nf (Compritol HD5 ATO), sodium stearyl fumarate and the like.

In some embodiments disintegrants are added, such as for example synthetics like sodium starch glycolate, cross povidone, cross carmellose sodium, kollidon CL, and natural origin such as locust bean gum and the like.

In some embodiments glidants are added, such as for example talc, magnesium stearate, colloidal silicon dioxide, starch and the like.

In some embodiments diluents (or fillers) are added, such as for example dextrose, lactose, mannitol, microcrystalline cellulose, sorbitol, sucrose, dibasic calcium phosphate, calcium sulphate dehydrate, starch and the like.

In some embodiments adsorbents are added, such as for example silicon dioxide, purified aluminium silicate and the like.

In some embodiments, the pharmaceutical composition of the invention is in the form of tablets and tableting excipients are added, such as for example granulating agents, binders, lubricants, disintegrants, glidants, diluents, adsorbents and the like.

In some embodiments the pharmaceutical composition of the invention is in the form of capsules, in which the capsule shells are constructed from gelatin or from non-animal derived products such as cellulose and its derivatives such as hydroxypropylmethylcellulose. Other ingredients may be included in the capsule shells such as polyethyleneglycol to act as plasticizer; pigments such as titanium dioxide or iron oxide to provide opacity and colour differentiation; lubricants such as carnauba wax; gelling agents such as carrageenan and wetting agents such as sodium lauryl sulphate. In one embodiment, the pharmaceutical composition of the invention is formulated as capsules, wherein the capsule shells are constructed from gelatin and wherein additional components are optionally included in the capsule shells, such as for example polyethylene glycol and sodium lauryl sulphate.

Amounts

In one embodiment, the pharmaceutical composition of the invention comprises an amount of compound of Formula (I) ranging from 1% to 20% in weight to the total weight of the composition (w/w). Preferably the pharmaceutical composition of the invention comprises an amount of compound of Formula (I) ranging from 5% to 15% w/w, preferably from 8% to 12% w/w, more preferably from 9% to 11% w/w, more preferably about 10% w/w.

In one embodiment, the pharmaceutical composition of the invention comprises an amount of lipid carrier ranging from 55% to 99% in weight to the total weight of the composition (w/w). Preferably the pharmaceutical composition of the invention comprises an amount of lipid carrier ranging from 60% to 95% w/w, preferably from 65% to 90% w/w, more preferably from 70% to 90% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w. about 86% w/w, about 87% w/w, about 88% w/w, about 89% w/w, about 90% w/w.

In one embodiment, the pharmaceutical composition of the invention comprises an amount of lauroyl polyoxyl-32 glycerides ranging from 55% to 99% in weight to the total weight of the composition (w/w). Preferably the pharmaceutical composition of the invention comprises an amount of lauroyl polyoxyl-32 glycerides ranging from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w.

In one embodiment, the pharmaceutical composition of the invention comprises an amount of D-α-tocopherol-polyethylene glycol-1000 succinate ranging from 55% to 99% in weight to the total weight of the composition (w/w). Preferably the pharmaceutical composition of the invention comprises an amount of D-α-tocopherol-polyethylene glycol-1000 succinate ranging from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w.

In one embodiment, the pharmaceutical composition of the invention may comprise PEG 400, in an amount ranging from 0% to 30% in weight to the total weight of the composition (w/w). Preferably the pharmaceutical composition of the invention comprises an amount of PEG 400 ranging from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w.

In one embodiment, the pharmaceutical composition of the invention may comprise PEG 3350, in an amount ranging from 0% to 30% in weight to the total weight of the composition (w/w). Preferably the pharmaceutical composition of the invention comprises an amount of PEG 3350 ranging from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w.

In one embodiment, the pharmaceutical composition of the invention may comprise caprylic acid, in an amount ranging from 0% to 20% in weight to the total weight of the composition (w/w). Preferably the pharmaceutical composition of the invention comprises an amount of caprylic acid ranging from 1% to 20% w/w, preferably from 3% to 15% w/w, more preferably from 5% to 10% w/w, more preferably about 5% w/w, about 6% w/w, about 7% w/w, about 8% w/w, about 9% w/w, more preferably about 9% w/w.

In one embodiment, the pharmaceutical composition of the invention may comprise an antioxidant agent, preferably BHT, in an amount ranging from 0% to 5% in weight to the total weight of the composition (w/w). Preferably the pharmaceutical composition of the invention comprises an amount of BHT ranging from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w.

In one embodiment, the pharmaceutical composition of the invention may comprise a wetting agent, preferably sodium lauryl sulphate (SLS), in an amount ranging from 0% to 10% in weight to the total weight of the composition (w/w). Preferably the pharmaceutical composition of the invention comprises an amount of SLS ranging from 0.5% to 5% w/w, preferably from 0.5% to 2% w/w, more preferably from 0.5% to 1.5% w/w, more preferably about 1.0% w/w.

In one embodiment, the pharmaceutical composition of the invention may comprise a precipitation inhibitor, preferably hydroxypropylmethylcellulose, in an amount ranging from 0% to 10% in weight to the total weight of the composition (w/w). Preferably the pharmaceutical composition of the invention comprises an amount of hydroxypropylmethylcellulose ranging from 0.5% to 5% w/w, preferably from 0.5% to 2% w/w, more preferably from 0.5% to 1.5% w/w, more preferably about 1% w/w.

In one embodiment the pharmaceutical composition of the invention may comprise an alternative precipitation inhibitor, preferably polvinyl caprolactaim-polyvinyl acetate-polyethylene glycol graft copolymer in an amount ranging from 0% to 10% in weight to the total weight of the composition (w/w). Preferably the pharmaceutical composition of the invention comprises an amount of polyvinyl caprolactan-polyvinyl acetate-polyethylene glycol graft copolymer ranging from 0.5% to 5% w/w, preferably from 0.5% to 2% w/w, more preferably from 0.5% to 1.5% w/w, more preferably about 1.0% w/w.

In one embodiment the pharmaceutical composition of the invention may comprise an alternative precipitation inhibitor, preferably poloxamer 407 in an amount ranging from 0% to 10% in weight to the total weight of the composition (w/w). Preferably the pharmaceutical composition of the invention comprises an amount of poloxamer 407 ranging from 0.5% to 5% w/w, preferably from 0.5% to 2% w/w, more preferably from 0.5% to 1.5% w/w, more preferably about 1.0% w/w.

In one embodiment the pharmaceutical composition of the invention may comprise an alternative precipitation inhibitor, preferably polyvinylpyrrolidone polyvinyl acetate copolymer in an amount ranging from 0% to 10% in weight to the total weight of the composition (w/w). Preferably the pharmaceutical composition of the invention comprises an amount of polyvinylpyrrolidone polyvinyl aceate ranging from 0.5% to 5% w/w, preferably from 0.5% to 2% w/w, more preferably from 0.5% to 1.5% w/w, more preferably about 1.0% w/w.

In one embodiment, the pharmaceutical composition of the invention comprises: a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w; and b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w.

In one embodiment, the pharmaceutical composition of the invention comprises:
a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;
b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 30% w/w of PEG 400, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and
d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;
b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 30% w/w of PEG 3350, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and
d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;
b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 20% w/w of caprylic acid, preferably from 1% to 20% w/w, preferably from 3% to 15% w/w, more preferably from 5% to 10% w/w, more preferably about 5% w/w, about 6% w/w, about 7% w/w, about 8% w/w, about 9% w/w, more preferably about 9% w/w; and
d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 1% to 20% in weight to the total weight of the composition (w/w) of compound of Formula (I) in the form of a salt, preferably as either the HCl salt or the esylate salt; preferably from 5% to 15% w/w, more preferably from 8% to 12% w/w, more preferably from 9% to 11% w/w, more preferably about 10% w/w;
b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 30% w/w of PEG400, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:

a) from 1% to 20% in weight to the total weight of the composition (w/w) of compound of Formula (I) in the form of a salt, preferably as either the HCl salt or the esylate salt; preferably from 5% to 15% w/w, more preferably from 8% to 12% w/w, more preferably from 9% to 11% w/w, more preferably about 10% w/w;

b) from 55% to 99% w/w of lauroyl polyoxyl-32 glycerides, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;

c) from 0% to 30% w/w of PEG3350, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:

a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w; and b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w.

In one embodiment, the pharmaceutical composition of the invention comprises:

a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;

b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;

c) from 0% to 30% w/w of PEG 400, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:

a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;

b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;

c) from 0% to 30% w/w of PEG 3350, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:

a) from 1% to 20% in weight to the total weight of the composition (w/w) of compound of Formula (I); preferably from 5% to 15% w/w, more preferably from 8% to 12% w/w, more preferably from 9% to 11% w/w, more preferably about 10% w/w;

b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;

c) from 0% to 20% w/w of caprylic acid, preferably from 1% to 20% w/w, preferably from 3% to 15% w/w, more preferably from 5% to 10% w/w, more preferably about 5% w/w, about 6% w/w, about 7% w/w, about 8% w/w, about 9% w/w, more preferably about 9% w/w; and d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 1% to 20% in weight to the total weight of the composition (w/w) of compound of Formula (I) in the form of a salt, preferably as either the HCl salt or the esylate salt; preferably from 5% to 15% w/w, more preferably from 8% to 12% w/w, more preferably from 9% to 11% w/w, more preferably about 10% w/w;
b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 30% w/w of PEG400, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and
d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 1% to 20% in weight to the total weight of the composition (w/w) of compound of Formula (I) in the form of a salt, preferably as either the HCl salt or the esylate salt; preferably from 5% to 15% w/w, more preferably from 8% to 12% w/w, more preferably from 9% to 11% w/w, more preferably about 10% w/w;
b) from 55% to 99% w/w of Vitamin E TPGS, preferably from 60% to 95% w/w, preferably from 65% to 90% w/w, more preferably from 70% to 90% w/w, more preferably about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w;
c) from 0% to 30% w/w of PEG3350, preferably from 5% to 30% w/w, preferably from 10% to 25% w/w, more preferably from 15% to 20% w/w, more preferably about 15% w/w, about 16% w/w, about 17% w/w, about 18% w/w, about 19% w/w, about 20% w/w, more preferably about 18% w/w; and
d) from 0% to 5% w/w of BHT, preferably from 0.001% to 5% w/w, preferably from 0.005% to 1% w/w, more preferably from 0.01% to 0.5% w/w, more preferably about 0.01% w/w, about 0.05% w/w, about 0.10% w/w, about 0.15% w/w, about 0.20% w/w, about 0.25% w/w, about 0.30% w/w, about 0.40% w/w, about 0.50% w/w, more preferably about 0.10% w/w to the total weight of the composition (w/w).

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400; and
d) optionally from 0.01% to 0.5% w/w of BHT.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w of polyvinyl caprolactam-polyvinyl acetate-polyethylene glycol graft copolymer.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w of polyvinyl pyrrolidone polyvinyl acetate copolymer.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350; and
d) optionally from 0.01% to 0.5% w/w of BHT.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of poloxamer 407/In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of polyvinyl caprolactam-polyvinyl acetate-polyethylene glycol graft copolymer.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of polyvinyl pyrrolidone polyvinyl acetate copolymer.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid; and
d) optionally from 0.01% to 0.5% w/w of BHT.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5% to 10% w/w of polyvinyl caprolactam-polyvinyl acetate-polyethylene glycol graft copolymer.

In one embodiment, the pharmaceutical composition of the invention comprises:
a) from 5% to 15% w/w of compound of Formula (I);
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5 to 10% w/w polyvinyl pyrrolidone polyvinyl acetate copolymer In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG400;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG400;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w polyvinyl caprolactam-polyvinyl acetate-polyethylene glycol graft copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG400;
d) optionally from 0.01% to 0.5% w/w of BHT; and
e) optionally from 0.5% to 10% w/w poly % vinyl pyrrolidone polyvinyl acetate copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG3350;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG3350;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w of polyvinyl caprolactam-polyvinyl aceate-polyethylene glycol graft copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 10% to 25% w/w of PEG3350;
d) optionally from 0.01% to 0.5% w/w of BHT; and
e) optionally from 0.5% to 10% w/w polyvinyl pyrrolidone polyvinyl acetate copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 5% to 10% w/w of caprylic acid;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 5% to 10% w/w of caprylic acid;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5% to 10% w/w of polyvinyl caprolactam-polyvinyl aceate-polyethylene glycol graft copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of lauroyl polyoxyl-32 glycerides;
c) from 5% to 10% w/w of caprylic acid;
d) optionally from 0.01% to 0.5% w/w of BHT; and
e) optionally from 0.5% to 10% w/w polyvinyl pyrrolidone polyvinyl acetate copolymer In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG400;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG400;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG400;
d) optionally from 0.01% to 0.5% w/w of BHT; and
e) optionally from 0.5% to 10% w/w of poloxamer 407 In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG400;
d) optionally from 0.01% to 0.5% w/w of BHT; and
e) optionally from 0.5% to 10% w/w polyvinyl caprolactam-polyvinyl acetate-polyethylene glycol graft copolymer In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG400;
d) optionally from 0.01% to 0.5% w/w of BHT; and
e) optionally from 0.5% to 10% w/w polyvinyl pyrrolidone polyvinyl acetate copolymer In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG3350;
d) optionally from 0.01% to 0.5% w/w of BHT;

e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG3350;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG3350;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG3350;
d) optionally from 0.01% to 0.5% w/w of BHT; and
e) optionally from 0.5% to 10% w/w of polyvinyl caprolactam-polyvinyl acetate-polyethylene glycol graft copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 10% to 25% w/w of PEG3350;
d) optionally from 0.01% to 0.5% w/w of BHT; and
e) optionally from 0.5% to 10% w/w polyvinyl pyrrolidone polyvinyl acetate copolymer.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 5% to 10% w/w of caprylic acid;
d) optionally from 0.01% to 0.5% w/w of BHT;
e) optionally from 0.5% to 10% w/w of SLS; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 5% to 10% w/w of caprylic acid;
d) optionally from 0.01% to 0.5% w/w of BHT; and
f) optionally from 0.5% to 10% w/w of hydroxypropylmethylcellulose.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 5% to 10% w/w of caprylic acid;
d) optionally from 0.01% to 0.5% w/w of BHT; and
e) optionally from 0.5% to 10% w/w of poloxamer 407.

In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 5% to 10% w/w of caprylic acid;
d) optionally from 0.01% to 0.5% w/w of BHT; and
e) optionally from 0.5% to 10% w/w of polyvinyl caprolactam-polyvinyl acetate-polyethylene glycol graft copolymer In one embodiment, the pharmaceutical composition of the invention comprises:
a) from 5% to 15% w/w of compound of Formula (I) in the form of a salt, preferably as the HCl salt or the esylate salt;
b) from 70% to 90% w/w of Vitamin E TPGS;
c) from 5% to 10% w/w of caprylic acid;
d) optionally from 0.01% to 0.5% w/w of BHT; and
e) optionally from 0.5% to 10% w/w polyvinyl pyrrolidone polyvinyl acetate copolymer.

Dosage Form

In one embodiment, the pharmaceutical composition of the invention is in a form suitable for oral administration. Such suitable administration form may be solid, semi-solid or liquid. Such suitable administration form will be clear to the skilled person; reference is made to the latest edition of Remington's Pharmaceutical Sciences.

Some preferred, but non-limiting examples of such forms include capsules (including soft and hard gelatin capsules), tablets, pills, powders, lozenges, sachets, cachets, elixirs, suspensions, emulsions, solutions and syrups.

The pharmaceutical composition of the invention is preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Such a unit dosage form can contain for example about 5 mg to about 200 mg of the pharmaceutically active ingredient, preferably about 10 mg to about 100 mg.

The pharmaceutical composition of the invention may also be formulated so as to provide rapid, sustained or delayed release of the active compound(s) contained therein.

Manufacturing of the Pharmaceutical Composition

The pharmaceutical composition of the invention may be manufactured by methods well known by one skilled in the art.

In one embodiment, the pharmaceutical composition of the invention is under solid or semi-solid form. Solid dispersion may be prepared conventionally using methods such as for example fusion (melt), melt granulation, solvent evaporation, spray drying, lyophilization (freeze drying), hotmeltextrusion, electrostatic spinning method, coating on sugar beads using fluidized bed coating system or supercritical fluid technology.

In one embodiment, the pharmaceutical composition of the invention is under the form of capsules, preferably hard gelatin capsules. In such case, the capsules may be manufactured from a common blend using conventional mixing and capsule filling processes according to Good Manufacturing Practice.

In one embodiment, the manufacturing process of the capsules comprises the following steps:
i) lauroyl polyoxyl-32 glycerides is melted at a temperature not less than 50° C. but not exceeding 80° C.;
ii) optionally, further excipients, such as for example caprylic acid, sodium lauryl sulphate, hydroxypropylmethylcellulose, PEG, polyvinyl caprolactam-polyvinyl acetate-polyethylene glycol graft copolymer, polyvinyl pyrrolidone polyvinyl acetate copolymer, ploxomer 407 and/or BHT, are then added to the lauroyl polyoxyl-32 glycerides and mixed together using a suitable mixer; iii) the compound of Formula (I) as either the free base or suitable salt form, preferably the HCl salt or esylate salt, is then added gradually under continuous mixing using a suitable mixer to produce a visually uniform distribution of the drug substance with no observable lumps or agglomerates;

iv) mixing is then continued for at least 30 minutes to ensure that the drug substance is homogeneously distributed as determined visually;

v) the blend is then maintained in the molten state with continued mixing and is filled into appropriately sized gelatin capsule shells to the target capsule fill weight.

As already mention above, the gelatin capsule shells may optionally comprise additional components such as for example polyethylene glycol and sodium lauryl sulphate.

Capsule filling is undertaken using conventional capsule filling methods and equipment suitable for use with molten semi-solid formulations.

In another embodiment, the manufacturing process of the capsules comprises the following steps:

i) Vitamin E TPGS is melted at a temperature not less than 50° C. but not exceeding 80° C.;

ii) optionally, further excipients, such as for example caprylic acid, sodium lauryl sulphate, hydroxypropylmethylcellulose, PEG, polyvinyl caprolactaim-polyvinyl acetate-polyethylene glycol graft copolymer, polyvinyl pyrrolidone polyvinyl acetate copolymer, poloxomer 407 and/or BHT, are then added to the lauroyl polyoxyl-32 glycerides and mixed together using a suitable mixer; iii) the compound of Formula (I) as either the free base or suitable salt form, preferably the HCl salt or esylate salt, is then added gradually under continuous mixing using a suitable mixer to produce a visually uniform distribution of the drug substance with no observable lumps or agglomerates;

iv) mixing is then continued for at least 30 minutes to ensure that the drug substance is homogeneously distributed as determined visually;

v) the blend is then maintained in the molten state with continued mixing and is filled into appropriately sized gelatin capsule shells to the target capsule fill weight.

Dose

Depending on the condition to be prevented or treated and the form of administration, the pharmaceutical composition of the invention may be administered as a single daily dose, divided over one or more daily doses.

In one embodiments, the pharmaceutical composition of the invention is administered in a dose such that it corresponds administering about 5 mg to about 200 mg of the pharmaceutically active ingredient (free base equivalent) to the subject per administration, preferably about 10 mg to about 100 mg.

In one embodiments, an effective dose of the pharmaceutically active ingredient can range from about 0.08 to about 3.3 mg/kg, preferably about 0.15 to about 1.7 mg/kg Uses Another object of this invention is a medicament comprising the pharmaceutical composition of the invention.

The invention is further directed to the use of the pharmaceutical composition of the invention to inhibit A2A receptor.

According to a further feature of the present invention there is provided a method for modulating A2A activity, in a patient, preferably a warm-blooded animal, and even more preferably a human, in need of such treatment, which comprises administering to said patient an effective amount of the pharmaceutical composition of the invention.

According to a further feature of the present invention there is provided the use of the pharmaceutical composition of the invention for the manufacture of a medicament for modulating A2A activity in a patient, in need of such treatment, which comprises administering to said patient an effective amount of the pharmaceutical composition of the invention.

In one embodiment, the invention relates to the use of the pharmaceutical composition of the invention, for increasing immune recognition and destruction of the cancer cells.

The pharmaceutical composition of the invention is therefore useful for the prevention and/or treatment of cancer, especially useful for the treatment of cancer.

The invention further relates to a method for treatment of cancer, which comprises administering to a mammalian species in need thereof a therapeutically effective amount of the pharmaceutical composition of the invention.

The invention further provides the use of the pharmaceutical composition of the invention for the manufacture of a medicament for treating and/or preventing cancer.

The invention also provides for a method for delaying in patient the onset of cancer comprising the administration of a pharmaceutically effective amount of the pharmaceutical composition of the invention to a patient in need thereof.

Preferably, the patient is a warm-blooded animal, more preferably a human.

Various cancers are known in the art. The cancer may be metastatic or non-metastatic. The cancer may be familial or sporadic. In some embodiments, the cancer is selected from the group consisting of: leukemia and multiple myeloma. Additional cancers that can be treated using the methods of the invention include, for example, benign and malignant solid tumors and benign and malignant non-solid tumors. In a specific embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers. In a specific embodiment, the cancer is breast cancer. In a specific embodiment, the cancer is carcinoid cancer. In a specific embodiment, the cancer is cervical cancer. In a specific embodiment, the cancer is colorectal cancer. In a specific embodiment, the cancer is endometrial cancer. In a specific embodiment, the cancer is glioma. In a specific embodiment, the cancer is head and neck cancer. In a specific embodiment, the cancer is liver cancer. In a specific embodiment, the cancer is lung cancer. In a specific embodiment, the cancer is melanoma. In a specific embodiment, the cancer is ovarian cancer. In a specific embodiment, the cancer is pancreatic cancer. In a specific embodiment, the cancer is prostate cancer. In a specific embodiment, the cancer is renal cancer. In a specific embodiment, the cancer is gastric cancer. In a specific embodiment, the cancer is thyroid cancer. In a specific embodiment, the cancer is urothelial cancer.

Examples of solid tumors include, but are not limited to: biliary tract cancer, brain cancer (including glioblastomas and medulloblastomas), breast cancer, carcinoid, cervical cancer, choriocarcinoma, colon cancer, colorectal cancer, endometrial cancer, esophageal cancer, gastric cancer, glioma, head and neck cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, thyroid cancer (including thyroid adenocarcinoma and medullary carcinoma) and urothelial cancer.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

The invention further relates to the use of the pharmaceutical composition of the invention for the prevention and/or treatment of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis.

The invention further relates to a method for treatment or prevention of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis, which comprises administering to a mammalian species in need thereof a therapeutically effective amount of the pharmaceutical composition of the invention.

The invention further provides the use of the pharmaceutical composition of the invention for the manufacture of a medicament for treating and/or preventing radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis.

The invention also provides for a method for delaying in patient the onset of radiation-induced fibrosis, connective tissue diseases (such as for example Sjogrën syndrome, i.e. scleroderma), chronic bacterial infection (such as for example *Helicobacter Pylori*), abnormal scarring (keloids) and polymicrobial sepsis, comprising the administration of a pharmaceutically effective amount of the pharmaceutical composition of the invention to a patient in need thereof.

Combination

The invention also relates to a combination comprising:
 (a) at least one A2A adenosine receptor (A2AR) inhibitor, and
 (b) at least one anticancer agent.

In a preferred embodiment, the invention provides a combination comprising:
 (a) at least one A2AR inhibitor being a thiocarbamate derivative, more preferably a thiocarbamate derivative of Formula (I)

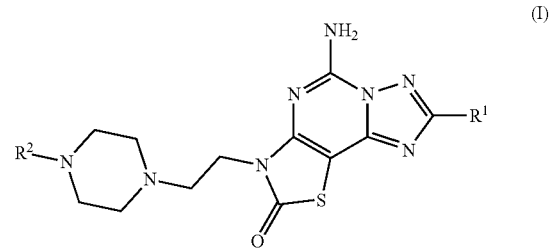

or a pharmaceutically acceptable salt or solvate thereof, wherein $R^1$ and $R^2$ are as defined above; and
 (b) at least one anticancer agent.

As detailed below, the anticancer agent may be selected from immunotherapeutic agents, chemotherapeutic agents, antiangiogenic agents, multidrug resistance-associated proteins inhibitors, radiotherapeutic agents, and any combination thereof.

In the context of the present invention the term "combination" preferably means a combined occurrence of an A2AR inhibitor and of an anticancer agent. Therefore, the combination of the invention may occur either as one composition, comprising all the components in one and the same mixture (e.g. a pharmaceutical composition), or may occur as a kit of parts, wherein the different components form different parts of such a kit of parts. The administration of the A2AR inhibitor and of the anticancer agent may occur either simultaneously or timely staggered, with similar or different timing of administration (i.e. similar or different numbers of administration of each component), either at the same site of administration or at different sites of administration, under similar of different dosage forms.

The invention is based on the surprising finding that the combination of an A2AR inhibitor and an anticancer agent (such as for example an immunotherapeutic agent, especially a checkpoint inhibitor), shows an extremely advantageous inhibition of tumor growth and/or reduction in the number of cancer cells, resulting in enhanced survival which could not be expected from the prior art. Thus, the combined treatment with an A2AR inhibitor and with an anticancer agent, could strongly decrease the harmful impact of a disease to be treated, e.g. the growth rate of a tumor. These effects are illustrated in the Examples hereinafter.

A2AR inhibitor

As a first component, the combination of the invention includes an A2AR inhibitor. Preferably, the A2AR inhibitor is a thiocarbamate derivative, especially a thiocarbamate derivative as those disclosed in PCT/EP2018/058301. More preferably the A2AR inhibitor is a thiocarbamate derivative of formula (I) as described above.

In a preferred embodiment, the combination of the invention thus comprises as A2AR inhibitor a compound of Formula (I):

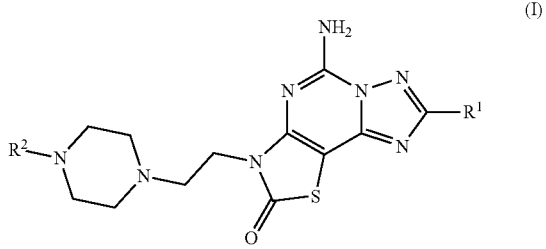

or a pharmaceutically acceptable salt or solvate thereof, wherein $R^1$ and $R^2$ are as defined above.

All the embodiment relative to the A2AR inhibitor detailed above apply to the combination of the invention.

Anticancer Agent

As a second component, the combination of the invention includes at least one anticancer agent.

In one embodiment, the anticancer agent is selected from immunotherapeutic agents, chemotherapeutic agents, antiangiogenic agents, multidrug resistance-associated proteins inhibitors, radiotherapeutic agents, and any combination thereof.

In one embodiment, the combination of the invention comprises a single anticancer agent. In another embodiment, the combination of the invention comprises a plurality of anticancer agents; preferably two, three or four anticancer agents as defined below. In case of use of a combination of anticancer agents in the combination of the invention, the anticancer agents may be of the same class of agents or of different classes of agents. For example, a combination of an immunotherapeutic agent and of a chemotherapeutic agent may be used with the A2AR inhibitor.

Immunotherapeutic Agent

In one embodiment, the combination of the invention includes an immunotherapeutic agent as anticancer agent.

In such case the invention relates to a combination comprising:
(a) at least one A2A adenosine receptor (A2AR) inhibitor, and
(b) at least one immunotherapeutic agent.

In a preferred embodiment, the invention provides a combination comprising:
(a) at least one A2AR inhibitor being a thiocarbamate derivative, more preferably a thiocarbamate derivative of Formula (I) or a pharmaceutically acceptable salt or solvate thereof, wherein $R^1$ and $R^2$ are as defined above; and
(b) at least one immunotherapeutic agent.

In the present invention, "immunotherapy" refers to a therapy aiming at inducing and/or enhancing an immune response towards a specific target, for example towards cancer cells. In such last case, it is referred to as cancer immunotherapy.

The immunotherapeutic agent is for example selected from checkpoint inhibitors, checkpoint agonists (also called T-cell agonists), IDO inhibitors, PI3K inhibitors, adenosine receptor inhibitors, adenosine-producing enzymes inhibitors, CD40 agonists, IL2 variants, immune cells (for conducting adoptive transfer), therapeutic vaccines, and combinations thereof. In a specific embodiment, the immunotherapeutic agent is a checkpoint inhibitor.

In one embodiment, the immunotherapeutic agent to be combined with the A2AR inhibitor of Formula (I) as described hereinabove comprises or consists of checkpoint inhibitors, checkpoint agonists, IDO inhibitors, PI3K inhibitors, adenosine receptor inhibitors, adenosine-producing enzymes inhibitors, CD40 agonists, IL2 variants, immune cells (for conducting adoptive transfer), therapeutic vaccines, or any mixes thereof.

In the context of the present invention the term "combination" preferably means a combined occurrence of an A2AR inhibitor and of an immunotherapeutic agent. Therefore, the combination of the invention may occur either as one composition, comprising all the components in one and the same mixture (e.g. a pharmaceutical composition), or may occur as a kit of parts, wherein the different components form different parts of such a kit of parts. The administration of the A2AR inhibitor and of the immunotherapeutic agent may occur either simultaneously or timely staggered, with similar or different timing of administration (i.e. similar or different numbers of administration of each component), either at the same site of administration or at different sites of administration, under similar of different dosage forms. Such combination may induce an active immune response and thereby prevents e.g. tumor growth or induces tumor regression.

Checkpoint Inhibitors

In one embodiment, the combination of the invention includes at least one checkpoint inhibitor as immunotherapeutic agent.

Checkpoint inhibitors (CPI), that may also be referred to as immune checkpoint inhibitors (ICI), block the interactions between inhibitory receptors expressed on T cells and their ligands. As a cancer treatment, the use of checkpoint inhibitor aims at preventing the activation of inhibitory receptors expressed on T cells by ligands expressed by the tumor cells. The use of checkpoint inhibitors thus aims at preventing the inhibition of T cells present in the tumor, i.e., tumor infiltrating T cells, and thus at enhancing the subject immune response towards the tumor cells.

Thus, the combination of the invention can restore immune functions in tumor environments by using as a first component an A2AR inhibitor, and to antagonize checkpoint pathway signaling by preferably inhibiting or suppressing signal transduction by using as second component a checkpoint inhibitor as immunotherapeutic agent.

Examples of checkpoint inhibitors include, without being limited to:
  inhibitors of the cell surface receptor PD-1 (programmed cell death protein 1), also known as CD279 (cluster differentiation 279);
  inhibitors of the ligand PD-L1 (programmed death-ligand 1), also known as CD274 (cluster of differentiation 274) or B7-H1 (B7 homolog 1);
  inhibitors of the cell surface receptor CTLA4 or CTLA-4 (cytotoxic T-lymphocyte-associated protein 4), also known as CD152 (cluster of differentiation 152);
  inhibitors of LAG-3 (lymphocyte-activation gene 3), also known as CD223 (cluster differentiation 223);
  inhibitors of TIM-3 (T-cell immunoglobulin and mucin-domain containing-3), also known as HAVCR2 (hepatitis A virus cellular receptor 2) or CD366 (cluster differentiation 366);
  inhibitors of TIGIT (T cell immunoreceptor with Ig and ITIM domains), also known as VSIG9 (V-Set And Immunoglobulin Domain-Containing Protein 9) or VSTM3 (V-Set And Transmembrane Domain-Containing Protein 3);

inhibitors of BTLA (B and T lymphocyte attenuator), also known as CD272 (cluster differentiation 272);

inhibitors of CEACAM-1 (carcinoembryonic antigen-related cell adhesion molecule 1) also known as CD66a (cluster differentiation 66a); and inhibitors of GITR (glucocorticoid-induced TNFR-related protein) also known as TNFRSF18 (tumor necrosis factor receptor superfamily member 18) or AITR (activation-inducible TNFR family receptor).

In one embodiment, the checkpoint inhibitor is selected from the group comprising or consisting of inhibitors of PD-1, inhibitors of PD-L1, inhibitors of CTLA4, inhibitors of LAG-3, inhibitors of TIM-3, inhibitors of TIGIT, inhibitors of BTLA, inhibitors of CEACAM-1, inhibitors of GITR and any mixtures thereof.

In one embodiment, the checkpoint inhibitor is selected from the group comprising or consisting of inhibitors of PD-1, inhibitors of PD-L1, inhibitors of CTLA-4, inhibitors of TIGIT and any mixtures thereof.

In one embodiment, the checkpoint inhibitor is selected from the group comprising or consisting of inhibitors of PD-1, inhibitors of PD-L1, inhibitors of CTLA-4 and any mixtures thereof.

In one embodiment, the checkpoint inhibitor is an inhibitor of PD-1, also referred to as an anti-PD-1. Inhibitors of PD-1 may include antibodies targeting PD-1, in particular monoclonal antibodies, and non-antibody inhibitors such as small molecule inhibitors.

Examples of inhibitors of PD-1 include, without being limited to, pembrolizumab, nivolumab, cemiplimab, tislelizumab, spartalizumab, ABBV-181, JNJ-63723283, BI 754091, MAG012, TSR-042, AGEN2034. Pembrolizumab is also known as MK-3475, MK03475, lambrolizumab, or SCH-900475. The trade name of pembrolizumab is Keytruda®. Nivolumab is also known as ONO-4538, BMS-936558, MDX1106, or GTPL7335. The trade name of nivolumab is Opdivo®. Cemiplimab is also known as REGN2810 or REGN-2810. Tislelizumab is also known as BGB-A317. Spartalizumab is also known as PDR001 or PDR-001.

In one embodiment, the checkpoint inhibitor is selected from the group comprising or consisting of pembrolizumab, nivolumab, cemiplimab, tislelizumab, spartalizumab, ABBV-181, JNJ-63723283, BI 754091, MAG012, TSR-042, AGEN2034, and any mixtures thereof.

In one embodiment, the checkpoint inhibitor is an inhibitor of PD-L1, also referred to as an anti-PD-L1. Inhibitors of PD-L1 may include antibodies targeting PD-L1, in particular monoclonal antibodies, and non-antibody inhibitors such as small molecule inhibitors.

Examples of inhibitors of PD-L1 include, without being limited to, avelumab, atezolizumab, durvalumab and LY3300054. Avelumab is also known as MSB0010718C, MSB-0010718C, MSB0010682, or MSB-0010682. The trade name of avelumab is Bavencio. Atezolizumab is also known as MPDL3280A (clone YW243.55.70), MPDL-3280A, RG-7446 or RG7446. The trade name of atezolizumab is Tecentriq®. Durvalumab is also known as MEDI4736 or MEDI-4736. The trade name of durvalumab is Imfinzi®.

In one embodiment, the checkpoint inhibitor is selected from the group comprising or consisting of avelumab, atezolizumab, durvalumab, LY3300054, and any mixtures thereof.

In one embodiment, the checkpoint inhibitor is an inhibitor of CTLA-4, also referred to as an anti-CTLA-4.

Inhibitors of CTLA-4 may include antibodies targeting CTLA-4, in particular monoclonal antibodies, and non-antibody inhibitors such as small molecule inhibitors.

Examples of inhibitors of CTLA-4 include, without being limited to, ipilimumab and tremelimumab. Ipilimumab is also known as BMS-734016, MDX-010, or MDX-101. The trade name of ipilimumab is Yervoy®. Tremelimumab is also known as ticilimumab, CP-675, or CP-675,206.

In one embodiment, the at least one checkpoint inhibitor is selected from the group comprising or consisting of ipilimumab, tremelimumab, and any mixtures thereof.

In one embodiment, the checkpoint inhibitor is an inhibitor of TIGIT, also referred to as an anti-TIGIT.

In one embodiment of various methods, pharmaceutical compositions, kits, or uses provided herein, the anti-human TIGIT monoclonal antibody or antigen binding fragment thereof is BMS-986207 (Bristol-Myers Squibb, New York, N.Y.).

In another embodiment of various methods, pharmaceutical compositions, kits, or uses provided herein, the anti-human TIGIT monoclonal antibody or antigen binding fragment thereof is OMP-313M32 (OncoMed Pharmaceuticals, Redwood city, CA).

In another embodiment of various methods, pharmaceutical compositions, kits, or uses provided herein, the anti-human TIGIT monoclonal antibody or antigen binding fragment thereof MK-7684 (Merck & Co., Kenilworth, N.J.).

In yet another embodiment of various methods, pharmaceutical compositions, kits, or uses provided herein, the anti-human TIGIT monoclonal antibody or antigen binding fragment thereof is MTIG7192A (also known as RG6058, U.S. Publ. No. 2017/0088613).

In still another embodiment of various methods, pharmaceutical compositions, kits, or uses provided herein, the anti-human TIGIT monoclonal antibody or antigen binding fragment thereof is PTZ-201 (Potenza Therapeutics, Cambridge, Mass.; also known as ASP8374, Astellas Pharma, Tokyo, Japan).

In another embodiment of various methods, pharmaceutical compositions, kits, or uses provided herein, the anti-human TIGIT monoclonal antibody or antigen binding fragment thereof COM902 (Compugen LTD, Holon, Ill.).

In yet another embodiment of various methods, pharmaceutical compositions, kits, or uses provided herein, the anti-human TIGIT monoclonal antibody or antigen binding fragment thereof is described in WO2018/160704 (Seattle Genetics, Seattle, Wash.).

In yet another embodiment of various methods, pharmaceutical compositions, kits, or uses provided herein, the anti-human TIGIT monoclonal antibody or antigen binding fragment thereof is described in WO2019/023504 (Iteos Therapeutics). In certain preferred embodiments, the anti-human TIGIT antibody or antigen binding fragment comprises a combination of HCDR1, HCDR2, HCDR3, LCDR1, LCDR2 and LCDR3, wherein:

HCDR1 comprises or consists of SEQ ID NO: 1 (YTFTSYYMH),

HCDR2 comprises or consists of SEQ ID NO: 2 (VIGPSGASTSYAQKFQG),

HCDR3 comprises or consists of SEQ ID NO: 3 (ARDHSDYWSGIMEV),

LCDR1 comprises or consists of SEQ ID NO: 4 (RASQSVRSSYLA),

LCDR2 comprises or consists of SEQ ID NO: 5 (GASSRAT), and

LCDR3 comprises or consists of SEQ ID NO: 6 (QQYFSPPWT).

Checkpoint Agonists (T-Cell Agonists)

In one embodiment, the combination of the invention includes at least one checkpoint agonist (also referred to as T-cell agonist) as immunotherapeutic agent.

T-cell agonists act by activating stimulatory receptors expressed on immune cells, such as T cells. As used herein, the term "stimulatory receptors" refer to receptors that induce a stimulatory signal upon activation, and thus lead to an enhancement of the immune response. As a cancer treatment, T-cell agonist therapy aims at activating stimulatory receptors expressed on immune cells present in a tumor. In particular, T-cell agonist therapy aims at enhancing the activation of T cells present in a tumor, i.e., tumor infiltrating T cells, and thus at enhancing the subject immune response towards the tumor cells.

Examples of T-cell agonists include, without being limited to:
  agonists of CD137 (cluster differentiation 137) also known as 4-1BB or TNFRS9 (tumor necrosis factor receptor superfamily, member 9);
  agonists of OX40 receptor also known as CD134 (cluster differentiation 134) or TNFRSF4 (tumor necrosis factor receptor superfamily, member 4).

In one embodiment, the checkpoint agonist is selected from the group comprising or consisting of agonists of CD137, agonists of OX40 and any mixtures thereof.

Examples of agonists of CD137 include, without being limited, utomilumab and urelumab.

IDO Inhibitors

In one embodiment, the combination of the invention includes at least one inhibitor of indoleamine-2,3-dioxygenase (IDO) as immunotherapeutic agent.

Indoleamine 2,3-dioxygenase enzyme catalyzes the first and rate-limiting step of L-tryptophan (Trp) catabolism. IDO is implicated in immune modulation through its ability to limit T cell function and engage mechanisms of immune tolerance. IDO activity in tumor cells serves to impair anti-tumor responses. Inhibiting IDO thus enables to restore tumor immune surveillance.

Examples of IDO inhibitors include beta-carboline (also known as norharmane), rosmarinic acid, 1-methyl-L-tryptophan (also known as L-1-MT), epacadostat, navoximod or those disclosed in WO2015/173764, and more preferably those of formula II, II' or II'.

In a preferred embodiment, the IDO inhibitor is selected among those disclosed in WO2015/173764, and more preferably those of formula II, II' or II".

PI3K Gamma Inhibitors

In one embodiment, the combination of the invention includes at least one PI3K inhibitor as immunotherapeutic agent.

A phosphoinositide 3-kinase inhibitor (PI3K inhibitor) is a class of medical drug that functions by inhibiting one or more of the phosphoinositide 3-kinase enzymes, which are part of the PI3K/AKT/mTOR pathway, an important signaling pathway for many cellular functions such as growth control, metabolism and translation initiation. Many types of cancers have activated PI3K pathway, which prohibit tumor cells from cell death.

There are a number of different classes and isoforms of PI3Ks. Class 1 PI3Ks have a catalytic subunit known as p110, with four types (isoforms)-p110 alpha, p110 beta, p110 gamma and p110 delta.

In a preferred embodiment, the PI3K inhibitor is a PI3K-gamma inhibitor.

Examples of PI3K inhibitors include wortmannin, LY294002, demethoxyviridon, hibiscone C, Idelalisib, Copanlisib, Duvelisib, Taselisib, Buparlisib, Alpelisib, Umbralisib, Dactolisib, Voxtalisib, IPI-549, RP6530, IC87114 and TG100-115.

Examples of PI3K-gamma inhibitors include Copanlisib, Duvelisib, IPI-549, RP6530, IC87114 and TG100-115.

Adenosine Receptor Inhibitor

In one embodiment, the combination of the invention includes at least one further inhibitor of adenosine receptors as immunotherapeutic agent.

As mentioned in the introduction, the adenosine receptors are a class of purinergic G protein-coupled receptors with adenosine as endogenous ligand. There are four known types of adenosine receptors in humans: A1, A2A, A2B and A3.

The combination of the invention comprises as first component an inhibitor of A2A receptor, of formula (I) as defined above. The second component of the combination may be a further inhibitor of an adenosine receptor, especially an inhibitor of A1, A2A, A2B or A3 receptors. Preferably the second component of the combination of the invention is an inhibitor of A2B receptor or an inhibitor of A3 receptor.

Examples of inhibitors of A2B receptor include ATL-801, CVT-6883, MRS-1706, MRS-1754, OSIP-339,391, PSB-603, PSB-0788 and PSB-1115.

Examples of inhibitors of A3 receptor include KF-26777, MRS-545, MRS-1191, MRS-1220, MRS-1334, MRS-1523, MRS-3777, MRE-3005-F20, MRE-3008-F20, PSB-11, OT-7999, VUF-5574 and SSR161421.

Adenosine-Producing Enzymes Inhibitors

In one embodiment, the combination of the invention includes at least one adenosine-producing enzymes inhibitor as immunotherapeutic agent.

Ectonucleotidases are families of nucleotide metabolizing enzymes that metabolize nucleotides to nucleosides. Subfamilies of ectonucleotidases include: CD39/NTPDases (ecto-nucleotide triphosphate diphosphohydrolases), nucleotide pyrophosphatase/phosphodiesterase (NPP)-type ecto-phosphodiesterases, alkaline phosphatases and ecto-5'-nucleotidases/CD73.

Among other functions, ectonucleotidases generate extracellular adenosine, the first step involving the conversion of ATP/ADP to AMP, carried out by ENTPD1, also known as CD39. The second step involves the conversion of AMP to adenosine. It is carried out by NT5E, also known as CD73. Thus ectonucleotidases are adenosine-producing enzymes.

As mentioned in the introduction, high levels of extracellular adenosine play a significant role in the evasion of antitumor immune response. Thus using inhibitors of adenosine-producing enzymes, by enabling to reduce extracellular adenosine levels is beneficial in cancer therapy.

Examples of adenosine-producing enzymes inhibitors include:
  inhibitors of CD39, also known as ENTPD1 or Ecto-nucleoside triphosphate diphosphohydrolases (EC 3.6.1.5, apyrase),
  inhibitors of CD73, also known as 5'-nucleotidase (5'-NT) or ecto-5'-nucleotidase or NT5E,
  inhibitors of Ecto-nucleotide pyrophosphatase/PDEs (EC 3.6.1.9 and EC 3.1.4.1) and
  inhibitors of alkaline phosphatases (APs; EC 3.1.3.1),
  inhibitors of CD38, also known as cyclic ADP ribose hydrolase or ADP-ribosyl cyclase/cyclic ADP-ribose (cADPR) hydrolase).

Examples of adenosine-producing enzymes inhibitors include IPH5201, A001485, SRF617, ARL67156, POM-1, IPH5301, A000830, A001190, A001421, SRF373/NZV930, Darutumumab. More precisely, examples of CD39 inhibitors include IPH5201, A001485, SRF617, ARL67156 and POM-1; examples of CD73 inhibitors include IPH5301, A000830, A001190, A001421 and SRF373/NZV930; and examples of CD38 inhibitors include Darutumumab.

CD40 Agonists

In one embodiment, the combination of the invention includes at least one CD40 agonist as immunotherapeutic agent.

CD40 is a cell surface receptor member of the tumor necrosis factor (TNF) receptor superfamily. It mediates both indirect tumor cell killing through the activation of the immune system and direct tumor cell apoptosis. Similar to the endogenous CD40 ligand (CD40L or CD154), CD40 agonists bind to CD40 on a variety of immune cell types. This triggers the cellular proliferation and activation of antigen-presenting cells (APCs), and activates B-cells, and effector and memory T-cells. This results in an enhanced immune response against tumor cells.

Examples of CD40 agonists include CD40 agonistic antibodies and recombinant CD40 agonists (ie proteins, but not antibodies). Examples of CD40 agonistic antibodies include selicrelumab (formely known as RO7009789 and CP-870, 893), APX005M, JNJ-64457107 (formerly ADC-1013), SEA-CD40, ChiLob 7/4, CDX-1140H, dacetuzumab (SGN-40) and ABBV-428. Examples of recombinant CD40 agonists include MEDI5083 and HERA-CD40L.

IL2 Variants

In one embodiment, the combination of the invention includes at least one IL2 variant as immunotherapeutic agent.

Interleulin-2 (IL-2) is a powerful immune growth factor that plays an important role in sustaining T cell response. The potential of IL-2 in expanding T cells without loss of functionality has led to its early use in cancer immunotherapy.

Examples of IL2 variants include recombinant, PEGylated and/or mutated IL2 variants, such as for example aldesleukin, monomethoxy PEG IL2, NKTR-214, MDNA-109, RO6874281 and ALKS-4230.

Immune Cells—Adoptive Cell Transfer

According to one embodiment, the immunotherapeutic agent is immune cells to be used in an adoptive transfer of cells, also referred to as adoptive cell therapy (both also referred to as ACT), particularly an adoptive transfer of T cells, also referred to as adoptive T cell therapy.

As used herein, an adoptive transfer of cells or adoptive cell therapy is defined as the transfer, for example as an infusion, of immune cells to a subject. As a cancer treatment, the adoptive transfer of immune cells to a subject aims at enhancing the subject immune response towards the cancer cells.

In one embodiment, the immune cells are T cells, in particular effector T cells. Examples of effector T cells include $CD4^+$ T cells and $CD8^+$ T cells.

In one embodiment, the transferred T cells are cytotoxic cells. Examples of cytotoxic T cells include $CD8^+$ T cells and natural killer (NK) cells, in particular natural killer (NK) T cells.

In one embodiment, the transferred immune cells as described hereinabove are antigen-specific cells. In one embodiment, the transferred immune cells as described hereinabove are antigen-specific immune cells, wherein said antigen is specifically and/or abundantly expressed by cancer cells. In one embodiment, the transferred immune cells as described hereinabove are cancer-specific immune cells, in other words the transferred immune cells as described hereinabove specifically recognize cancer cells through an antigen specifically and/or abundantly expressed by said cancer cells. In one embodiment, the transferred immune cells as described hereinabove are cancer-specific effector T cells. In one embodiment, the transferred immune cells as described hereinabove are cancer-specific $CD8^+$ effector T cells, in particular cancer-specific cytotoxic $CD8^+$ T cells. In one embodiment, the transferred immune cells as described hereinabove are cancer-specific cytotoxic cells. In one embodiment, the transferred immune cells as described hereinabove are cancer-specific NK cells. In one embodiment, the transferred immune cells as described hereinabove are tumor-specific immune cells, in other words the transferred immune cells as described hereinabove specifically recognize tumor cells through an antigen specifically and/or abundantly expressed by said tumor cells. In one embodiment, the transferred immune cells as described hereinabove are tumor-specific effector T cells. In one embodiment, the transferred immune cells as described hereinabove are tumor-specific $CD8^+$ effector T cells, in particular tumor-specific cytotoxic $CD8^+$ T cells. In one embodiment, the transferred immune cells as described hereinabove are tumor-specific cytotoxic cells. In one embodiment, the transferred immune cells as described hereinabove are tumor-specific NK cells.

In one embodiment, the transferred immune cells as described hereinabove are autologous immune cells, in particular autologous T cells. In another embodiment, the transferred immune cells as described hereinabove are allogenic (or allogenous) immune cells, in particular allogenic NK cells.

Methods to isolate T cells from a subject, in particular antigen-specific T cells, e.g., tumor-specific T cells, are well-known in the art (see for example Rosenberg & Restifo, 2015, Science 348, 62-68; Prickett et al., 2016, Cancer Immunol Res 4, 669-678; or Hinrichs & Rosenberg, 2014, Immunol Rev 257, 56-71). Methods to expand T cells ex vivo are well-known in the art (see for example Rosenberg & Restifo, 2015, Science 348, 62-68; Prickett et al., 2016, Cancer Immunol Res 4, 669-678; or Hinrichs & Rosenberg, 2014, Immunol Rev 257, 56-71). Protocols for infusion of T cells in a subject, including pre-infusion conditioning regimens, are well-known in the art (see for example Rosenberg & Restifo, 2015, Science 348, 62-68; Prickett et al., 2016, Cancer Immunol Res 4, 669-678; or Hinrichs & Rosenberg, 2014, Immunol Rev 257, 56-71).

In one embodiment, the immune cells are CAR immune cells, in particular a CAR T cells, in the context respectively of CAR immune cell therapy and CAR T cell therapy.

As used herein, CAR immune cell therapy is an adoptive cell therapy wherein the transferred cells are immune cells as described hereinabove, such as T cells or NK cells, genetically engineered to express a chimeric antigen receptor (CAR). As a cancer treatment, the adoptive transfer of CAR immune cells to a subject aims at enhancing the subject immune response towards the cancer cells.

CARs are synthetic receptors consisting of a targeting moiety that is associated with one or more signaling domains in a single fusion molecule or in several molecules. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are usually derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Thus, signaling domains from co-stimulatory molecules including CD28, OX-40 (CD134), and 4-1BB (CD137) have been added alone (second generation) or in combination (third generation) to enhance survival and increase proliferation of CAR modified T cells.

Thus, in one embodiment, the transferred T cells as described hereinabove are CAR T cells. The expression of a CAR allows the T cells to be redirected against a selected antigen, such as an antigen expressed at the surface of cancer cells. In one embodiment, the transferred CAR T cells recognize a tumor-specific antigen.

In another embodiment, the transferred NK cells as described hereinabove are CAR NK cells. The expression of a CAR allows the NK cells to be redirected against a selected antigen, such as an antigen expressed at the surface of cancer cells. In one embodiment, the transferred CAR NK cells recognize a tumor-specific antigen.

In one embodiment, the CAR immune cells as described hereinabove are autologous CAR immune cells, in particular autologous CAR T cells. In another embodiment, the CAR immune cells as described hereinabove are allogenic (or allogenous) CAR immune cells, in particular allogenic CAR NK cells.

Therapeutic Vaccines

According to one embodiment, the immunotherapeutic agent is a therapeutic vaccine (sometimes also referred to as a treatment vaccine).

As used herein, a therapeutic vaccine is defined as the administration of at least one tumor-specific antigen (e.g., synthetic long peptides or SLP), or of the nucleic acid encoding said tumor-specific antigen; the administration of recombinant viral vectors selectively entering and/or replicating in tumor cells; the administration of tumor cells; and/or the administration of immune cells (e.g., dendritic cells) engineered to present tumor-specific antigens and trigger an immune response against these antigens.

As a cancer treatment, therapeutic vaccines aim at enhancing the subject immune response towards the tumor cells.

Examples of therapeutic vaccines aiming at enhancing the subject immune response towards the tumor cells include, without being limited to, viral-vector based therapeutic vaccines such as adenoviruses (e.g., oncolytic adenoviruses), vaccinia viruses (e.g., modified vaccinia Ankara (MVA)), alpha viruses (e.g., Semliki Forrest Virus (SFV)), measles virus, Herpes simplex virus (HSV), and coxsackievirus; synthetic long peptide (SLP) vaccines; and dendritic cell vaccines.

Chemotherapeutic Agent

In one embodiment, the combination of the invention includes at least one chemotherapeutic agent as anticancer agent.

The chemotherapeutic agent is for example selected from anticancer alkylating agents, anticancer antimetabolites, anticancer antibiotics, plant-derived anticancer agents, anticancer platinum coordination compounds, Parp inhibitors, anti-hormone-sensitive cancer agents and any combination thereof.

In one embodiment, the chemotherapeutic agent to be combined with the A2AR inhibitor of Formula (I) as described hereinabove comprises or consists of anticancer alkylating agents, anticancer antimetabolites, anticancer antibiotics, plant-derived anticancer agents, anticancer platinum coordination compounds, Parp inhibitors, anti-hormone-sensitive cancer agents and any combination thereof.

Anticancer Alkylating Agent

In one embodiment, the combination of the invention includes at least one anticancer alkylating agent as chemotherapeutic agent.

An anticancer alkylating agent refers to an alkylating agent having anticancer activity, and the term "alkylating agent" herein generally refers to an agent giving an alkyl group in the alkylation reaction in which a hydrogen atom of an organic compound is substituted with an alkyl group.

Examples of anticancer alkylating agents include nitrogen mustard N-oxide, cyclophosphamide, ifosfamide, melphalan, busulfan, mitobronitol, carboquone, thiotepa, rammustine, nimustine, temozolomide and carmustine.

Anticancer Antimetabolite

In one embodiment, the combination of the invention includes at least one anticancer antimetabolite as chemotherapeutic agent.

An anticancer antimetabolite refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides).

Examples of anticancer antimetabolites include methotrexate, 6-mercaptopurine riboside, mercaptopurine, 5-fluorouracil (also called "5-FU"), tegafur, doxifluridine, carmofur, cytarabine, cytarabine ocfosfate, enocitabine, S-1, gemcitabine, fludarabine and pemetrexed disodium. Preferably the anticancer antimetabolite is selected from 5-FU, gemcitabine and pemetrexed.

Anticancer Antibiotic

In one embodiment, the combination of the invention includes at least one anticancer antibiotic as chemotherapeutic agent.

An "anticancer antibiotic" refers to an antibiotic having anticancer activity, and the "antibiotic" herein includes substances that are produced by microorganisms or by partial or total synthesis, and derivatives thereof; and inhibit cell growth and other functions of microorganisms and of other living organisms.

Examples of anticancer antibiotic include actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus and valrabicin. Preferably, thenanticancer antibiotic is doxorubicin.

Plant-Derived Anticancer Agent

In one embodiment, the combination of the invention includes at least one plant-derived anticancer agent as chemotherapeutic agent.

A "plant-derived anticancer agent" as used in the specification includes compounds having anticancer activities which originate from plants, or compounds prepared by applying chemical modification to the foregoing compounds.

Examples of plant-derived anticancer agent include vincristine, vinblastine, vindesine, etoposide, sobuzoxane, docetaxel, paclitaxel, nab-paclitaxel and vinorelbine. Preferably, the plant-derived anticancer agent is docetaxel.

Anticancer Platinum Coordination Compound

In one embodiment, the combination of the invention includes at least one anticancer platinum coordination compound as chemotherapeutic agent.

An "anticancer platinum coordination compound" refers to a platinum coordination compound having anticancer activity, and the term "platinum coordination compound" herein refers to a platinum coordination compound which provides platinum in ion form.

Preferred platinum compounds include cisplatin; cis-diamminediaquoplatinum (O)-ion; chloro(diethylenetriamine)-platinum (II) chloride; dichloro(ethylenediamine)-platinum (II); diamine(1, 1-cyclobutanedicarboxylato) platinum (II) (carboplatin); spiroplatin; iproplatin; diamine (2-ethylmalonato)platinum (II); ethylenediaminemalonato-platinum (H); aqua(1,2-diaminodicyclohexane)sulfatoplatinum (II); aqua(1,2-diaminodicyclohexane) malonatoplatinum (II); (1,2-diaminocyclohexane) malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin. Preferably the anticancer platinum coordination compound is selected from carboplatin and oxaliplatin.

Parp Inhibitors

In one embodiment, the combination of the invention includes at least one Parp inhibitor as chemotherapeutic agent.

A "Parp inhibitor" refers to an inhibitor of the enzyme poly ADP ribose polymerase (PARP). This enzyme is important for repairing single-strand breaks in the DNA. If such breaks remain unrepaired until DNA is replicated, then the replication can cause double strand breaks to form. PARP inhibitors thus enable to cause multiple double strand breaks to form in tumors, leading to the death of the tumor cells.

Examples of Parp inhibitors include olaparib, rucaparib, niraparib, veliparib, pamiparib, iniparib, and talazoparib.

Anti-Hormone-Sensitive Cancer Agent

In one embodiment, the combination of the invention includes at least one anti-hormone-sensitive cancer agent as chemotherapeutic agent.

An "anti-hormone-sensitive cancer agent" refers to an anticancer agent having an activity against hormone-sensitive cancers. Examples of anti-hormone-sensitive cancer agents include anti-androgens, GnRH agonists and GnRH antagonists.

"Anti-androgens" refer to a class of drugs that prevent androgens like testosterone and dihydrotestosterone (DHT) from mediating their biological effects in the body. Anti-androgens may be used for example to treat prostate cancer. Examples of anti-androgens include bicalutamide, flutamide, nilutamide, apalutamide, enzalutamide and abiraterone.

"Gonadotropin-releasing hormone agonists" (GnRH agonist) refer to a class of drugs which affects gonadotropins and sex hormones. They may be used to lower sex hormone levels in the treatment of hormone-sensitive cancers such as prostate cancer and breast cancer. Examples of GnRH agonists include goserelin, leuprorelin and triptorelin.

"Gonadotropin-releasing hormone antagonists" (GnRH antagonist) refer to a class of drugs that antagonize the action of gonadotropin-releasing hormone (GnRH). They may be used for example in the treatment of prostate cancer. An example of GnRH antagonist is degarelix.

Combinations of Chemotherapeutic Agents

Combinations of chemotherapeutic agents may be used as the second component of the combination of the invention.

For example, the combination known as folfox may be used. Folfox comprises the combined use of fluorouracil (antimetabolite), oxaliplatin (platinum compound) and folinic acid (chemoprotectant).

A combination consisting of carboplatin (platinum compound) and paclitaxel (plant-derived agent) may alternatively be used. Another example is a combination consisting of gemcitabine (antimetabolite) and nab-paclitaxel (plant-derived agent).

In one embodiment, the combination of chemotherapeutic agents is selected from:
  (i) a combination consisting of folinic acid, fluorouracil and oxaliplatin (folfox);
  (ii) a combination consisting of carboplatin and paclitaxel; and
  (iii) a combination consisting of gemcitabine and nab-paclitaxel.

Antiangiogenic Agent

In one embodiment, the combination of the invention includes at least one antiangiogenic agent as anticancer agent.

Angiogenesis, i.e. growth of new blood vessels, plays an important role in the development of tumors and the progression of malignancies. Inhibiting angiogenesis has been shown to suppress tumor growth and metastasis. The most prominent target of antiangiogenic agents is vascular endothelial growth factor (VEGF) and its receptors. Several other factors are of interest as well, including integrins, matrix metalloproteinases, and endogenous antiangiogenic factors.

Antiangiogenic agents thus include VEGF inhibitors, integrins inhibitors and matrix metalloproteinases inhibitors.

Examples of antiangiogenic agents include Ramucirumab, IMC-18F1, Bevacizumab, Ziv-aflibercept, Sorafenib, Sunitinib, Axitinib, Nintedanib, Regorafenib, Pazobanib, Cabozantinib, Vandetanib and Thalidomide. In a specific embodiment, the antiangiogenic agent is a VEGF inhibitor, for example Ramucirumab.

Multidrug Resistance-Associated Proteins Inhibitors

In one embodiment, the combination of the invention includes at least one multidrug resistance-associated protein inhibitor as anticancer agent.

Multidrug resistance-associated proteins (MRP/ABCC) are a subfamily of ATP-binding cassette transporters, which are capable of actively pumping a wide variety of organic anionic compounds across the plasma membrane against their concentration gradient. These proteins are involved in multi-drug resistance by transporting a wide variety of drugs outside cells, among which anticancer drugs. Inhibiting multidrug resistance-associated proteins can thus improve efficacy of anticancer drugs.

Examples of multidrug resistance-associated protein inhibitor include inhibitors of MRP4/ABCC4, inhibitors of MRP5/ABCC5 and inhibitors of MRP8/ABCC11.

Radiotherapeutic Agents—Radiation Therapy

In one embodiment, the combination of the invention includes at least one radiotherapeutic agent as anticancer agent.

"Radiation therapy" refers to a method of treatment of cancer employing various radiations such as X-ray, γ-ray, neutron ray, electron beam, proton beam and radiation sources. It is used as part of cancer treatment to control or kill malignant cells. Radiation therapy may be curative in a number of types of cancer if they are localized to one area of the body. It may also be used as part of adjuvant therapy, to prevent tumor recurrence after surgery to remove a primary malignant tumor.

The three main divisions of radiation therapy are: external beam radiation therapy (EBRT or XRT); brachytherapy or sealed source radiation therapy; and systemic radioisotope therapy (RIT) or unsealed source radiotherapy. The differences relate to the position of the radiation source; external is outside the body, brachytherapy uses sealed radioactive sources placed precisely in the area under treatment, and systemic radioisotopes are given by infusion or oral ingestion. Particle therapy is a special case of external beam radiation therapy where the particles are protons or heavier ions. Radiations may be delivered by a linear accelerator.

Systemic radioisotope therapy (RIT) is a form of targeted therapy. Targeting can be due to the chemical properties of the isotope such as radioiodine which is specifically absorbed by the thyroid gland a thousand fold better than other bodily organs. Targeting can also be achieved by attaching the radioisotope to another molecule or antibody to guide it to the target tissue, forming a radiopharmaceutical agent.

In order to enhance the radiosensitivity of the cancer, radiosensitizing agents may be administered during a radiation therapy. Examples of radiosensitizing agents include: Cisplatin, Nimorazole, and Cetuximab.

Thus, in one embodiment, radiotherapeutic agent is selected from sealed radiation sources, radioisotopes, radiopharmaceutical agents, radiosensitizing agents and the like useful in the course of radiation therapy.

In another embodiment, the invention also provides the use of the A2AR inhibitor as described above, in combination with radiation therapy, including radiation therapy performed by external beam radiations or X-ray radiations; brachytherapy; and systemic radioisotope therapy.

Combinations

In one embodiment, the combination of the invention comprises at least one A2AR inhibitor as defined above and at least one anticancer agent as defined above.

In a specific embodiment, the combination of the invention comprises at least one A2AR inhibitor as defined above and at least one immunotherapeutic agent as defined above.

In a specific embodiment, the combination of the invention comprises at least one A2AR inhibitor as defined above and at least one checkpoint inhibitor as defined above, preferably an inhibitor of PD-1, PD-L1, CTLA-4 or of TIGIT, or any mixture thereof.

In a specific embodiment, the combination of the invention comprises at least one A2AR inhibitor as defined above and at least one adenosine-producing enzymes inhibitor as defined above, preferably at least one inhibitor of CD39, such as for example ARL67156 and POM-1.

In a specific embodiment, the combination of the invention comprises at least one A2AR inhibitor as defined above and at least one chemotherapeutic agent as defined above.

In a specific embodiment, the combination of the invention comprises at least one A2AR inhibitor as defined above and at least one anticancer antibiotic as defined above, such as for example doxorubicin.

In a specific embodiment, the combination of the invention comprises at least one A2AR inhibitor as defined above and at least one anticancer platinum coordination compound as defined above, such as for example oxaliplatin.

In a specific embodiment, the combination of the invention comprises at least one A2AR inhibitor as defined above, at least one immunotherapeutic agent as defined above and at least one chemotherapeutic agent as defined above.

In a specific embodiment, the combination of the invention comprises at least one A2AR inhibitor as defined above, at least one checkpoint inhibitor as defined above and at least one chemotherapeutic agent as defined above. In a specific embodiment, the combination of the invention comprises at least one A2AR inhibitor as defined above, at least one inhibitor of PD-L1, CTLA-4 or TIGIT and at least one chemotherapeutic agent as defined above. In a specific embodiment, the combination of the invention comprises at least one A2AR inhibitor as defined above, at least one checkpoint inhibitor as defined above and at least one. In a specific embodiment, the combination of the invention comprises at least one A2AR inhibitor as defined above, at least one inhibitor of PD-L1, CTLA-4 or TIGIT as defined above and at least one anticancer antibiotic as defined above, such as for example doxorubicin.

In a specific embodiment, the combination of the invention comprises at least one A2AR inhibitor as defined above and at least two checkpoint inhibitor as defined above. In a specific embodiment, the combination of the invention comprises at least one A2AR inhibitor as defined above, at least one inhibitor of PD-L1 as defined above and at least one inhibitor of TIGIT as defined above.

Pharmaceutical Composition

The invention further relates to a pharmaceutical composition comprising the combination of the invention.

In one embodiment, the pharmaceutical composition comprises:
(a) at least one A2AR inhibitor,
(b) at least one anticancer agent, and
(c) at least one pharmaceutically acceptable carrier, diluent, excipient and/or adjuvant.

In a preferred embodiment, the invention provides a pharmaceutical composition comprising:
(a) at least one A2AR inhibitor being a thiocarbamate derivative, more preferably a thiocarbamate derivative of Formula (I) or a pharmaceutically acceptable salt or solvate thereof, as defined above;
(b) at least one anticancer agent as defined above, such as for example immunotherapeutic agents, chemotherapeutic agents, antiangiogenic agents, multidrug resistance-associated proteins inhibitors, radiotherapeutic agents, or any combination thereof, and
(c) at least one pharmaceutically acceptable carrier, diluent, excipient and/or adjuvant.

The at least one pharmaceutically acceptable carrier, diluent, excipient and/or adjuvant for use in the preparation of the administration forms will be clear to the skilled person; reference is made to the latest edition of Remington's Pharmaceutical Sciences.

Especially, the pharmaceutical composition comprising the combination of the invention can optionally contain such inactive substances that are commonly used in pharmaceutical formulations, such as for example cosolvents, lipid carrier, antioxidants, surfactants, wetting agents, emulsifying agents, buffering agents, pH modifying agents, preserving agents (or preservating agents), isotonifiers, stabilizing agents, granulating agents or binders, precipitation inhibitors, lubricants, disintegrants, glidants, diluents or fillers, adsorbents, dispersing agents, suspending agents, bulking agents, release agents, sweetening agents, flavoring agents, and the like.

In a preferred embodiment, the pharmaceutical composition comprising the combination of the invention comprises one or more pharmaceutically acceptable cosolvent. Preferably cosolvents are selected from caprylic acid, polyethylene glycol (PEG), propylene glycol, ethanol, dimethylsulfoxide, dimethylacetamide, dimethylisosorbide and mixtures thereof. In a specific embodiment, the pharmaceutical composition of the invention comprises caprylic acid and/or PEG. Advantageously, when the composition comprises PEG as cosolvent, PEG is of low molecular weight, preferably PEG is PEG 400. In an alternative embodiment, when the composition comprises PEG, it is of a moderate molecular weight, preferably PEG 3350.

In a specific embodiment, the pharmaceutical composition comprising the combination of the invention comprises one or more pharmaceutically acceptable lipid carrier. In a preferred embodiment, the lipid carrier is lauroyl polyoxyl-32 glycerides. This excipient corresponds to Gelucire® 44/14 manufactured by Gattefossé (Saint-Priest—France). This excipient is also known under the following references: lauroyl polyoxyl-32 glycerides NF/USP (NF: National Formulary; USP: US Pharmacopeia); lauroyl macrogol-32 glycerides EP (European Pharmacopeia); hydrogenated coconut PEG-32 esters (INCI); CAS number 57107-95-6. Gelucire® 44/14 corresponds to a well-defined multi-constituent substance constituted of mono-, di- and triglycerides and PEG-32 mono- and diesters of lauric acid ($C_1$). Gelucire® 44/14 has a melting point ranging from 42.5° C. to 47.5° C. (with a mean at 44° C.) and an hydrophilic/lipophilic balance (HLB) value of 14.

In another embodiment, the lipid carrier is Vitamin E TPGS. This excipient is also known under the following references: D-α-Tocopherol polyethylene glycol-1000 succinae: Tocophersolan; Tocofersolan; VEGS; α-[4-[[(2R)-3,4-dihydro-2,5,7,8-tetramethyl-2-[(4R,8R)-4,8,12-trimethyl-tridecyl]-2H-1-benzopran-6-yl]oxy]-1,4ioxobutyl]-ω-hydroxy-poly(oxy-1,2-ethanediyl); Vitamin E PEG succinate and is formed from Vitamin E which is conjugated to polyethylene glycol 1000 via a succinic acid linker. Vitamin F TPGS has melting point in the range 37-41° C. and an hydrophilic/lipophilic balance (HLB) value of 13.

In one embodiment, the pharmaceutical composition comprising the combination of the invention further comprises one or more antioxidant; preferably the antioxidant is selected from butylated hydroxytoluene (BHT), butylated hydroxyanisole (BHA), citric acid, sodium metabisulfite, ascorbic acid, methionine and vitamin E; more preferably the antioxidant is BHT.

In some embodiments, surfactants are added, such as for example polyethylene glycols, polyoxyethylene sorbitan fatty acid esters, sorbitan esters, sodium docusate, sodium lauryl sulfate, polysorbates (20, 80, etc.), poloxamers (188, 407 etc.), pluronic polyols, polyoxyethylene sorbitan monoethers (TWEEN©-20, TWEEN®-80, etc.), vitamin E TPGS (Vitamin E polyethylene glycol succinate), cremophor RH40 (polyoxyl 40 hydrogenated castor oil), cremophor EL (polyoxyl 35 hydrogenated castor oil), polyethylene glycol 660 12-monostearate, solutol HS15 (Polyoxyethylated 12-hydroxystearic acid), labrasol (caprylocaproyl polyoxyl-8 glycerides), labrafil M1944 (Oleoyl polyoxyl-6 glycerides), polylactide polyethylene glycol copolymer, polyvinyl caprolactam-polyvinyl acetate-polyethylene glycol graft copolyner (Soluplus®).

In some embodiments, wetting agents are added, such as for example sodium lauryl sulphate, vitamin E TPGS, sodium docusate, polysorbate 80, poloxamer 407. A preferred wetting agent is poloxamer 407.

In some embodiments, emulsifying agents are added, such as for example carbomer, carrageenan, lanolin, lecithin, mineral oil, oleic acid, oleyl alcohol, pectin, poloxamer, polyoxyethylene sorbitan fatty acid esters, sorbitan esters, triethanolamine, propylene glycol monolaurate, propylene glycol dilaurate, propylene glycol monocaprylate. Preferred emulsifying agents are for example poloxamer, propylene glycol monolaurate, propylene glycol dilaurate, and propylene glycol monocaprylate.

In some embodiments, buffering agents are used to help to maintain the pH in the range that approximates physiological conditions Suitable buffering agents include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments, pH modifiers are added, such as for example sodium hydroxide, sodium bicarbonate, magnesium oxide, potassium hydroxide, meglumine, sodium carbonate, citric acid, tartaric acid, ascorbic acid, fumaric acid, succinic acid and malic acid;

In some embodiments, preservatives agents are added to retard microbial growth. Suitable preservatives for use with the present disclosure include phenol, benzyl alcohol, metacresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" are added and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall or helps to inhibit the precipitation, particle growth or agglomeration of the active ingredient. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone; poloxamer 407; cellulose derivatives such as hydroxypropylmethylcellulose, hydroxypropylmethylcellulose phthalate or hydroxypropylmethylcellulose acetate succinate; carboxymethylcellulose (Na/Ca); monosaccharides, such as xylose, mannose, fructose, glucose; disaccharides such as lactose, maltose, sucrose and trisaccacharides such as raffinose; polysaccharides such as dextran; polyethylene glycol methyl ether-block-poly(D-L-lactide) copolymer; poly(butyl methacrylate-co-(2-dimethylaminoethyl) methacrylate-co-methyl methacrylate) 1:2:1. Preferred stabilizers are for example glycerol; polyethylene glycol; polyvinylpyrrolidone; cellulose derivatives such as hydroxypropylmethylcellulose, hydroxypropylmethylcellulose phthalate or hydroxypropylmethylcellulose acetate succinate; carboxymethylcellulose (Na/Ca); polyethylene glycol methyl ether-block-poly(D-L-lactide) copolymer; and poly(butyl methacrylate-co-(2-dimethylaminoethyl) methacrylate-co-methyl methacrylate) 1:2:1, polyvinyl caprolactam-polyvinyl acetate-polyethylene glycol graft copolymer, polyvinylpyrrolidone polyvinylacetate copolymer.

In some embodiments granulating agent/binder(s) are added, such as for example starch, gums (inclusive of natural, semisynthetic and synthetic), microcrystalline cellulose, ethyl cellulose, methylcellulose, hydroxypropylcellulose, polymers such as povidone, polyvinylpyrrolidone polyvinylacetate copolymer and the like. Preferred granulating agents are for example methylcellulose, hydroxypropylcellulose, povidone and polyvinylpyrrolidone polyvinylacetate copolymer.

In some embodiments precipitation inhibitors are added, such as for example water soluble derivatives of cellulose including hydroxypropylmethylcellulose and methylcellulose, and water soluble polymers such as polyvinylpyrrolidone, polyvinylpyrrolidone polyvinylacetate copolymer, polyvinyl caprolactam-polyvinyl acetate-polyethylene glycol graft copolymer or poloxamer 407. A preferred precipitation inhibitor is hydroxypropylmethylcellulose.

In some embodiments lubricants are added, such as for example magnesium stearate, glyceryl esters, behenoyl polyoxyl-8 glycerides Nf (Compritol HD5 ATO), sodium stearyl fumarate and the like.

In some embodiments disintegrants are added, such as for example synthetics like sodium starch glycolate, cross povidone, cross carmellose sodium, kollidon CL, and natural origin such as locust bean gum and the like.

In some embodiments glidants are added, such as for example talc, magnesium stearate, colloidal silicon dioxide, starch and the like.

In some embodiments diluents (or fillers) are added, such as for example dextrose, lactose, mannitol, microcrystalline cellulose, sorbitol, sucrose, dibasic calcium phosphate, calcium sulphate dehydrate, starch and the like.

In some embodiments adsorbents are added, such as for example silicon dioxide, purified aluminium silicate and the like.

In some embodiments, the pharmaceutical composition comprising the combination of the invention is in the form of tablets and tableting excipients are added, such as for example granulating agents, binders, lubricants, disintegrants, glidants, diluents, adsorbents and the like.

In some embodiments the pharmaceutical composition comprising the combination of the invention is in the form of capsules, in which the capsule shells are constructed from gelatin or from non-animal derived products such as cellulose and its derivatives such as hydroxypropylmethylcellulose. Other ingredients may be included in the capsule shells such as polyethyleneglycol to act as plasticizer; pigments such as titanium dioxide or iron oxide to provide opacity and colour differentiation; lubricants such as carnauba wax; gelling agents such as carrageenan and wetting agents such as sodium lauryl sulphate. In one embodiment, the pharmaceutical composition comprising the combination of the invention is formulated as capsules, wherein the capsule shells are constructed from gelatin and wherein additional components are optionally included in the capsule shells, such as for example polyethylene glycol and sodium lauryl sulphate.

By means of non-limiting examples, the pharmaceutical composition comprising the combination may be in a form suitable for oral administration, for parenteral administration (such as by intravenous, intramuscular or subcutaneous injection or intravenous infusion), for topical administration (including ocular), for rectal administration, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

The compositions may be formulated so as to provide rapid, sustained or delayed release of the active compound(s) contained therein.

According to one embodiment, the pharmaceutical composition comprising the combination is in an adapted form for an oral administration. Forms adapted to oral administration may be solid, semi-solid or liquid. Some preferred, but non-limiting examples of such forms include liquid, paste or solid compositions, and more particularly tablets, tablets formulated for extended or sustained release, capsules (including soft and hard gelatin capsules), pills, dragees, lozenges, sachets, cachets, powder, liquids, gels, syrups, slurries, elixirs, emulsions, solutions, and suspensions.

According to another embodiment, the pharmaceutical composition comprising the combination is in an adapted form for an injection, especially to be injected to the subject by intravenous, intramuscular, intraperitoneal, intrapleural, subcutaneous, transdermal injection or infusion.

Sterile injectable forms of the pharmaceutical composition of the invention include sterile injectable solutions and sterile packaged powders (which are usually reconstituted prior to use) for administration as a bolus and/or for continuous administration.

Sterile injectable forms of the pharmaceutical composition of the invention may be a solution or an aqueous or oleaginous suspension. These suspensions may be formulated according to techniques known in the art using suitable dispersing or wetting agents and suspending agents. The sterile injectable preparation may also be a sterile injectable solution or suspension in a non-toxic pharmaceutically acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions.

Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

According to another embodiment, the pharmaceutical composition comprising the combination of the invention is in an adapted form for a topical administration. Examples of forms adapted for topical administration include, without being limited to, liquid, paste or solid compositions, and more particularly aqueous solutions, drops, dispersions, sprays, ointments, cremes, lotions, microcapsules, micro- or nanoparticles, polymeric patch, or controlled-release patch, and the like.

According to another embodiment, the pharmaceutical composition comprising the combination of the invention is in an adapted form for a rectal administration. Examples of forms adapted for rectal administration include, without being limited to, suppository, micro enemas, enemas, gel, rectal foam, cream, ointment, and the like.

According to another embodiment, the pharmaceutical composition comprising the combination of the invention is in an adapted form for an administration by inhalation. Examples of forms adapted for administration by inhalation include, without being limited to aerosols.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Kit of Parts

The invention further relates to a kit of parts comprising the combination of the invention.

In one embodiment, the kit of parts of the invention comprises:
(a) a first part comprising at least one A2AR inhibitor, and
(b) a second part comprising at least one anticancer agent.

In a preferred embodiment, the invention provides a kit of parts comprising:
(a) a first part comprising at least one A2AR inhibitor being a thiocarbamate derivative, more preferably a thiocarbamate derivative of Formula (I)

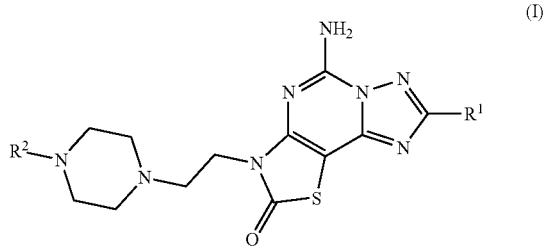

or a pharmaceutically acceptable salt or solvate thereof, as defined above; and
(b) a second part comprising at least one anticancer agent as defined above, such as for example immunotherapeutic agents, chemotherapeutic agents, antiangiogenic agents, multidrug resistance-associated proteins inhibitors, radiotherapeutic agents, or any combination thereof.

In one embodiment, the first part comprises a pharmaceutical composition comprising an A2AR inhibitor, preferably a thiocarbamate derivative of Formula (I) as defined above, and at least one pharmaceutically acceptable carrier, diluent, excipient and/or adjuvant.

Pharmaceutically acceptable carrier, diluent, excipient and/or adjuvant of the pharmaceutical composition of the first part of the kit of part may be those listed above with regards to the pharmaceutical composition of the invention.

Similarly, the dosage form and the administration route of the pharmaceutical composition of the first part of the kit of part may be those listed above with regards to the pharmaceutical composition of the invention.

In one embodiment, the second part comprises at least one anticancer agent as defined above. Depending on the type of anticancer agent, the second part of the kit may be under the form of a pharmaceutical composition. Excipients, dosage form and administration route of such a pharmaceutical composition will be clear to the skilled person (reference is made to the latest edition of Remington's Pharmaceutical Sciences), and especially may be those listed above with regards to the pharmaceutical composition of the invention.

According to one embodiment, the kit of the invention may comprise one or more further parts comprising one or more further anticancer agents. For example, the kit may comprise (a) a first part comprising an A2AR inhibitor of Formula (I); (b) a second part comprising an immunotherapeutic agent; and (c) a third part comprising a chemotherapeutic agent. In another embodiment, the kit may comprise (a) a first part comprising an A2AR inhibitor of Formula (I); (b) a second part comprising a checkpoint inhibitor; and (c) a third part comprising a chemotherapeutic agent. In another embodiment, the kit may comprise (a) a first part comprising an A2AR inhibitor of Formula (I); (b) a second part comprising a checkpoint inhibitor; and (c) a third part comprising a different checkpoint inhibitor.

As developed below, the administration of the different parts of the kit may be made simultaneously or timely staggered, with similar or different timing of administration (i.e. similar or different numbers of administration of each component), either at the same site of administration or at different sites of administration, under similar of different dosage forms.

Regimen and Doses

In the context of the present invention, the administration of the A2AR inhibitor and the anticancer agent may occur either simultaneously or timely staggered, with similar or different timing of administration (i.e. similar or different numbers of administration of each component), either at the same site of administration or at different sites of administration, under similar of different dosage forms, as further outlined below.

To ensure that the separate mechanisms elicited by the A2AR inhibitor and the anticancer agent are not negatively influenced by each other, the anticancer agent and the A2AR inhibitor are preferably administered separated in time (in a time-staggered manner), i.e. sequentially, and/or are administered at different administration sites. This means that the A2AR inhibitor may be administered e.g. prior, concurrent or subsequent to the anticancer agent, or vice versa. Alternatively or additionally, the A2AR inhibitor and the anticancer agent may be administered at different administration sites, or at the same administration site, preferably, when administered in a time staggered manner.

In one embodiment, the A2AR inhibitor is to be administered prior to and/or concomitantly with an immunotherapeutic agent as described hereinabove. In one embodiment, the immunotherapeutic agent is a checkpoint inhibitor and the A2AR inhibitor is to be administered prior to the day or on the same day that the checkpoint inhibitor as described hereinabove is administered.

In one embodiment, the A2AR inhibitor is to be administered prior to and/or concomitantly with an immunotherapeutic agent as described hereinabove and continuously thereafter.

In one embodiment, the A2AR inhibitor is to be administered prior to or concomitantly with an immunotherapeutic agent as described hereinabove and subsequently for at least 1, 2, 3, 4, 5, 6, 7, 8, 9, or 10 days thereafter. In another embodiment, the A2AR inhibitor is to be administered prior to or concomitantly with an immunotherapeutic agent as described hereinabove and subsequently for at least 1, 2, 3, 4, 5, 6, 7, 8, 9, or 10 weeks thereafter. In another embodiment, the A2AR inhibitor is to be administered prior to or concomitantly with an immunotherapeutic agent as described hereinabove and subsequently for at least 1, 2, 3, 4, 5, 6, 7, 8, 9, or 10 months thereafter.

In one embodiment, the immunotherapeutic agent is a checkpoint inhibitor and the A2AR inhibitor is to be administered prior to or concomitantly with said checkpoint inhibitor. In one embodiment, the immunotherapeutic agent is a checkpoint inhibitor and the A2AR inhibitor is to be administered prior to or concomitantly with said checkpoint inhibitor and continuously thereafter. In one embodiment, the immunotherapeutic agent is a checkpoint inhibitor and the A2AR inhibitor is to be administered prior to or concomitantly with said checkpoint inhibitor and subsequently for at least 1, 2, 3, 4, 5, 6, 7, 8, 9, or 10 weeks thereafter.

Depending on the condition to be prevented or treated and the form of administration, the combination of the invention may be administered as a single daily dose, divided over one or more daily doses.

According to one embodiment, a therapeutically effective dose of A2AR inhibitor as described hereinabove is to be administered for use in the treatment of a cancer in a subject in need thereof, wherein said A2AR inhibitor is used in combination with an anticancer agent, such as for example an immunotherapeutic agent. Thus, in one embodiment, the pharmaceutical combination or kit of parts of the invention comprises a therapeutically effective dose of A2AR inhibitor as described hereinabove and a therapeutically effective dose of anticancer agent as described hereinabove.

It will be understood that the total daily usage of A2AR inhibitor and anticancer agent will be decided by the attending physician within the scope of sound medical judgment. The specific dose for any particular subject will depend upon a variety of factors such as the cancer to be treated; the age, body weight, general health, sex and diet of the patient; and like factors well-known in the medical arts.

In one embodiment, the subject is a mammal, preferably a human, and the dose of A2AR inhibitor, preferably a therapeutically effective dose, is a dose ranging from about 0.01 mg per kilo body weight (mg/kg) to about 5 mg/kg, preferably about 0.08 mg/kg to about 3.3 mg/kg, more preferably about 0.15 mg/kg to about 1.7 mg/kg.

In one embodiment, the subject is a mammal, preferably a human, and the dose of A2AR inhibitor, preferably a therapeutically effective dose, is a dose ranging from about 0.01 mg per kilo body weight per day (mg/kg/day) to about 5 mg/kg/day, preferably about 0.08 mg/kg/day to about 3.3 mg/kg/day, more preferably about 0.15 mg/kg/day to about 1.7 mg/kg/day.

In one embodiment, the subject is a mammal, preferably a human, and the dose of A2AR inhibitor, preferably a therapeutically effective dose, is a dose ranging from about 1 mg to about 500 mg, preferably about 5 mg to about 200 mg, more preferably from about 10 mg to about 100 mg.

In one embodiment, the subject is a mammal, preferably a human, and the dose of A2AR inhibitor, preferably a therapeutically effective dose, is a dose ranging from about 1 mg to about 500 mg per administration, preferably about 5 mg to about 200 mg per administration, more preferably from about 10 mg to about 100 mg per administration.

In one embodiment, the subject is a mammal, preferably a human, and the dose of A2AR inhibitor, preferably a therapeutically effective dose, is a daily dose ranging from about 1 mg to about 500 mg, preferably about 5 mg to about 200 mg, more preferably from about 10 mg to about 100 mg.

In one embodiment, the subject is a mammal, preferably a human, and the dose of A2AR inhibitor, preferably a therapeutically effective dose, is a daily dose to be administered in one, two, three or more takes. In one embodiment, the subject is a mammal, preferably a human, and the dose of A2AR inhibitor, preferably a therapeutically effective dose, is a daily dose to be administered in one or two takes.

Uses

Another object of this invention is the use of the combination of the invention as a medicament. Thus, in one embodiment, the invention provides the use of the combination of the invention for the manufacturing of a medicament. Especially, the invention provides the use of the pharmaceutical composition of the invention or the kit of the invention for the manufacturing of a medicament.

Especially, the invention provides the combination, the pharmaceutical composition or the kit of parts of the invention, for use in the treatment and/or prevention of cancer.

In one embodiment, the invention relates to a treatment and/or prevention of cancer, which comprises administering to a mammal species in need thereof a therapeutically effective amount of the combination, pharmaceutical composition or kit of parts of the invention.

The invention further provides the use of the combination, pharmaceutical composition or kit of parts of the invention for the manufacture of a medicament for treating and/or preventing cancer.

The invention also provides for a method for delaying in patient the onset of cancer comprising the administration of a pharmaceutically effective amount of the combination, pharmaceutical composition or kit of parts of the invention to a patient in need thereof.

Various cancers are known in the art. Cancers that can be treated using the methods of the invention include solid cancers and non-solid cancers, especially benign and malignant solid tumors and benign and malignant non-solid tumors. The cancer may be metastatic or non-metastatic. The cancer may be may be familial or sporadic.

In one embodiment, the cancer to be treated according to the present invention is a solid cancer. As used herein, the term "solid cancer" encompasses any cancer (also referred to as malignancy) that forms a discrete tumor mass, as opposed to cancers (or malignancies) that diffusely infiltrate a tissue without forming a mass.

Examples of solid tumors include, but are not limited to: biliary tract cancer, brain cancer (including glioblastomas and medulloblastomas), breast cancer, carcinoid, cervical cancer, choriocarcinoma, colon cancer, colorectal cancer, endometrial cancer, esophageal cancer, gastric cancer, glioma, head and neck cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, thyroid cancer (including thyroid adenocarcinoma and medullary carcinoma) and urothelial cancer.

In another embodiment, the cancer to be treated according to the present invention is a non-solid cancer. Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In a specific embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers.

In a specific embodiment, the cancer is breast cancer. In a specific embodiment, the cancer is carcinoid cancer. In a specific embodiment, the cancer is cervical cancer. In a specific embodiment, the cancer is colorectal cancer. In a specific embodiment, the cancer is endometrial cancer. In a specific embodiment, the cancer is glioma. In a specific embodiment, the cancer is head and neck cancer. In a specific embodiment, the cancer is liver cancer. In a specific embodiment, the cancer is lung cancer. In a specific embodiment, the cancer is melanoma. In a specific embodiment, the cancer is ovarian cancer. In a specific embodiment, the cancer is pancreatic cancer. In a specific embodiment, the cancer is prostate cancer. In a specific embodiment, the cancer is renal cancer. In a specific embodiment, the cancer is gastric cancer. In a specific embodiment, the cancer is thyroid cancer. In a specific embodiment, the cancer is urothelial cancer.

In another specific embodiment, the cancer is selected from the group consisting of: leukemia and multiple myeloma.

In one embodiment, the invention relates to the combination, pharmaceutical composition or kit of parts as herein above defined for use in immunotherapy, preferable as cancer immunotherapy.

In one embodiment, the invention relates to a method of immunotherapy, preferably of cancer immunotherapy, which comprises administering to a mammal species in need thereof a therapeutically effective amount of the combination, pharmaceutical composition or kit of parts of the invention.

The invention further provides the use of the combination, pharmaceutical composition or kit of parts of the invention for the manufacture of a medicament for conducting immunotherapy, preferably of cancer immunotherapy.

In one embodiment, the invention relates to the use of the combination, pharmaceutical composition or kit of parts of the invention, for increasing immune recognition and destruction of the cancer cells.

In one embodiment, the invention relates to a method for increasing immune recognition and destruction of the cancer cells, which comprises administering to a mammal species in need thereof a therapeutically effective amount of the combination, pharmaceutical composition or kit of parts of the invention.

The invention further provides the use of the combination, pharmaceutical composition or kit of parts of the invention for the manufacture of a medicament for increasing immune recognition and destruction of the cancer cells.

Preferably, the patient is a warm-blooded animal, more preferably a human.

In one embodiment, the patient receiving the A2AR inhibitor as herein described is also receiving an immunotherapy, a chemotherapy, radiotherapy or a combination thereof.

In one embodiment, the subject is resistant to an immunotherapy. In one embodiment, the subject is resistant to a cancer immunotherapy.

In one embodiment, the subject is resistant to a chemotherapy. In one embodiment, the subject is resistant to a cancer chemotherapy.

In one embodiment, the subject is resistant to a radiotherapy. In one embodiment, the subject is resistant to a cancer radiotherapy.

The invention also relates to a compound of Formula (I) as defined above for use in therapy in combination with an anticancer agent as defined above, especially immunotherapeutic agents, chemotherapeutic agents, antiangiogenic agents, multidrug resistance-associated proteins inhibitors, radiotherapeutic agents, or any combination thereof.

The invention also relates to a compound of Formula (I) as defined above for use in a patient treated by immunotherapy, a chemotherapy, radiotherapy or a combination thereof.

The invention thus also relates to a method for treating cancer in a subject resistant to an anticancer agent, comprising administering to the patient a compound of Formula (I) as defined above and said anticancer agent. In one embodiment, said anticancer agent is an immunotherapy, a chemotherapy, radiotherapy or a combination thereof.

The invention further relates to a method for increasing the therapeutic response of a subject to an anticancer agent, comprising further administering to the patient a compound of Formula (I) as defined above. In one embodiment, said anticancer agent is an immunotherapy, a chemotherapy, radiotherapy or a combination thereof.

The invention also relates to an anticancer agent as defined above for use in therapy in combination with a compound of Formula (I) as defined above.

BRIEF DESCRIPTION OF THE DRAWINGS

FIG. 1A is a graph representing the tumor volume over time after inoculation. FIG. 1B shows the distribution of tumors volume at day 22.

FIG. 2A is a graph representing the tumor volume over time after inoculation. FIG. 2B shows the distribution of tumors volume at day 23.

Figure 3A:
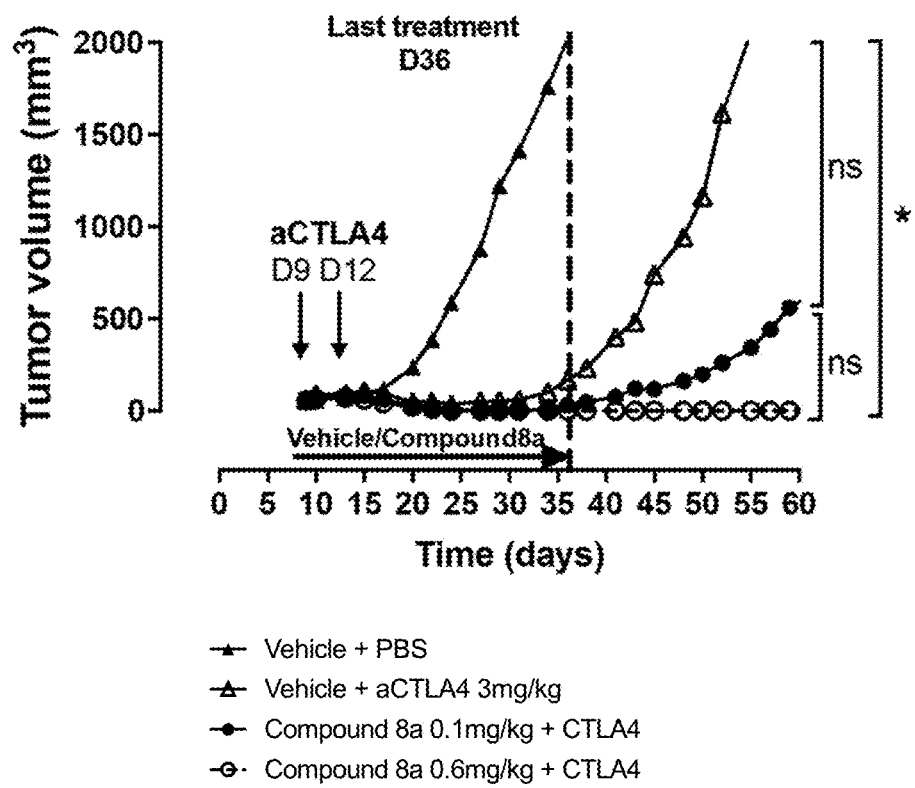
FIGS. 3A-E show EMT6 tumor growth upon treatment with Compound 8a in combination with antagonist anti-CTLA4 mAb. The number of complete responders (CR) out of 10 mice per group is indicated. Tumor growth over time.
Figure 3B:
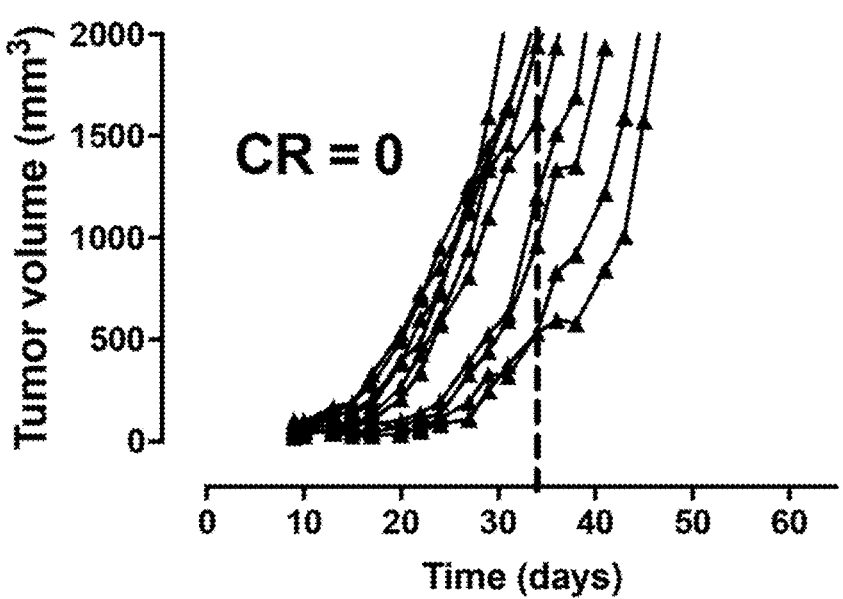
Figure 3C:
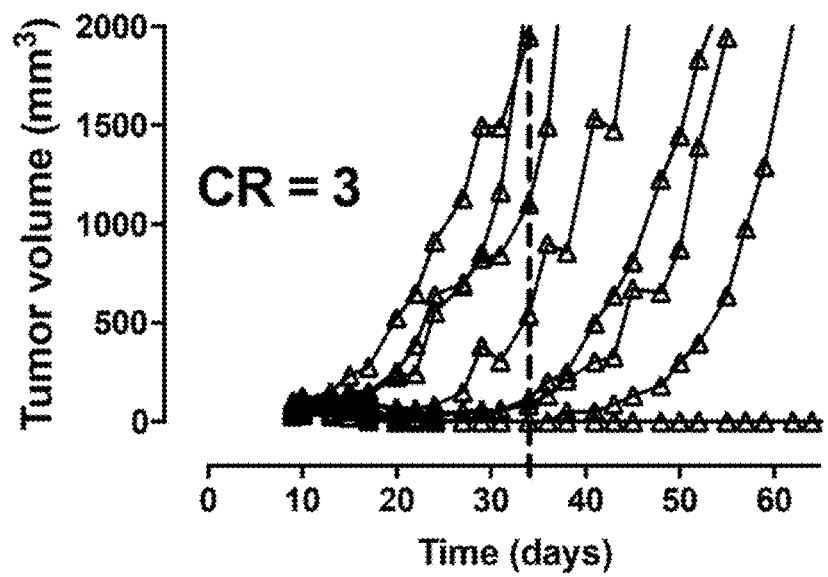
Figure 3D:
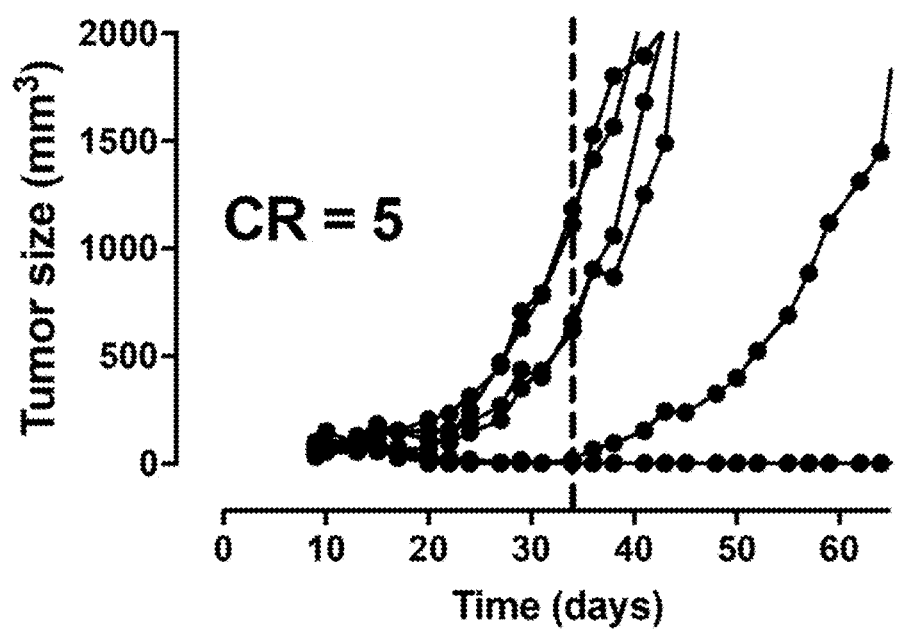
Figure 3E:
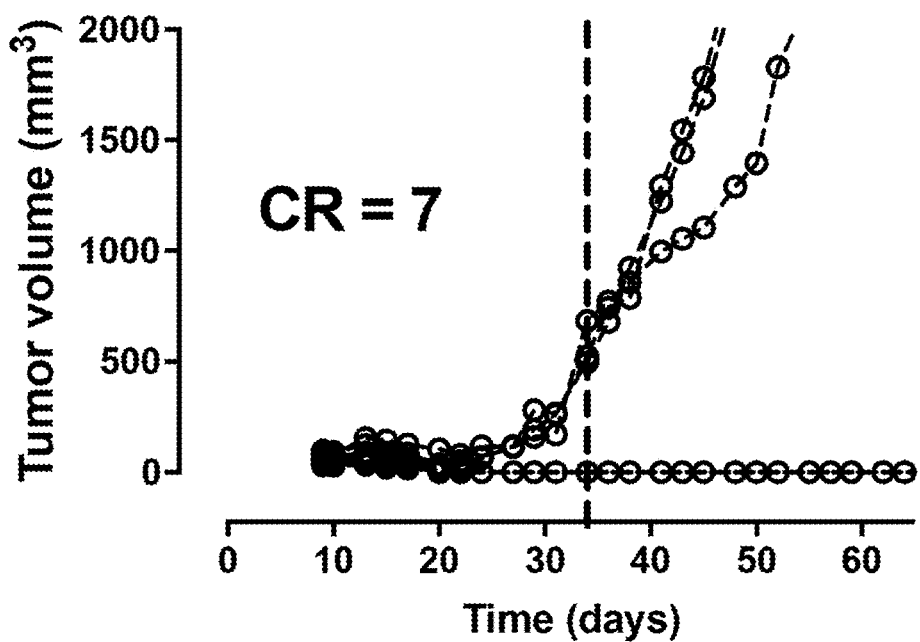

Median (FIG. 3A), Vehicle (FIG. 3B) and aCTLA-4, 3 mg/kg Q3D×2 (day 9, 12) standalone (FIG. 3C) or in combination with D) Compound 8, 0.1 mg/kg QD×25 (FIG. 3D) or Compound 8, 0.6 mg/kg QD×25 (FIG. 3E).

Figure 4A:
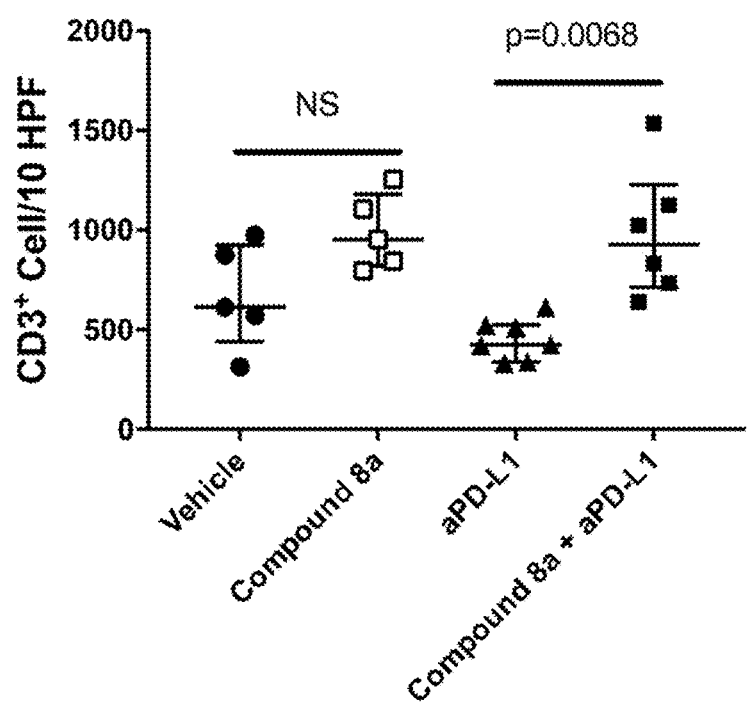
Figure 4B:
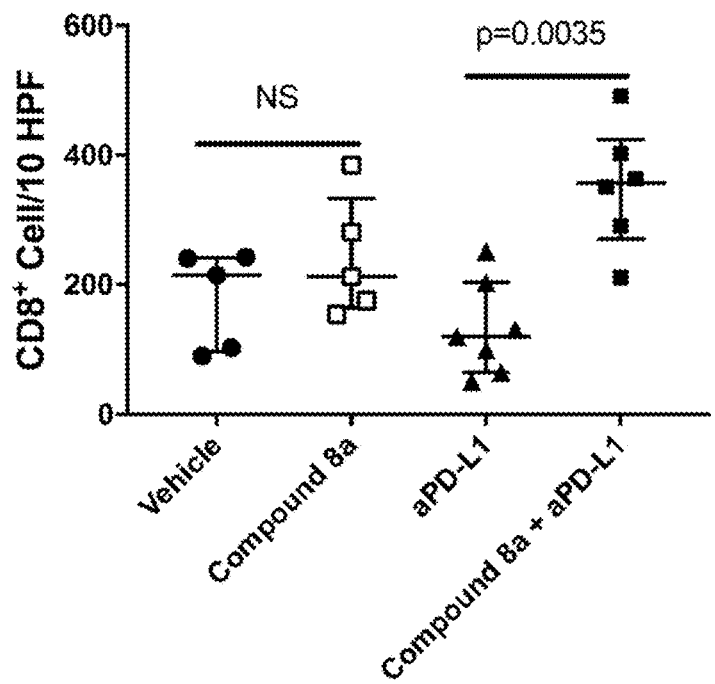

FIGS. 4A and 4B show that A2AR inhibitor Compound 8a in combination with anti-PD-L1 mAb modulates T cell infiltrate in the A20 tumor microenvironment. The absolute quantification of the number of $CD3^+$ T cells (FIG. 4A) and $CD8^+$ T cells (FIG. 4B) was measured by calculation from the average of 10 high powered fields/sections (10 HPF) from independent tumors (symbols represent individual mice; n=5 to 7 mice per/group). The median and interquartile range are shown, p values where calculated using Mann Whitney non-parametric t test.

Figure 5A:
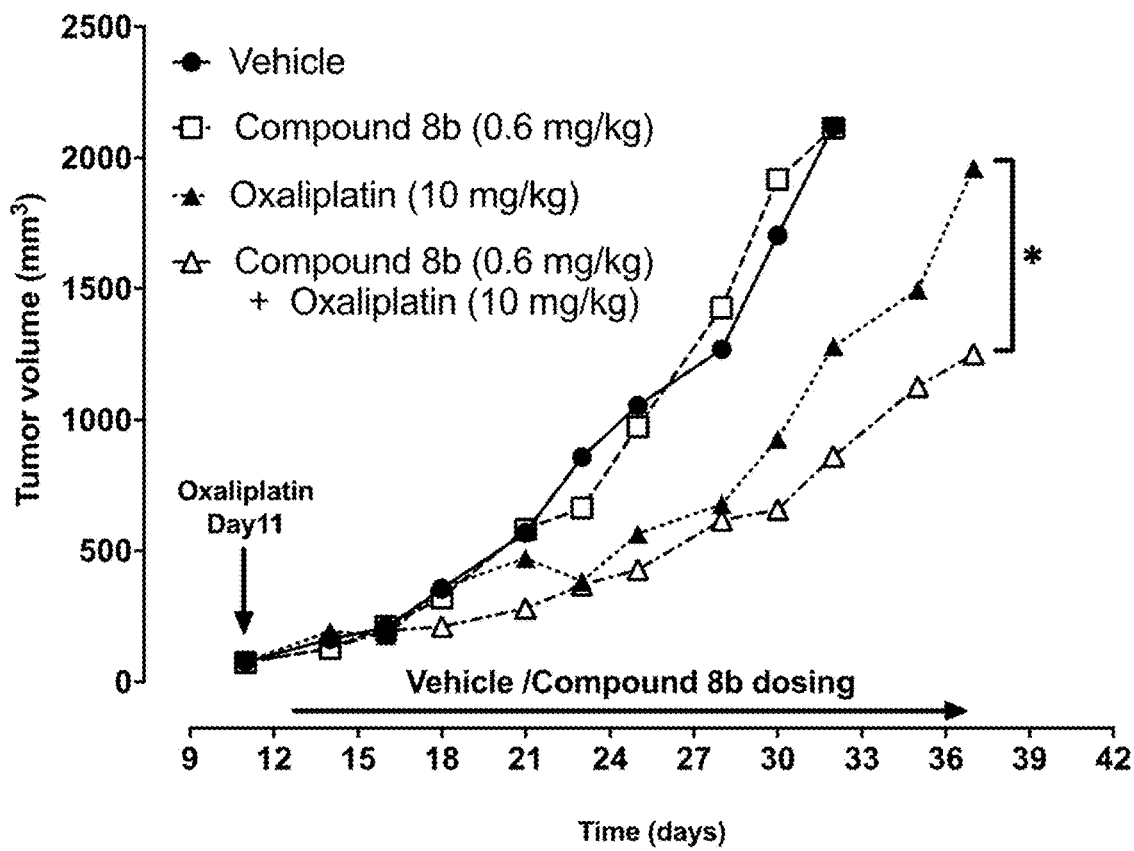
Figure 5B:
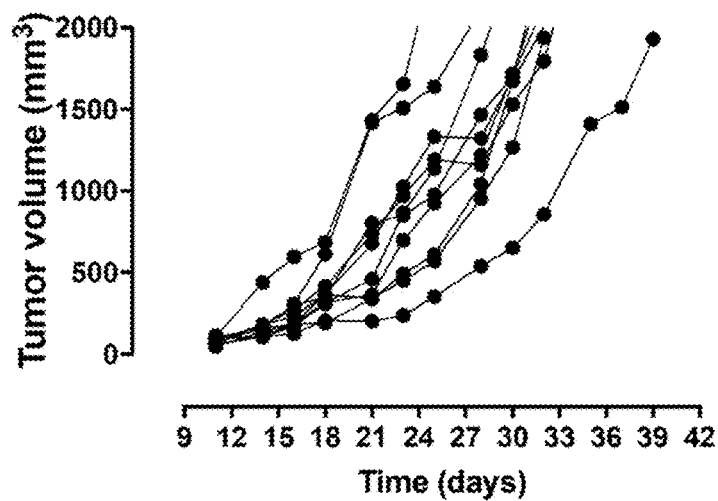
Figure 5C:
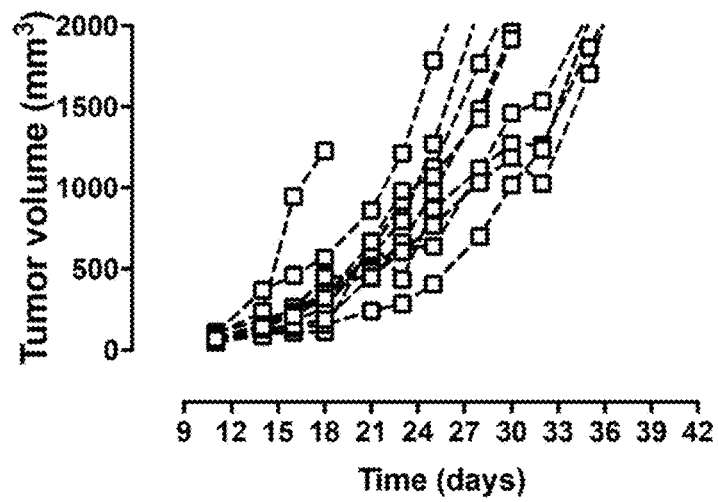
Figure 5D:
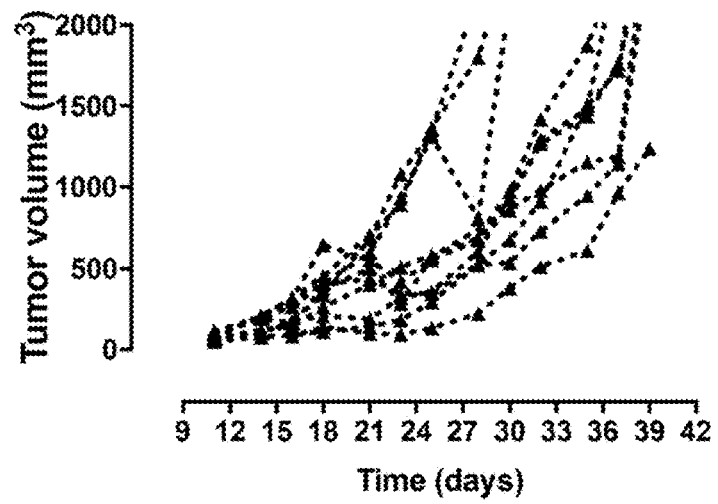
Figure 5E:
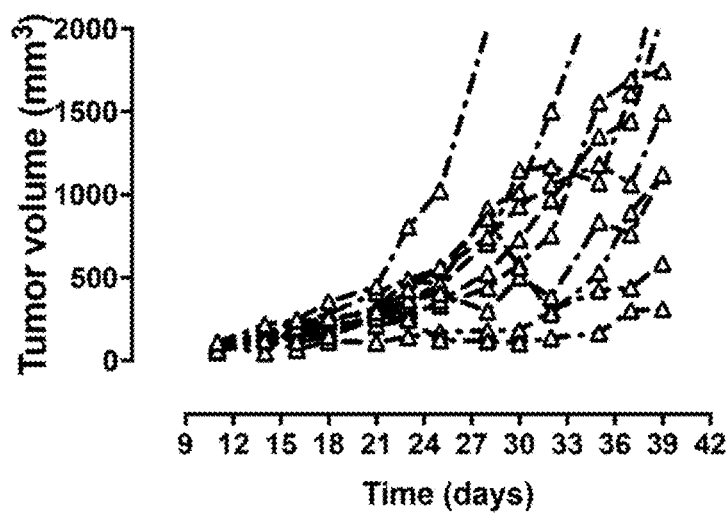

FIGS. 5A-E show the MCA205 tumor growth upon treatment with Compound 8b used as single agent or in combination with Oxaliplatin. FIG. 5A is a graph representing the median tumor volume over time after subcutaneous inoculation of tumor cells. FIGS. 5B-E are the individual tumor growth volumes of mice treated with Vehicle (FIG. 5B), Compound 8b at 0.6 mg/kg QD×25 (FIG. 5C), and Oxaliplatin at 10 mg/kg QD×1 (day 11) in standalone (FIG. 5D) or in combination with Compound 8b at 0.6 mg/kg QD×25 (FIG. 5E).

Figure 6A:
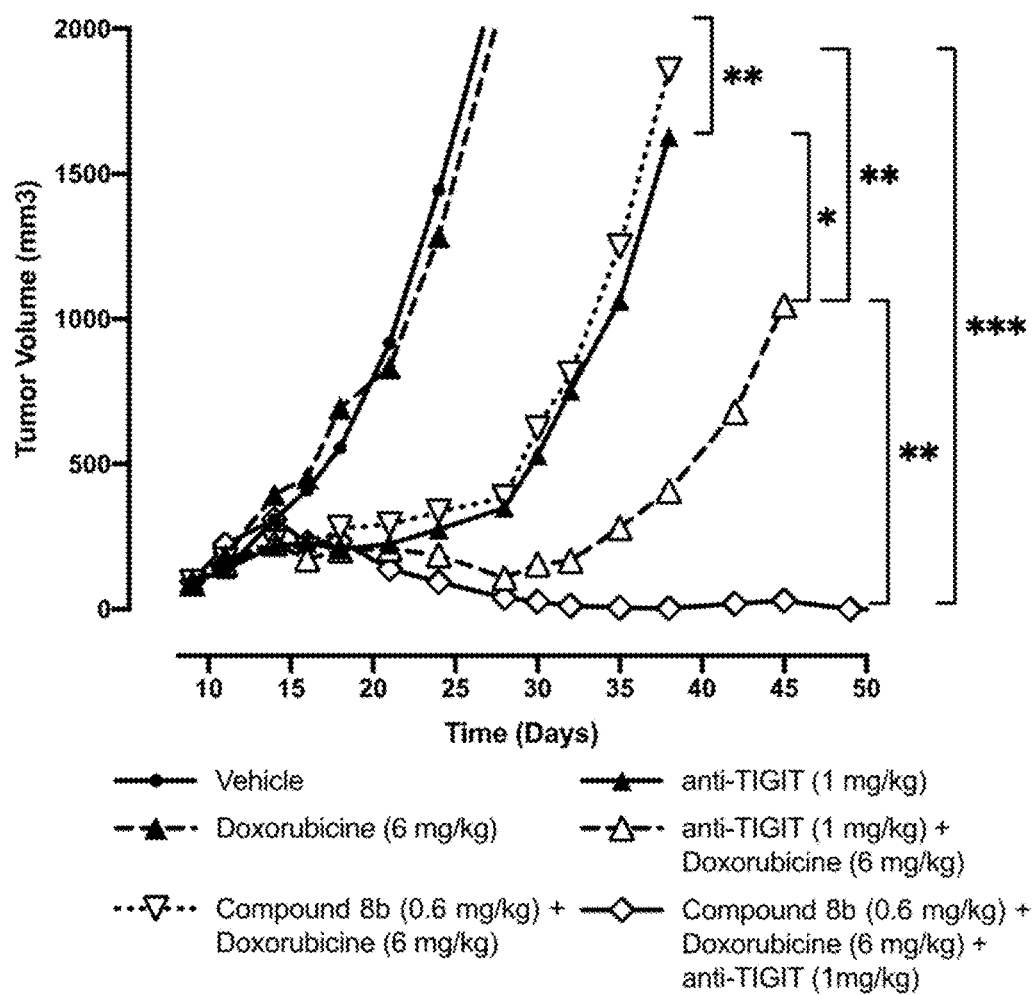
Figure 6B:
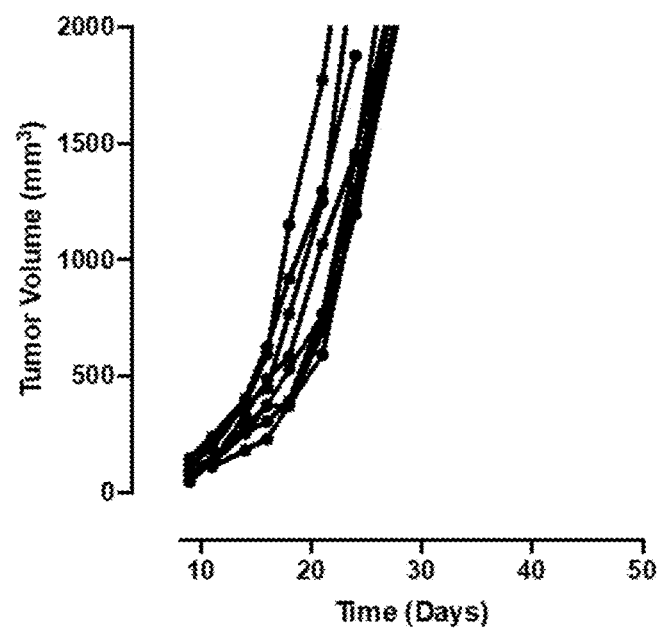
Figure 6C:
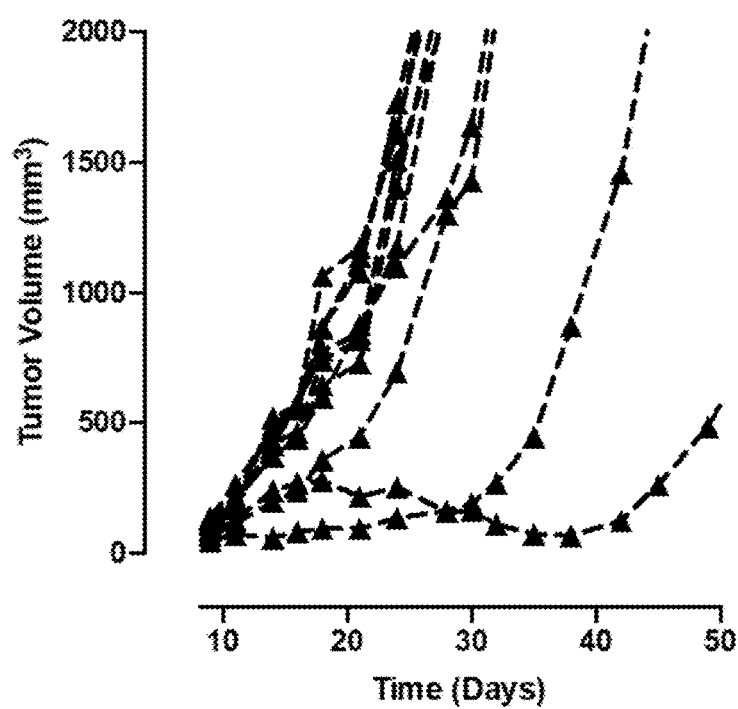
Figure 6D:
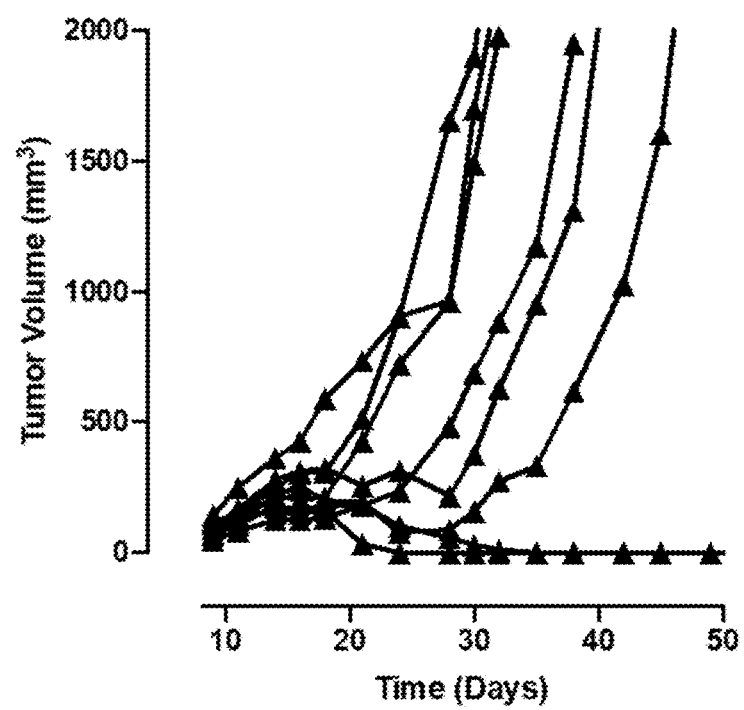
Figure 6E:
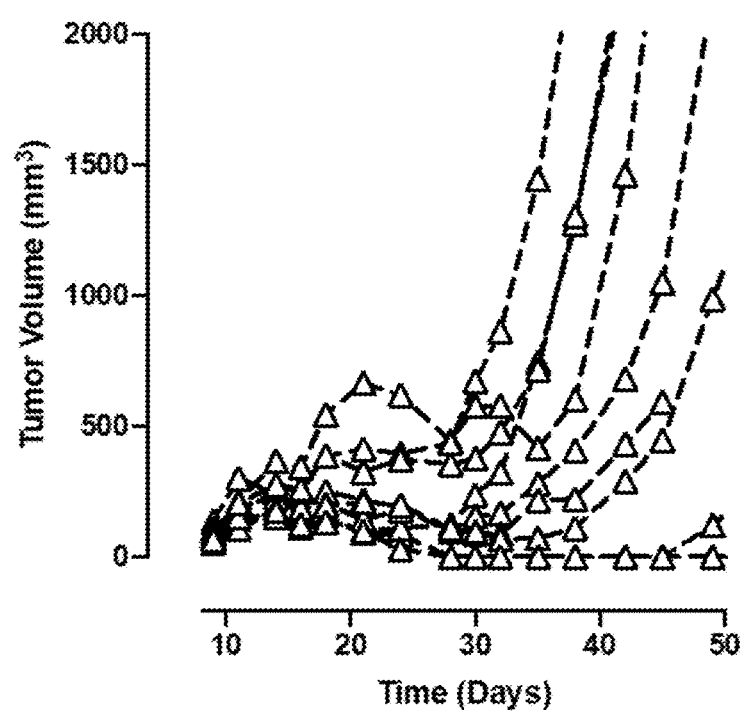
Figure 6F:
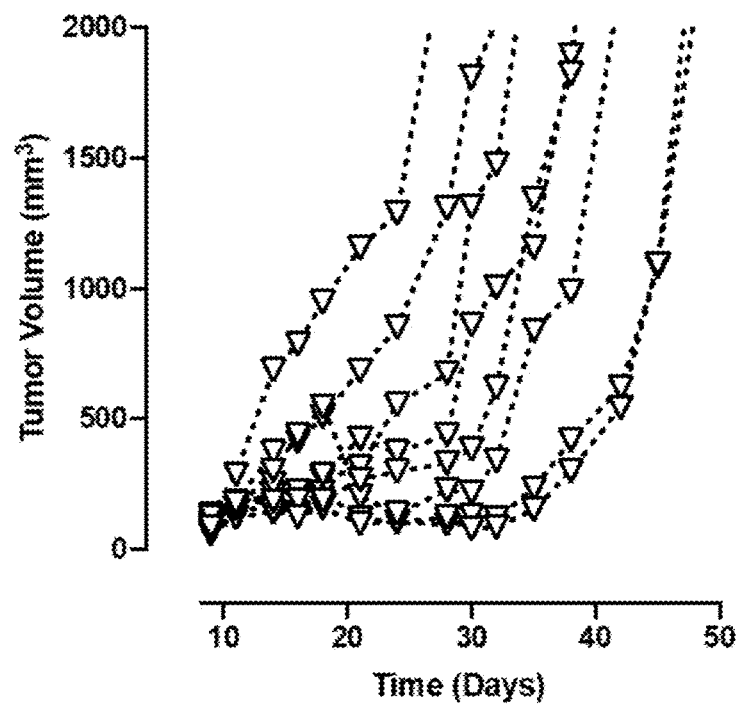
Figure 6G:
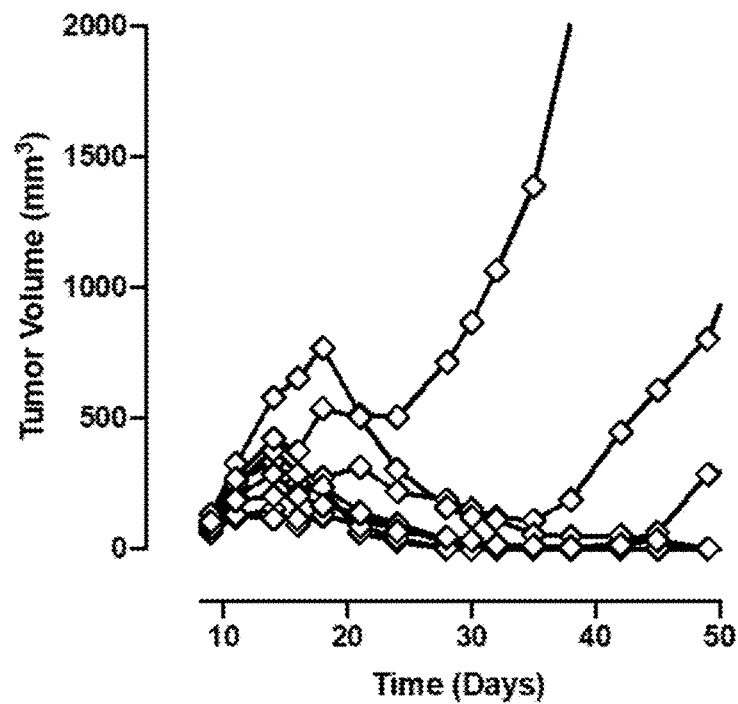

FIGS. 6A-G show the CT26 tumor growth upon treatment with Compound 8b at 0.6 mg/kg QD×32, anti-TIGIT mAb at 1 mg/kg Q3D×3 (day 9, 12 and 15), Doxorubicin 6 mg/kg Q3D×2 (day10 and 14), and various combinations thereof. FIG. 6A is a graph representing the median tumor volume over time after subcutaneous inoculation of tumor cells. FIGS. 6B-D are the individual tumor growth volumes of mice treated with Vehicle (FIG. 6B), Doxorubicin (FIG. 6C) or anti-TIGIT mAb (FIG. 6D). FIGS. 6E-G are the individual tumor growth volumes of mice treated with a combination of Doxorubicin and anti-TIGIT (FIG. 6E), Compound 8b and Doxorubicin (FIG. 6F) and triple combination of Compound 8b, Doxorubicin and anti-TIGIT (FIG. 6G).

Figure 7A:
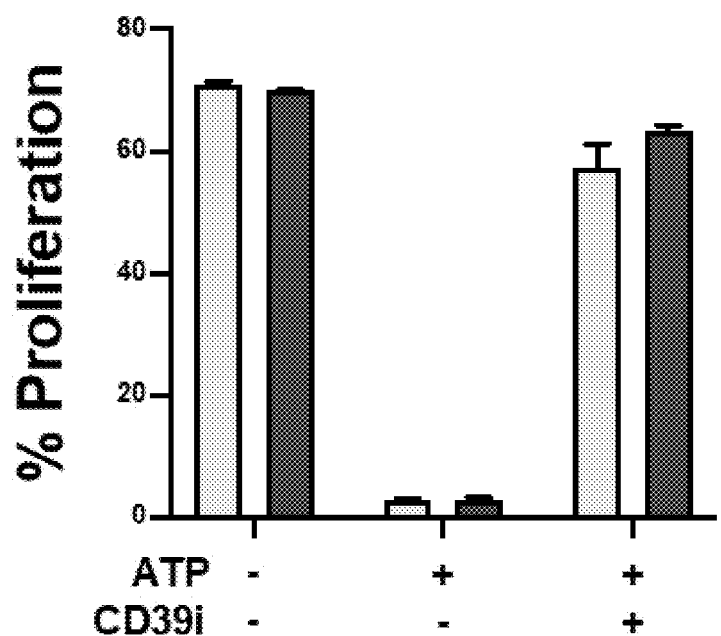
Figure 7B:
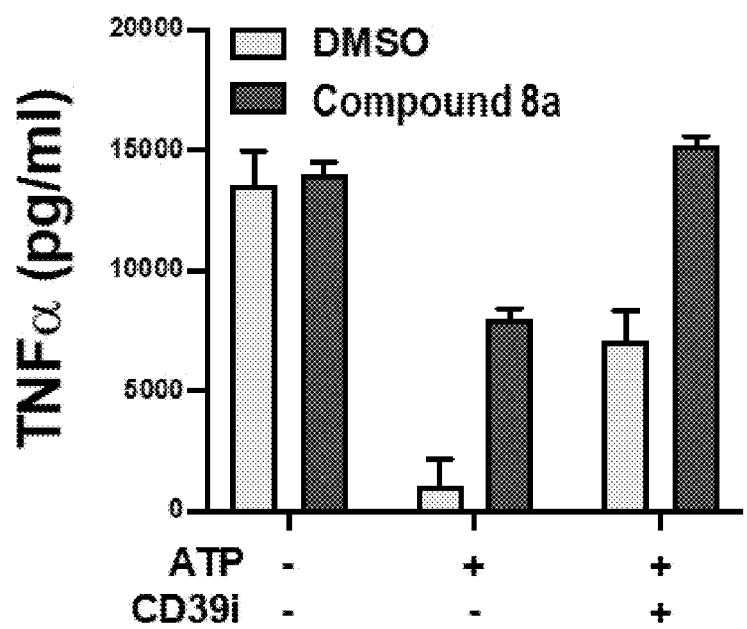

FIG. 7A shows the proportion of proliferating $CD4^+$ cells as determined by CFSE dilution. FIG. 7B shows the concentration of TNFα present in the cell culture supernatants. CD39i denotes the combination of the CD39 inhibitors ARL67156 and POM-1. Dark grey bars show Compound 8a treated wells, whilst light grey bars denote concentration-matched DMSO treated wells. Results are shown as mean value from duplicate wells standard deviation.

EXAMPLES

The present invention will be better understood with reference to the following examples. These examples are intended to representative of specific embodiments of the invention, and are not intended as limiting the scope of the invention.

The following abbreviations are used:
BHT: butylated hydroxytoluene
BID: bis in die (i.e. twice a day)
ca.: circa
CR: complete responder
DMSO: dimethylsulfoxide
EDTA: ethylenediaminetetraacetic acid
HPLC: high-performance liquid chromatography
LC-MS: liquid chromatography-mass spectrometry
mAb: monoclonal antibody
mg: milligram
MS: mass spectrometry
PBS: phosphate buffered saline
PEG: polyethylene glycol
QD: quaque die (i.e. once a day)
Q3D: quaque 3 die (i.e. every 3 days)
rpm: revolutions per minutes
TGI: tumor growth inhibition
TILs: tumor infiltrating lymphocytes
UV: ultraviolet
µL: microliter
% v/v: percentage in volume to the total volume of the composition
% w/w: percentage in weight to the total weight of the composition I. Compounds The compounds of Formula (I) are prepared as described in PCT/EP2018/058301.

II. Pharmaceutical Compositions

II.1. Manufacturing of Pharmaceutical Compositions

Two composition according to the invention were prepared under capsules form, comprising the following ingredients (Table 2):

TABLE 2

| Components | Capsules compositions (% w/w). | | | | | | | |
|---|---|---|---|---|---|---|---|---|
| | 1 | 2A | 3 | 4 | 5 | 6 | 7 | 8 |
| Compound 8a | 10 | 10 | 10 | | | | | |
| Compound 8a esylate salt | | | | 10 | 10 | 10 | 10 | |
| Compound 8a HCl salt | | | | | | | | 10 |
| Gelucire ® 44/14 | 71.9 | 80.9 | 71.9 | | | | 89 | 90 |
| Vitamin E TPGS | | | | 71 | 71 | 71 | | |
| PEG 400 | 18 | \ | | 18 | | | | |
| PEG 3350 | | | 18 | | 18 | 18 | | |
| Caprylic acid | \ | 9 | | | | | | |
| Butylated hydroxytoluene (BHT) | 0.1 | 0.1 | 0.1 | | | | | |
| polyvinyl caprolactam-polyvinyl acetate-polyethylene glycol graft copolymer | | | | | 1.0 | 1.0 | 1.0 | |
| Hydroxypropylmethylcellulose | | | | | | | 1.0 | |

Capsules 2A were prepared from a common blend using conventional mixing and capsule filling processes according to Good Manufacturing Practice. Lauroyl polyoxyl-32 glycerides is melted with a product temperature not less than 50° C. but not exceeding 80° C. Caprylic acid and then butylated hydroxytoluene (BHT) are then added to the lauroyl polyoxyl-32 glycerides and mixed together using a suitable mixer. Compound 8a is then added gradually to the lauroyl polyoxyl-32 glycerides/caprylic acid/BHT mixture being continuously mixed together using a suitable mixer to produce a visually uniform distribution of the drug substance with no observable lumps or agglomerates. Mixing is then continued for at least 30 minutes to ensure that the drug substance is homogeneously distributed as determined visually. The blend is then maintained in the molten state with continued mixing and is filled into appropriately sized gelatine capsule shells to the target capsule fill weight. Capsule filling is undertaken using conventional capsule filling methods and equipment suitable for use with molten semi-solid formulations.

A similar process was carried out for manufacturing all other capsule examples, with Vitamin E TPGS being substituted for lauroyl polyoxyl-32 glycerides. Polyvinyl caprolactar-polyvinyl acetate-polyethylene glycol graft copolymer and hydroxypropylimethylcellulose are added to the molten lauroyl polyoxyl-32 glycerides or Vitamin TPGS as required.

II.2. Pharmacology Examples

II.2.i. Thermodynamic Solubility by Shake Flask—HPLC

This example aims at showing that the compounds of Formula (I) are poorly soluble in water or in aqueous buffers and thus that there is a need to provide a formulation of said compounds.

Compound 8a (2.0 mg, crystalline solid) was weighed into the lower chambers of Whatman miniuniprep vials. 450 µL of tested medium was added into each chamber. After this addition, filter pistons of miniuniprep vials were placed and compressed to the position of the liquid level to allow for contact of the medium and compound with the filter during incubation. The samples were vortexed for 2 minutes, then incubation was carried out at room temperature (ca. 22-25° C.) for 24 hours with shaking at 880 rpm. The miniunipreps were compressed to prepare the filtrates for injection into HPLC system. The supernatants were diluted with the medium by a factor of 50 folds to make diluents. Three UV standard solutions were injected into HPLC from low to high concentration, followed by testing of the diluents and supernatants. Testing samples were injected in duplicate.

The results are shown in Table 3:

TABLE 3

Solubility of Compound 8a in tested aqueous media.

| Tested medium | Thermodynamic solubility of Compound 8a (µg/mL) |
|---|---|
| water | <0.6 |
| pH 7.4 | 2 |
| FaSSIF | 1-10 |

In all tested aqueous media, the solubility is very low and the test in FaSSIF (Fasted-State Simulated Intestinal Fluid) is representative of a low intestinal solubility.

II.2.ii. Exposures in Dogs after Oral Dosing

The purpose of this assay is to determine the exposure in dogs after oral dosing with the pharmaceutical composition of the invention. Dogs are administered with pentagastrin just before administration of the capsules formulations in order to stimulate the secretion of gastric acid.

Five male Beagle dogs (>6 months of age, 7-9 kg of weight) were fed the afternoon (at 3:30 to 4:00 pm) prior to the day of oral dosing and the remaining food was removed at about 7:00 pm. Food was withheld until after the 4-hour blood collection.

Pentagastrin (Sigma, 1 mg) was dissolved in 200 µL (0.200 mL) of a solution of 10% (v/v) ammonium hydroxide ($NH_4OH$)/90% (v/v) Phosphate Buffered Saline (PBS).

0.12 mL of this stock solution was then diluted by adding 4.88 mL of PBS solution, then the vial was vortexed. The solution was filtered (under a laminar flow hood) through a 0.22 µm syringe filter into a sterile amber glass serum bottle. Animals were administered with Pentagastrin at 6 µg/kg by intramuscular injection at approximately 30 minutes (±2 min) before dosing with the capsules.

The dose capsule formulations (80 mg/dog, i.e. about 10 mg/kg of animal) were administered by placing the capsules in the far back of the dog's throat, then pushing it past the pharynx using a thumb or index finger. The capsules were moistened with water to facilitate dosing. After administering the dose, swallowing was induced, if needed, by gently stroking the dog's throat or tapping the dog under the chin. Immediately following capsule administration, water (4 mL/kg) or an aqueous HCl solution at pH 2.5 (4 mL/kg) was given to the mouth to the animals to help capsule swallowing. After administration, the animals' mouths were inspected to ensure that the dose had been swallowed.

Blood was collected at the timepoints indicated in Table 4 into a tube (Jiangsu Kangjian medical supplies co., LTD) containing Potassium ($K_2$) EDTA*$2H_2O$ (0.85-1.15 mg) on wet ice and processed for plasma by centrifugation (3,000×g for 10 minutes at 2 to 8° C.) within one hour of collection. The plasma samples (0.2 mL) were transferred into labeled polypropylene micro-centrifuge tubes and stored frozen at −60° C. or lower until bio-analysis.

Concentrations of Compound 8a in plasma were quantified by LC-MS/MS. The concentrations measured (mean of five dogs) are indicated in Table 4, while the main pharmacokinetic parameters are indicated in Table 5.

TABLE 4

Concentration of Compound 8a in plasma.

| Timepoint (h) | Formulation 1 Concentration (ng/mL) | Formulation 2A Concentration (ng/mL) |
|---|---|---|
| 0.25 | 94.7 | 94.4 |
| 0.50 | 431 | 292 |
| 1.0 | 242 | 384 |
| 2.0 | 161 | 108 |
| 4.0 | 9.91 | 10.5 |
| 8.0 | 3.42 | 3.45 |
| 12 | 4.68 | <1 |

TABLE 5

Pharmacokinetic parameters.

|  | Formulation 1 | Formulation 2A |
| --- | --- | --- |
| Dose (mg/dog) (active ingredient) | 80 | 80 |
| Additional liquid | Water | Aqueous HCl pH 2.5 |
| $C_{max}$ (ng/mL) | 481 | 674 |
| $T_{max}$ (h) | 0.9 | 1 |
| $AUC_{last}$ (h*ng/mL) | 554 | 1818 |
| $AUC_{inf}$ (h*ng/mL) | 561 | 1823 |

$C_{max}$: maximum plasma concentration of the active ingredient obtained after administration;
$T_{max}$: time to reach $C_{max}$;
AUC: area under the curve, corresponding to the integral of the concentration-time curve ($AUC_{last}$: AUC up to the last sample drawn;
$AUC_{inf}$: AUC up to infinite time)

Above results clearly evidence that the use of the pharmaceutical composition of the invention enables suitable oral bioavailability of the thiocarbamates A2A inhibitors.

III. Combinations with Anticancer Agents—In Vivo Studies

Summary of the Results

Compound 7 at 3 mg/kg BID, significantly delayed growth of HEPA-1-6 tumors compared to vehicle control in syngeneic host.

In combination with anti-PD-L1, Compound 7 demonstrated anti-tumor activity at 0.3 mg/kg BID and, at 3 mg/kg BID, significantly delaying tumor growth versus anti-PD-L1 control in a A20 syngeneic mouse lymphoma model.

In combination with anti-CTLA-4, Compound 8a demonstrated antitumor activity at 0.1 mg/kg and starting at 0.6 mg/kg significantly delayed tumor growth in a dose dependent manner in the EMT6 syngeneic mouse breast cancer model. In addition, in cured mice, prevented growth after re-inoculation suggesting induction of a specific memory response.

Further illustrating the mechanism of action, in combination with anti-PD-L1, Compound 8a at 3 mg/kg BID significantly increased CD3$^+$ and CD8$^+$ cell infiltrations without an effect of FOXP3 expressing cells.

In combination with Oxaliplatin, Compound 8b demonstrated significant antitumor activity at 0.6 mg/kg by delaying tumor growth in the MCA205 syngeneic mouse fibrosarcoma cancer model.

In combination with Doxorubicin, Compound 8b demonstrated significant antitumor activity at 0.6 mg/kg by delaying tumor growth in the CT26 syngeneic mouse colon cancer model. In the same example a triple combination of Doxorubicin, anti-TIGIT mAb at 1 mg/kg and Compound 8b at 0.6 mg/kg demonstrated significantly enhanced antitumor activity compared to double combinations of Doxorubicin and Compound 8b or Doxorubicin and anti-TIGIT mAb in the CT26 syngeneic mouse colon cancer model.

III.1. Syngeneic HEPA1-6 Mouse Liver Tumor Model

This study evaluated the anti-tumor activity of Compound 7 in a mouse hepatoma model (NCR-A2A-032).

C57BL/6 female mice (8 weeks old) were inoculated subcutaneously in the right flank region with Hepa 1-6 tumor cells (on day 0). When tumor size reached about 50 mm$^3$ (on Day 4), mice were randomly allocated into experimental groups and treatment was initiated from day 4 to 25. Mice were administered vehicle p.o. (10% DMSO, 10% Solutol HS15 in dH$_2$O pH3) or Compound 7 at 0.3 and 3 mg/kg, p.o., BIDx 21.

Figure 1A:
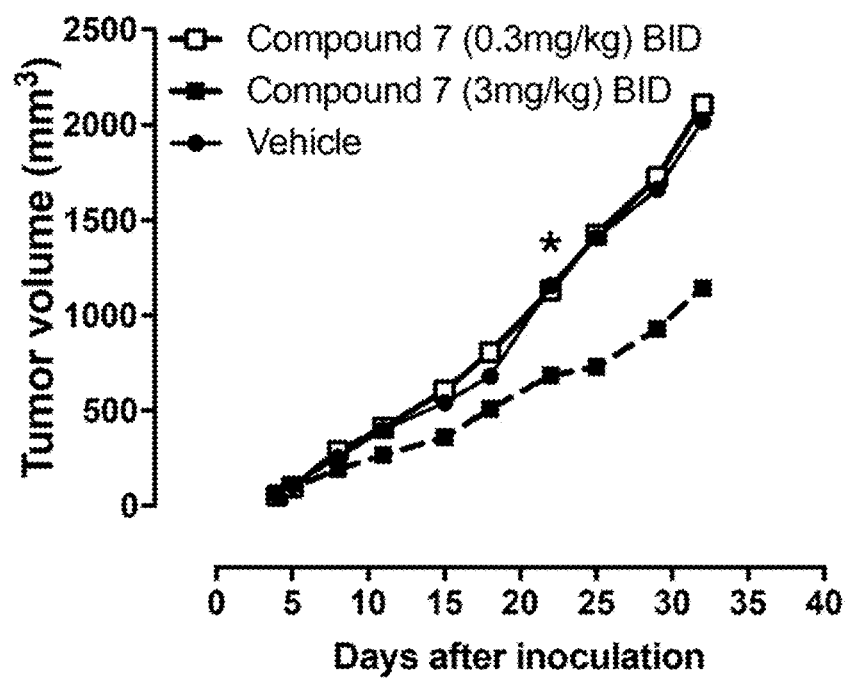
FIGS. 1A and 1B show the anti-tumor efficacy of A2AR inhibitor Compound 7 administered as single agent in liver Hepa 1-6 syngeneic tumor model.
Figure 1B:
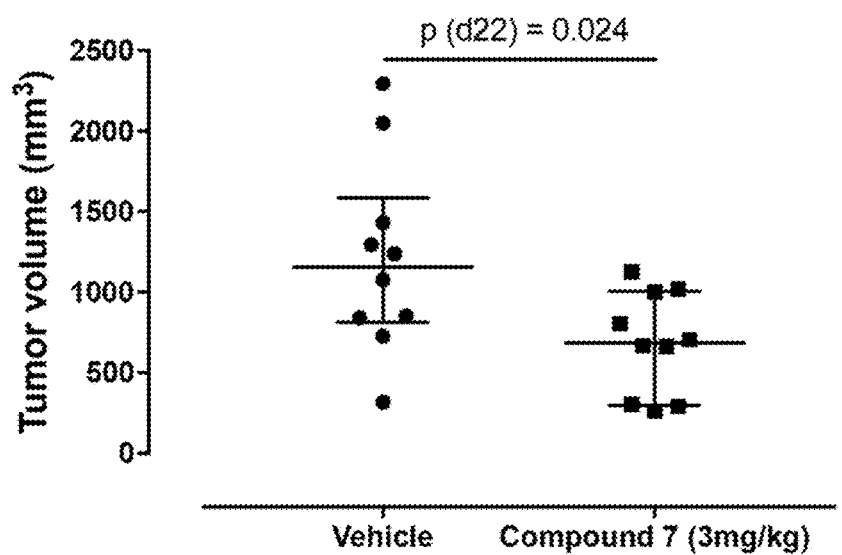

At 3 mg/kg, Compound 7 demonstrated significant anti-tumor efficacy with a tumor growth inhibition (TGI) of 44% calculated on Day 22 (p=0.024). (FIGS. 1A and 1B).

III.2. Syngeneic A20 Experimental Lymphoma Model in Combination with Anti-PD-L1

In this study the anti-tumor efficacy of Compound 7 was assessed either as single agent (monotherapy) or in combination with antagonist anti-Programmed Death-Ligand 1 (anti-PD-L1) monoclonal antibody (10F.9G2, BioXcell) in a model of B cell lymphoma model. (NCR-A2A-031).

BALB/c female mice (8 weeks old) were inoculated with A20 mouse B-cell tumor cells, subcutaneously in the right lower flank region (day 0). When tumors reached a size of about 50 mm$^3$ (Day 7), mice were allocated randomly into groups and treatment was initiated. Mice were administered vehicle p.o. (10% DMSO, 10% Solutol HS15 in dH$_2$O pH3) as control or Compound 7 at 0.3 and 3 mg/kg, p.o., BIDx 21 (Day 7 to 28) or anti-PD-L1 mAb at 5 mg/kg i.p., Q3Dx3 (day 9, 12, 15) as single agent or in combination.

Compound 7 administered p.o. at 0.3 mg/kg, BID, in combination with anti-PD-L1 mAb, demonstrated anti-tumor activity (TGI=76%, determined on day 23) although not reaching statistical significance (p=0.106) compared with anti-PD-L1 single therapy (TGI=49%).

Figure 2A:
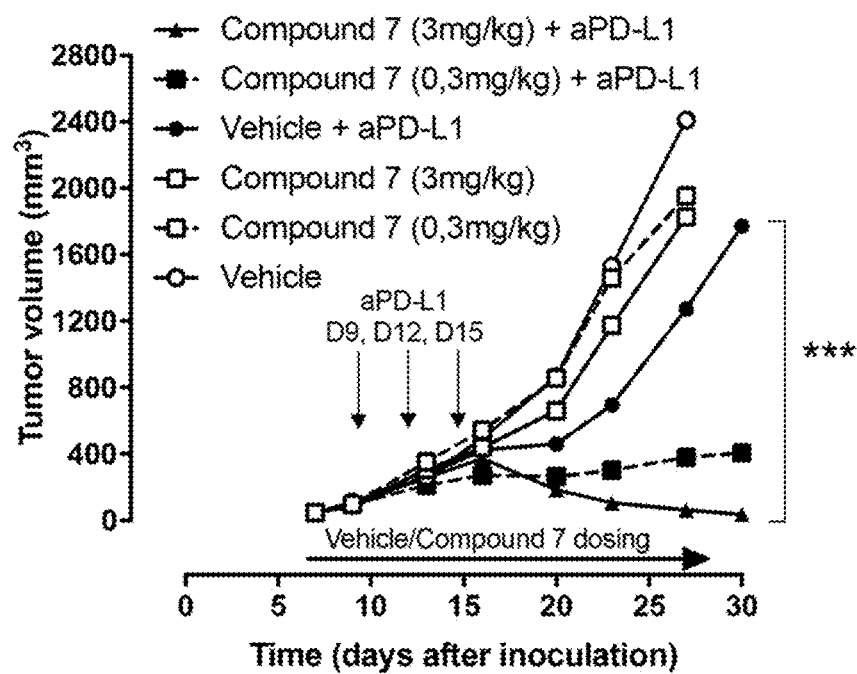
FIGS. 2A and 2B show the A20 tumor growth upon treatment with Compound 7 used as single agent or in combination with anti-PD-L1.
Figure 2B:
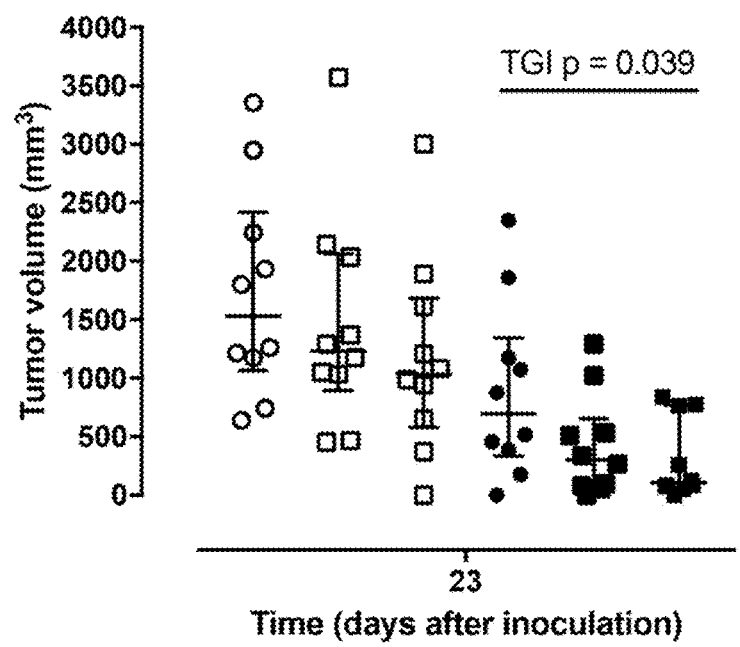

Compound 7 administered at 3 mg/kg BID in combination with anti-PD-L1 mAb, showed significant enhancement of antitumor activity (p=0.039 for TGI and p=0.0008 for overall suppression of tumor growth) compared with single agent anti-PD-L1 mAb (TGI=82 and 49%, observed on day 23, respectively) (FIGS. 2A and 2B).

Statistical analysis also revealed that Compound 7 synergises with anti-PD-L1 mAb to significantly inhibit the growth of established A20 syngeneic tumor (p=0.017).

III.3. Syngeneic EMT6 Breast Cancer Model in Combination with Anti-CTLA-4

The anti-tumor efficacy of Compound 8a was assessed in combination with anti-cytotoxic T lymphocyte-associated antigen-4 (CTLA-4) antagonist mAb (9H10, BioXcell) in a model of triple negative mammary cancer.

EMT6 mammary tumor cells were inoculated orthotopically into the lower right mammary fat pad of 8 week old female BALB/c mice (day 0). When tumors reached a size of about 60 mm$^3$ (day 9), mice were randomly allocated into groups. Mice were administered with control vehicle p.o. (10% DMSO, 10% Solutol HS15 in dH$_2$O pH3) or anti-CTLA-4 mAb at 3 mg/kg i.p., Q3Dx2 (day 9, 12) stand alone or in combination with Compound 8a at 0.1 mg/kg p.o. QDx25 or 0.6 mg/kg p.o. QDx25.

Compound 8a combined with anti-CTLA-4 significantly reduced tumor growth when administered at 0.6 mg/kg (p=0.0153, mean TGI=99% determined on day 31-complete responder (CR)=7/10) vs. anti-CTLA4 alone (CR=3, mean TGI=72%, determined on day 31) (FIGS. 3A, 3B, 3C and 3E). Although Compound 8a at 0.1 mg/kg in combination with anti-CTLA-4 mAb (as above) did not reach statistical significance (p=0.8665) vs. anti-CTLA4 mAb as single agent, it resulted in CR=5 (n=10 mice group) and mean TGI=85% (FIGS. 3A and 3D). In addition, there was also no statistically significant difference between doses. This suggests that Compound 8a already demonstrates in vivo activity starting at 0.1 mg/kg in combination with anti-CTLA4 mAb (FIGS. 1A and 1B).

When complete responders (cure mice) re-challenged with EMT6 tumor cells (specific antigen) or unrelated colon CT26 cells (non-specific antigen), the mice previously treated with Compound 8a at 0.1 and 0.6 mg/kg in combination with anti-CTLA-4 mAb, were not protected against the challenge of unrelated CT26 cells (100% of tumor incidence) but fully rejected EMT6 cells (no tumor formation) in 66% (0.1 mg/kg) and 100% (0.6 mg/kg) of mice respectively.

Compound 8a therefore significantly inhibited the growth of established EMT6 syngeneic tumors in combination with anti-CTLA-4 antagonist mAb and induce long-term memory response that results in durable specific antitumor response.

III.4. Mechanism of Action of Compound 8A to Reduce Tumor Growth in A20 Lymphoma Model Having established that Compound 8a (or its racemate mixture, Compound 7) demonstrates anti-tumor activity in several experimental tumor models at well-tolerated doses, this study evaluated the mechanism of action responsible for this effect.

Compound 8a was evaluated in B cell Lymphoma tumor model, as single agent and in combination with antagonist anti-PD-L1 mAb. A20 tumor-bearing mice (tumor size of about 70 mm$^3$, day 12 after inoculation) were treated with control vehicle p.o. (10% DMSO, 10% Solutol HS15 in dH$_2$O pH3) or anti-PD-L1 mAb at 1 mg/kg i.p., Q3D×3 (day 14, 17 and 20) and Compound 8a 3 mg/kg p.o., BID×10 as single agent or in combination with anti-PD-L1 mAb. By IHC staining, the tumor-infiltrating lymphocytes (TIL), including total CD3$^+$ T cells, CD8$^+$ T cells and FOXP3$^+$ Treg cells, were characterized and compared using a semi-quantitative technique.

Compound 8a at 3 mg/kg as single agent regimen had a moderate effect on CD3$^+$ and CD8$^+$ TILs in the tumor environment but the increase in infiltrate did not reach significance. The combination of Compound 8a at 3 mg/kg with anti-PDL-1 mAb demonstrated a significant increase in CD3$^+$ T cells (p=0.0068) and CD8$^+$ T cell (p=0.0035) infiltration in tumor as compared to anti-PDL-1 mAb used as single agent (FIGS. 4A and 4B). No statistically significant change in Treg infiltrate was demonstrated with any treatment in single agent or combination.

These results strongly suggest that Compound 8a in combination with aPDL-1 mAb significantly modulates the immunosuppressive nature of the tumor microenvironment by increasing TILs infiltration.

III.5. Syngeneic MCA205 Experimental Fibrosarcoma Model in Combination with Oxaliplatin The anti-tumor efficacy of Compound 8b was assessed in combination with Oxaliplatin, in an established murine syngeneic MCA205 fibrosarcoma tumor model.

MCA205 tumor cells were inoculated subcutaneously into the right flank of C57BL/6 mice. When tumors reached an average size of about 80 mm$^3$, mice were randomly allocated into groups. Mice were administered vehicle p.o. (10% DMSO, 10% Solutol HS15 in dH$_2$O pH3) as control or Compound 8b at 0.6 mg/kg QD×25 (day 11-36) or Oxaliplatin at 10 mg/kg i.p. QD×1 (day11) as single agent or in combination.

Oxaliplatin, given as a single administration i.p. at D11, demonstrated a significant delay in tumor growth (p=0.0202) compared to the Vehicle (FIGS. 5A, 5B, and 5D).

Compound 8b, administered p.o. at 0.6 mg/kg once daily (QD) for 25 consecutive days in combination with Oxaliplatin, demonstrated significant tumor growth delay compared to Vehicle (p<0.0001) and also significant tumor growth delay when compared to Oxaliplatin monotherapy (p=0.0284) (FIGS. 5A-E).

III.6. Syngeneic CT26 Experimental Colon Cancer Model in Combination with Doxorubicin and/or Anti-TIGIT Mab In this study the anti-tumor efficacy of Compound 8b was assessed in combination with chemotherapeutic agent, Doxorubicin and with anti-TIGIT mAb in a Colon tumor model (CT26).

BALB/c female mice (8 weeks old) were inoculated with CT26 mouse tumor cells, subcutaneously in the right lower flank region (day 0). When tumors reached a size of about 90 mm$^3$ (Day 9), mice were allocated randomly into groups and treatment was initiated. Mice were administered vehicle p.o. (10% DMSO, 10% Solutol HS15 in dH$_2$O pH3) as control or Doxorubicin at 6 mg/kg i.v., Q4D×2 (day 10 and 14) or anti-TIGIT mAb, 29527 (see U.S. Ser. No. 10/329,349) at 1 mg/kg i.p. Q3D×3 (day 9, 12 and 15), as single agent or in combinations with Compound 8b at 0.6 mg/kg, p.o., QD×32 (Day 9 to 41).

Intraperitoneal injection of 1 mg/kg of anti-TIGIT mAb, 29527 (see U.S. Ser. No. 10/329,349) at days 9, 12 and 15 after tumor cell inoculation, significantly suppressed tumor growth compared to mice treated with vehicle (p=0.0009, FIGS. 6A and 6B)

Doxorubicin, administered twice at 6 mg/kg on day 10 and 14, had no significant effect on tumor growth (p=0.14, FIGS. 6A and 6C), while combination with anti-TIGIT mAb improved anti-tumor efficacy (p=0.008 and p=0.0002 respectively, when compared to anti-TIGIT mAb or Doxorubicin stand-alone therapy (FIGS. 6A, 6C, 6D, and 6E).

Compound 8b administered at 0.6 mg/kg QD from day 9 in combination with Doxorubicin given at 6 mg/kg on day 10 and 14 achieved significant anti-tumor effect when compared to stand alone administration of Doxorubicin (p=0.0003, FIGS. 6A, 6C, and 6F). The anti-tumor growth efficacy in mice treated with a triple combination of Compound 8b, Doxorubicin and anti-TIGIT, was significantly higher when compared to Doxorubicin+Compound 8b (p<0.0001) or when compared to anti-TIGIT+Doxorubicin (p=0.003), and resulted in 5 complete responders (CR) out of 8 mice in this triple combination treated group verses zero and one CR out of 10 mice in the Doxorubicin+Compound 8b and anti-TIGIT+Doxorubicin combinations respectively. (FIGS. 6A, 6E, 6F, and 6G).

III.7. Restoration of Human T Cells Function by a Combination with CD39 Inhibitors Purpose. When T cells are activated, they proliferate and produce pro-inflammatory cytokines. Addition of adenosine triphosphate (ATP) to the culture provides a source of adenosine as ATP is first converted to adenosine monophosphate by CD39 and then to adenosine by CD73. Adenosine suppresses T cell proliferation and cytokine production in part by engaging the A$_2$A receptor. The present assay thus aims to show that the inhibition of proliferation and inflammatory cytokine production by T cells in the presence of ATP may be reversed by a combination of the $A_2A$ receptor antagonist Compound 8a and the CD39 inhibitors ARL67156 and POM-1.

PBMC and CD3+ T cell isolation. Venous blood from healthy volunteers was obtained via ImmuneHealth (Centre Hospitalier Universitaire Tivoli, La Louviere, Belgium). Peripheral blood mononuclear cells (PBMCs) were collected by density gradient centrifugation, using SepMate-50 tubes (StemCell Technologies, Grenoble, France) and Lymphoprep (Axis-shield, Oslo, Norway) according to the manufacturer's instructions. PBMCs were stored in heat inactivated foetal bovine serum (hiFBS; Gibco, ThermoFisher Scientific, Merelbeke, Belgium) containing 10% DMSO in liquid nitrogen until required. PBMCs were thawed and washed into PBS (with 10% hiFBS) and labelled with 1 μM CFSE (Life Technologies) at room temperature for 5 minutes. Cells were washed into StemCell isolation buffer and CD3+ T cells were isolated by immunomagnetic negative selection, using the EasySep Human T Cell Isolation Kit (StemCell Technologies) as per manufacturer's instructions.

Human T cell activation assay. Human CD3+ T cells were washed into X-VIVO15 medium (LONZA) and distributed into a 96 round well plate at $8 \times 10^4$ cells per well. Wells received either the A2A receptor antagonist compound 8a at a final concentration of 100 nM or a matched concentration of DMSO (Sigma-Aldrich). In addition, some wells received a combination of the CD39 inhibitors ARL67156 (Tocris Bioscience, 100 μM) and POM-1 (Tocris Bioscience, 10 μM), or a combination of both CD39 inhibitors and compound 8a. Cells were cultured in the presence or absence of ATP (Sigma-Aldrich) at a final concentration of 100 μM and were activated by adding anti-CD3 and anti-CD28 coated microbeads (Dynabeads human T-activator CD3/CD28; Life Technologies).

Cells were placed in a 37° C. humidified tissue culture incubator with 5% $CO_2$ for 72 hours. After 72 hours, supernatants were sampled and stored at −20° C. Proliferation of CD4+ T cells was assessed by determining CFSE dilution by flow cytometry using a BD LSRFortessa (BD Biosciences). Supernatants were later thawed and TNFα was quantified using the AlphaLISA Human TNFα Biotin-Free Detection Kit (AL325; Perkin-Elmer, Zaventem, Belgium), according to the manufacturer's instructions.

Results. The presence of ATP significantly inhibited CD4+ T cell proliferation which was almost completely rescued by the CD39 inhibitors ARL67156 and POM-1 (FIG. 7A). The presence of compound 8a made a small further contribution to increasing proliferation of these cells. ATP also significantly inhibited the production of TNFα. Both compound 8a and the CD39 inhibitors individually could restore approximately 50% of TNFα production, with a combination resulting in complete rescue (FIG. 7B). Overall, these data illustrate the value of combining compound 8a with a CD39 inhibitor for cancer immunotherapy, aiming at full restoration of T cell function in the ATP-rich tumor microenvironment.

---

The invention claimed is:

1. A method of treating cancer in a patient in need thereof, the method comprising administering to the patient a therapeutically acceptable effective amount of a combination comprising:
(S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one, or a pharmaceutically acceptable salt thereof; and
a checkpoint inhibitor selected from the group consisting of a PD-1 antibody and a PD-L1 antibody.

2. The method according to claim 1, wherein the checkpoint inhibitor is a PD-1 antibody.

3. The method according to claim 1, wherein the checkpoint inhibitor is a PD-L1 antibody.

4. The method of claim 1, wherein the cancer is selected from the group consisting of breast, carcinoid, cervical, colorectal, endometrial, glioma, head and neck, liver, lung, melanoma, ovarian, pancreatic, prostate, renal, gastric, thyroid and urothelial cancers.

5. The method of claim 1, wherein the cancer is selected from breast cancer, prostate cancer, melanoma, and solid tumor.

6. The method of claim 1, wherein the administration of (S)-5-amino-3-(2-(4-(2,4-difluoro-5-(2-(methylsulfinyl)ethoxy)phenyl)piperazin-i-yl)ethyl)-8-(furan-2-yl)thiazolo[5,4-e][1,2,4]triazolo[1,5-c]pyrimidin-2(3H)-one, or a pharmaceutically acceptable salt thereof is administered prior to, concomitantly with, or subsequent to administration of the checkpoint inhibitor.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: HCDR1

<400> SEQUENCE: 1

Tyr Thr Phe Thr Ser Tyr Tyr Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Val Ile Gly Pro Ser Gly Ala Ser Thr Ser Tyr Ala Gln Lys Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: HCDR3

<400> SEQUENCE: 3

Ala Arg Asp His Ser Asp Tyr Trp Ser Gly Ile Met Glu Val
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: LCDR1

<400> SEQUENCE: 4

Arg Ala Ser Gln Ser Val Arg Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Gly Ala Ser Ser Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln Gln Tyr Phe Ser Pro Pro Trp Thr
1               5
```